United States Patent [19]
Trueheart et al.

[11] Patent Number: 6,159,705
[45] Date of Patent: Dec. 12, 2000

[54] RECOMBINANT YEAST CELLS FOR IDENTIFYING RECEPTOR EFFECTORS

[75] Inventors: Joshua Trueheart, Concord, Mass.; Jeremy I. Paul, Nyack, N.Y.; Hans A. Fuernkranz, San Jose, Calif.; Debra Nathan, Mt. Kisco, N.Y.; Scott Holmes, Middlebury, Conn.

[73] Assignee: Cadus Pharmaceutical Corporation, New York, N.Y.

[21] Appl. No.: 08/936,632

[22] Filed: Sep. 24, 1997

Related U.S. Application Data

[63] Continuation-in-part of application No. 08/718,910, Sep. 24, 1996, abandoned, and a continuation-in-part of application No. 08/851,469, May 5, 1997, abandoned.

[51] Int. Cl.$^7$ ............................... C12N 1/19; C12Q 1/02
[52] U.S. Cl. ........................................ 435/29; 435/254.11
[58] Field of Search .................................. 435/6, 7.1, 7.2, 435/69.1, 69.7, 29, 254.11; 436/501; 576/23.4

[56] References Cited

U.S. PATENT DOCUMENTS

| | | | |
|---|---|---|---|
| 4,613,572 | 9/1986 | MacKay et al. | 435/253 |
| 4,880,734 | 11/1989 | Burke et al. | 435/68 |
| 5,283,173 | 2/1994 | Fields et al. | 435/6 |
| 5,401,629 | 3/1995 | Harpold et al. | 435/6 |
| 5,436,128 | 7/1995 | Harpold et al. | 435/6 |
| 5,436,136 | 7/1995 | Hinnen et al. | 435/69.1 |
| 5,491,084 | 2/1996 | Chalfie et al. | 435/189 |
| 5,569,588 | 10/1996 | Ashby et al. | 435/6 |
| 5,571,688 | 11/1996 | Mekalanos et al. | 435/29 |
| 5,580,736 | 12/1996 | Brent et al. | 435/6 |
| 5,610,015 | 3/1997 | Wickens et al. | 435/6 |
| 5,739,029 | 4/1998 | King et al. | 435/254.21 |
| 5,876,951 | 3/1999 | Fowlkes et al. | 435/7.31 |

FOREIGN PATENT DOCUMENTS

| | | |
|---|---|---|
| 0 123 544 | 10/1984 | European Pat. Off. . |
| 0 324 274 | 7/1989 | European Pat. Off. . |
| 0 428 000 | 5/1991 | European Pat. Off. . |
| 0 528 854 | 3/1993 | European Pat. Off. . |
| 0 747 700 | 12/1996 | European Pat. Off. . |
| WO 88/10308 | 12/1988 | WIPO . |
| WO 92/05244 | 4/1992 | WIPO . |
| WO 94/16100 | 7/1994 | WIPO . |
| WO 94/23025 | 10/1994 | WIPO . |
| WO 94/28166 | 12/1994 | WIPO . |
| WO 95/21191 | 8/1995 | WIPO . |
| WO 95/30012 | 11/1995 | WIPO . |
| WO 96/23898 | 8/1996 | WIPO . |
| WO 96/25487 | 8/1996 | WIPO . |
| WO 96/27675 | 9/1996 | WIPO . |

OTHER PUBLICATIONS

Appeltauer, U. and Achstetter, T., "Hormone–induced Expression of the CHS1 Gene from *Saccharomyces cerevisiae*," Eur. J. Biochem., vol. 181, 243–7 (1989).

Geoghegan, K. et al., "Site–Directed Double Fluoescent Tagging of Human Renin and Collagenase (MMP–1) Substrate Peptides Using the Periodate Oxidation of N–Terminal Serine. An Apparently General Strategy for Provision of Energy–Transfer Substrates for Proteases," *Bioconjugate Chem.*, vol. 4, 537–44 (1993).

Hagen, D. et al., "Pheromone Response Elements are Necessary and Sufficient for Basal and Pheromone–Induced Transcription of the FUS1 Gene of *Saccharomyces cerevisiae*," *Molecular and Cellular Biology*, vol. 11, No. 6, 2952–61 (1991).

International Search Report for PCT/US97/17159, issued Jun. 17, 1998.

Liebig, H.D. et al., "Proteinase Trapping: Screening for Viral Proteinase Mutants by α Complementation," *Proceedings of the National Academy of Sciences of USA*, vol. 88, No. 14, 5979–83 (1991).

Ludwig, D. et al., "High–Level Heterologous Gene Expression in *Saccharomyces cerevisiae* from a Stable 2μm Plasmid System," *Gene*, vol. 132, 33–40 (1993).

Maggiora, L. et al., "A General Method for the Preperation of Internally Quenched Flurogenic Protease Substrates Using Solid–Phase Peptide Synthesis," *J. Med. Chem.*, vol. 35, 3727–30 (1992).

Malkova, A. et al., "Meiotic Recombination Initiated by a Double–Strand Break in rad50Δ Yeast Cells Otherwise Unable to Initiate Meiotic Recombination," *Genetics*, vol. 143, 741–54 (1996).

Manfredi, J. et al., "Yeast α Mating Factor Structure–Activity Relationship Derived from Genetically Selected Peptide Agonists and Antagonists of Ste2p," *Molecular and Cellular Biology*, vol. 16, No. 9, 4700–9 (1996).

Matayoshi, E. et al., "Novel Flurogenic Substrates for Assaying Retroviral Proteases by Resonance Energy Transfer," *Science*, vol. 247, 954–8 (1990).

McGrath, W. et al., "Characterization of Human Adenovirus Proteinase Activity in Disrupted Virus Particles," *Virology*, vol. 217, 131–8 (1996).

Packham, E. et al., "The Multifunctional Transcription Factors Abf1p, Rap1p and Reb1p are Required for Full Transcriptional Activation of the Chromosomal PGK Gene in *Saccharomyces cerevisiae*," *Mol. Gen. Genet.*, vol. 250, 348–56 (1996).

Rathjen, J. and Mellor, J., "Characterization of Sequences Required for RNA Initiation from the PGK Promoter of *Saccharomyces cerevisiae*," *Nucleic Acids Research*, vol. 18, No. 11, 3219–25 (1990).

Sakai, A. et al., "Enhanced Secretion of Human Nerve Growth Factor from *Saccharomyces Cerevisiae* Using an Advanced δ–Integration System," *Bio/Technology*, vol. 9, 1382–5 (1991).

Primary Examiner—John Ulm
Attorney, Agent, or Firm—Lahive & Cockfield, LLP; Giulio A. DeConti, Jr., Esq.; Peter C. Lauro, Esq.

[57] ABSTRACT

The present invention makes available a rapid, effective assay for screening and identifying pharmaceutically effective compounds that specifically interact with and modulate the activity of a cellular protein, e.g., a receptor or ion channel. The subject assay enables rapid screening of large numbers of compounds to identify those which act as an agonist or antagonist to the bioactivity of the cellular protein. The subject assay is particularly amenable for identifying surrogate ligands for receptors especially from small molecule or peptide libraries or from peptides produced by an autocrine system.

36 Claims, 1 Drawing Sheet

Sequence alignments of N-terminal regions of Gα subunits and N-terminal sequences of GPA₄₁-Gα hybrid proteins.

A. Alignment of GPA1 with Gα Subunits

GPA1
MGC.TVSTQTIGDESDPFLQNKRANDVIEQSLQLEKQRDKNEIKLLLLGAGESGKSTVLKQLKLLHQ......
GαS
MGCLGTS..KTEDQRNEEKAQREANKKIEKQLQKDKQVYRATHRLLLLGAGESGKSTIVKQMRILHV......
Gαi2
MGC.TVS........AEDKAAAERSKMIDKNLREDGEKAAREVKLLLLGAGESGKSTIVKQMKIIHE......
Gαi3
MGC.TVS........AEDKAAVERSKMIDRNLREDGEKAAKEVKLLLLGAGESGKSTIVKQMKIIHE......
Gα16
MARSLTWRCCPWCLTEDEKAAARVDQEINRILLEQKKQDRGELKLLLLGPGESGKSTFIKQMRIIHG......

B. GPA₄₁-Gα Hybrids

GPA₄₁- GαS
MGC.TVSTQTIGDESDPFLQNKRANDVIEQSLQLLKQRDKNERKLLLLGAGESGKSTIVKQMRILHV......
GPA₄₁- Gαi2
MGC.TVSTQTIGDESDPFLQNKRANDVIEQSLQLEKQRDKNEVKLLLLGAGESGKSTIVKQMKIIHE......
GPA₄₁- Gαi3
MGC.TVSTQTIGDESDPFLQNKRANDVIEQSLQLEKQRDKNEVKLLLLGAGESGKSTIVKQMKIIHE......
GPA₄₁- Gα16
MGC.TVSTQTIGDESDPFLQNKRANDVIEQSLQLEKQRDKNELKLLLLGPGESGKSTFIKQMRIIHG......

Fig. 1

RECOMBINANT YEAST CELLS FOR IDENTIFYING RECEPTOR EFFECTORS

RELATED APPLICATIONS

This application is a continuation-in-part of U.S. Ser. No. 08/718,910, filed Sep. 24, 1996, abandoned and a continuation-in-part of U.S. Ser. No. 08/851,469, filed May 5, 1997, abandoned the contents of each of which are hereby incorporated by reference.

BACKGROUND OF THE INVENTION

The identification of biological activity in new molecules has historically been accomplished through the use of in vitro assays or whole animals. Intact biological entities, either cells or whole organisms, have been used to screen for anti-bacterial, anti-fungal, anti-parasitic and anti-viral agents in vitro. Cultured mammalian cells have also been used in screens designed to detect potential therapeutic compounds. A variety of bioassay endpoints have been exploited in cell screens including the stimulation of growth or differentiation of cells, changes in cell motility, the production of particular metabolites, the expression of specific proteins within cells, altered protein function, and altered conductance properties. Cytotoxic compounds used in cancer chemotherapy have been identified through their ability to inhibit the growth of tumor cells in vitro and in vivo. In addition to cultures of dispersed cells, whole tissues have served in bioassays, as in those based on the contractility of muscle.

In vitro testing is a preferred methodology in that it permits the design of high-throughput screens: small quantities of large numbers of compounds can be tested in a short period of time and at low expense. Optimally, animals are reserved for the latter stages of compound evaluation and are not used in the discovery phase; the use of whole animals is labor-intensive and extremely expensive.

The search for agonists and antagonists of cellular receptors has been an intense area of research aimed at drug discovery due to the elegant specificity of these molecular targets. Drug screening has been carried out using whole cells expressing functional receptors and, recently, binding assays employing membrane fractions or purified receptors have been designed to screen compound libraries for competitive ligands.

The heterologous expression of recombinant mammalian G protein-coupled receptors in mammalian cells which do not normally express those receptors has been described as a means of studying receptor function for the purpose of identifying agonists and antagonists of those receptors. For example, the human muscarinic receptor (HM1) has been functionally expressed in mouse cells (Harpold et al. U.S. Pat. No. 5,401,629). The rat V1b vasopressin receptor has been found to stimulate phosphotidylinositol hydrolysis and intracellular Ca2+ mobilization in Chinese hamster ovary cells upon agonist stimulation (Lolait et al. (1995) Proc Natl. Acad Sci. USA 92:6783–6787). These types of ectopic expression studies have enabled researchers to study receptor signaling mechanisms and to perform mutagenisis studies which have been useful in identifying portions of receptors that are critical for ligand binding or signal transduction.

Experiments have also been undertaken to express functional G protein coupled receptors in yeast cells. For example, U.S. Pat. No. 5,482,835 to King et al. describes a transformed yeast cell which is incapable of producing a yeast G protein α subunit, but which has been engineered to produce both a mammalian G protein α-subunit and a mammalian receptor which is "coupled to" (i.e., interacts with) the aforementioned mammalian G protein α-subunit. Specifically, U.S. Pat. No. 5,482,835 reports expression of the human beta-2 adrenergic receptor (β2AR), a seven transmembrane receptor (STR), in yeast, under control of the GAL1 promoter, with the β2AR gene modified by replacing the first 63 base pairs of coding sequence with 11 base pairs of noncoding and 42 base pairs of coding sequence from the STE2 gene. (STE2 encodes the yeast (α-factor receptor). The Duke researchers found that the modified β2AR was functionally integrated into the membrane, as shown by studies of the ability of isolated membranes to interact properly with various known agonists and antagonists of β2AR. The ligand binding affinity for yeast-expressed β2AR was said to be nearly identical to that observed for naturally produced β2AR.

U.S. Pat. No. 5,482,835 describes co-expression of a rat G protein α-subunit in the same cells, yeast strain 8C, which lacks the cognate yeast protein. Ligand binding resulted in G protein-mediated signal transduction. U.S. Pat. No. 5,482,835 teaches that these cells may be used in screening compounds for the ability to affect the rate of dissociation of Gα from Gβγ in a cell. For this purpose, the cell further contains a pheromone-responsive promoter (e.g. BAR1 or FUS1), linked to an indicator gene (e.g. HIS3 or LacZ). The cells are placed in multi-titer plates, and different compounds are placed in each well. The colonies are then scored for expression of the indicator gene.

SUMMARY OF THE INVENTION

The present invention relates to novel, rapid, reliable and effective assays for screening and identifying pharmaceutically effective compounds that specifically interact with and modulate the activity of a cellular receptor or ion channel of a cell.

The present invention provides for the use of any type of cell in the subject assays, whether prokaryotic or eukaryotic. In preferred embodiments, the cells of the present invention are eukaryotic. In certain preferred embodiments the cells are mammalian cells. In other preferred embodiments the cells are yeast cells, with cells from the genera Saccharomyces or Schizosaccharomyces being more preferred. The host cells can be derived from primary cells, or transformed and/or immortalized cell lines.

The subject assays provide a means for detecting the ability of compounds to modulate the signal transduction activity of the target receptor by scoring for up or down-regulation of a detection signal. Signal trasduction can be measured in a variety of ways. For example, endogenous yeast second messenger generation (e.g., GTP hydrolysis, calcium mobilization, or phospholipid hydrolysis) or increased transcription of an endogenous gene can be detected directly. Alternatively, the use of a reporter or indicator gene can provide a convenient readout. By whatever means measured, a change (e.g., a statistically significant change) in the detection signal can be used to facilitate isolation of those cells from the mixture which have received a signal via the target receptor, and thus can be used to identify novel compounds which function as receptor agonists or antagonists.

In one embodiment of the present invention the reagent cells express the receptor of interest endogenously. In other embodiments, the cells are engineered to express a heterlogous receptor protein. In either of these embodiments, it may be desirable to inactivate one or more endogenous genes of the host cells. For example, certain preferred embodiments in which a heterologous receptor is provided utilize host cells in which the gene for the homologous receptor has been inactivated. Likewise, other proteins involved in transducing signals from the target receptor can be inactivated, or complemented with an ortholog or paralog from another organism, e.g., yeast G protein subunits can be complemented by mammalian G protein subunits in yeast cells also engineered to express a mammalian G protein coupled receptor. Other complementations include, for example, expression of heterologous MAP kinases or erk kinases, MEKs or MKKs (MAP kinase kinases), MEKKs (MEK kinases), ras, raf, STATs, JAKs and the like.

In one embodiment, the assay of the present invention can be used to screen compounds which are exogenously added to cells in order to identify potential receptor effector compounds. In another embodiment the subject assays enable rapid screening of large numbers of polypeptides in a library expressed in the cell in order to identify those polypeptides which agonize or antagonize receptor bioactivity, creating an autocrine system. The autocrine assay is characterized by the use of a library of recombinant cells, each cell of which includes a target receptor protein whose signal transduction activity can be modulated by interaction with an extracellular signal, the transduction activity being able to generate a detectable signal, and an expressible recombinant gene encoding an exogenous test polypeptide from a polypeptide library. By the use of a gene library, the mixture of cells collectively express a population of test polypeptides. In preferred embodiments, the polypeptide library includes at least $10^3$ different polypeptides, though more preferably at least $10^5$, $10^6$, or $10^7$ different (variegated) polypeptides. The polypeptide library can be generated as a random peptide library, as a semi-random peptide library (e.g., based on combinatorial mutagenesis of a known ligand), or as a cDNA library.

In another embodiment of the assay, if a test compound does not appear to directly induce the activity of the receptor protein, the assay may be repeated and modified by the introduction of a step in which the cell is first contacted with a known activator of the target receptor to induce the signal transduction pathways from the receptor. Thus, a test compound can be assayed for its ability to antagonize, e.g., inhibit or block the activity of the activator. Alternatively, the assay can score for compounds which potentiate the induction response generated by treatment of the cell with a known activator. As used herein, an "agonist" refers to agents which either induce activation of receptor signaling pathways, e.g., such as by mimicking a ligand for the receptor, as well as agents which potentiate the sensitivity of the receptor to a ligand, e.g., lower the concentrations of ligand required to induce a particular level of receptor-dependent signaling.

In one aspect, the invention pertains to an assay for identifying a compound that modulates a heterologous receptor expressed by a yeast cell. The subject assays comprise the steps of: (i) providing a yeast cell in which a heterologous receptor is functionally integrated into an endogenous yeast signaling pathway; (ii) contacting the yeast cell with a test compound; and (iii) detecting an alteration in a signal produced by the endogenous yeast signaling pathway.

In preferred embodiments, the signaling pathway is a yeast pheromone system pathway.

In other preferred embodiments, the step of detecting comprises measuring the transcription of a gene which encodes an endogenous yeast protein. The transcription of a gene can be measured directly or indirectly. In addition, in other embodiments, the amount or activity of an endogenous yeast protein can be assayed.

The compounds to be tested in the subject assays can be derived from a number of sources. In a preferred embodiment, the test compound is derived from a peptide library. In another preferred embodiment, the test compound is derived from a library of non-peptidic compounds.

In the embodiments of the subject assays in which the activity of an endogenous yeast protein is assayed, the endogenous yeast protein can be encoded by an endogenous yeast gene which is operatively linked to a promoter which is responsive to signals produced by a yeast pheromone system. In one embodiment, the promoter is naturally occurring. In yet another embodiment, the promoter is non-naturally occurring. Such non-naturally occurring promoters can be derived by modifying a naturally-occurring promoter, e.g., by mutating a naturally-occurring promoter. In yet other embodiments of the assay, the promoter is a heterologous promoter operatively linked to the endogeneous yeast gene.

In preferred embodiments, the endogenous yeast gene to be assayed is the BAR1 gene. In other preferred embodiments, the promoter which regulates expression of the endogenous yeast gene is a pheromone responsive promoter. Examples of preferred pheromone-responsive promoters include the Fus1 promoter and the Fus 2 promoter, which, in certain embodiments, are operatively linked to a heterologous endogenous gene.

In yet another embodiment, the subject assays utilize yeast cells which comprise a chimeric nucleic acid construct. This chimeric construct encodes a fusion protein that modulates the expression of an endogenous gene, wherein this expression is assayable. The chimeric constructs of the invention comprise a first segment derived from a first gene, which encodes a polypeptide that is activated by the yeast pheromone system pathway, and a second segment which encodes a polypeptide that binds a DNA sequence in the regulatory region of an endogenous gene of interest. Such constructs render the gene of interest responsive to activation by the yeast pheromone system pathway.

In preferred embodiments, the first segment of such a construct encodes Ste12. In other preferred embodiments, the second segment encodes Pho4 (or a DNA binding domain thereof). In yet another preferred embodiment, the endogenous yeast gene to be assayed is a Pho5 gene (which contains a Pho4 binding site within its regulatory region). Thus, upon expression of the Ste12-Pho4 fusion protein (whose expression is pheromone responsive), the fusion protein binds to the Pho4 site in the Pho5 gene, thereby activating expression of the Pho5 gene. The Pho5 gene encodes an acid phosphatase whose expression is readily assayable. In a particularly preferred embodiment, the first segment of the chimeric construct encodes a polypeptide comprising amino acids 1–688 of Ste 12. In another particularly preferred embodiment, the second segment encodes a polypeptide comprising amino acids 227–312 of Pho4. In yet another preferred embodiment, the yeast cell to be used in the assay also comprises a mutation in its endogenous Pho4 gene. In a preferred embodiment, the detecting step of an assay of the present invention comprises detecting the activity of PHO5 acid phosphatase.

In yet another embodiment of the subject assays, the detecting step comprises detecting a change in the activity of an endogenous enzyme expressed by said yeast cell in response to a signal produced by the endogenous yeast signaling pathway. Preferably, the endogenous yeast signaling pathway is a yeast pheromone system pathway. A change in the activity of an endogenous enzyme can be detected by, for example, measuring the enzymatic activity of the enzyme. In a preferred embodiment, the assay comprises detecting the activity of BAR1 protease.

The activity of BAR1 protease can be detected in a variety of ways. For example, the cleavage of a substrate having a BAR1 peptide recognition sequence can be monitored. In a preferred embodiment, the BAR1 substrate comprises at least one detectable label. In one embodiment, the substrate is naturally occurring. In yet another embodiment, the substrate is not naturally occurring. In a preferred embodiment, the substrate comprises the compound of SEQ ID NO:4. In yet another preferred embodiment the substrate comprises the compound of SEQ ID NO:5.

In still another embodiment, the substrate is a chimeric substrate comprising a first polypeptide which, upon cleavage by BAR1, exposes an amino terminal Lys; and a second polypeptide linked to the carboxy terminus of said first polypeptide. In a particularly preferred embodiment the step of detecting comprises measuring the stability of the chimeric substrate.

BAR1 activity also can be detected by measuring the effect of the enzyme on the growth of a test yeast strain which does not express a functional BAR1 enzyme. Thus, medium from BAR1-expressing cells that have been contacted with a test compound can be cultured with the test yeast strain to thereby detect the presence of BAR1 activity in the medium.

In another aspect, the invention provides an assay for identifying a compound that modulates a receptor in a cell comprising the steps of (i) providing a cell which expresses a receptor which is functionally integrated into an endogenous signaling pathway of the cell; (ii) contacting the cell with a library of non-peptidic compounds; and (iii) detecting an alteration in a signal produced by the endogenous signaling pathway. In a preferred embodiment, the cell is a yeast cell. In yet another preferred embodiment, the signaling pathway is a yeast pheromone system pathway. The step of measuring can comprise, for example, measuring the transcription of an endogenous gene or the activity of an endogenous protein in the cell.

In another aspect, the invention provides an assay for identifying a compound that modulates a receptor in a cell comprising the steps of (i) providing a cell which expresses a receptor which is functionally integrated into an endogenous signaling pathway of the cell; (ii) contacting the cell with a library of test polypeptides, wherein said library of test polypeptides is expressed by the cell; and (iii) detecting an alteration in a signal produced by the endogenous signaling pathway. In a preferred embodiment, the cell is a yeast cell. In yet another preferred embodiment, the signaling pathway is a yeast pheromone system pathway. The step of measuring can comprise, for example, measuring the transcription of an endogenous gene or the activity of an endogenous protein in the cell.

In yet another aspect the invention provides an assay for identifying a compound that modulates a pheromone system protein surrogate in a yeast cell comprising the steps of: (i) providing a yeast cell which comprises a pheromone system protein surrogate which is functionally integrated into an endogenous pheromone system signaling pathway of the yeast cell; (ii) contacting the cell with a library of non-peptidic compounds; and (iii) measuring an alteration in a signal produced by the endogenous pheromone signaling pathway of the yeast cell.

In a preferred embodiment, the step of measuring comprises measuring the transcription of an endogenous gene or the activity of an endogenous protein in the cell. In a preferred embodiment, the pheromone system protein surrogate to be assayed is selected from the group consisting of G protein-coupled receptors, G proteins, proteases, kinases, farnesyltransferases, carboxymethyltransferases, ABC transporters and cyclins.

In another aspect, the invention provides an assay for identifying a compound that modulates a pheromone system protein surrogate in a yeast cell comprising the steps of: (i) providing a yeast cell which comprises a pheromone system protein surrogate which is functionally integrated into an endogenous pheromone system signaling pathway of the yeast cell; (ii) contacting the cell with a library of test polypeptides, wherein said library of test polypeptides is expressed by the cell; and (iii) measuring an alteration in a signal produced by the endogenous pheromone signaling pathway of the yeast cell.

In a preferred embodiment, the step of measuring comprises measuring the transcription of an endogenous gene or the activity of an endogenous protein in the cell. In a preferred embodiment, the pheromone system protein surrogate to be assayed is selected from the group consisting of G protein-coupled receptors, G proteins, proteases, kinases, farnesyltransferases, carboxymethyltransferases, ABC transporters and cyclins.

The invention also provides substrates for a BAR1 enzyme. In preferred embodiments, the substrate comprises the compound of SEQ ID NO: 4 or SEQ ID NO:5.

The invention also provides a chimeric substrate for a BAR1 enzyme, the chimeric substrate comprising: a first polypeptide segment derived from mature yeast α-factor and a second polypeptide segment derived from a second, different polypeptide, wherein upon cleavage of said first polypeptide segment by BAR1 a change in the stability of said second polypeptide segment is detectable.

In preferred embodiments, the second polypeptide segment is derived from LacZ. In yet another preferred embodiment, the second polypeptide segment is derived from a protein which is essential for yeast cell growth. In yet another preferred embodiment the second polypeptide segment is derived from a yeast repressor protein.

In another aspect the invention provides a chimeric nucleic acid construct comprising: a first segment comprising an nucleotide sequence encoding a polypeptide which is activated by a yeast pheromone system pathway; and a second segment comprising a nucleotide sequence encoding a Pho4 polypeptide. In a preferred embodiment the first segment encodes a Ste12 polypeptide.

The invention also provides a yeast cell which comprises a chimeric nucleic acid construct of the invention.

Receptor proteins for use in the present invention can be any receptor or ion channel which interacts with an extracellular molecule (i.e. hormone, growth factor, peptide, ion) to modulate a signal in the cell. To illustrate the receptor can be a cell surface receptor, or in other embodiments can be an intracellular receptor. In preferred embodiments, the receptor is a cell surface receptor, such as: a receptor tyrosine kinase, e.g., an EPH receptor; an ion channel; a cytokine receptor; an multisubunit immune recognition receptor, a chemokine receptor; a growth factor receptor, or a G-protein coupled receptor, such as a chemoattracttractant peptide receptor, a neuropeptide receptor, a light receptor, a neurotransmitter receptor, or a polypeptide hormone receptor.

Preferred G protein coupled receptors include: α1A-adrenergic receptor, α1B-adrenergic receptor, α2-adrenergic receptor, α2B-adrenergic receptor, α1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor.

Preferred EPH receptors include eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors.

In addition, the subject assay can be used to identifying ligands for an orphan receptor, i.e., a receptor with no known ligand, regardless of the class of receptors to which it belongs.

In those embodiments wherein the target receptor is a cell surface receptor, and the cell expresses a peptide library, in certain embodiments, it will be desirable for the peptides in the library to express a signal sequence to ensure that they are processed in the appropriate secretory pathway and thus are available to interact with receptors on the cell surface.

In other embodiments, the host cell harbors a reporter construct containing a reporter gene in operative linkage with one or more transcriptional regulatory elements responsive to the signal transductin activity of the receptor protein. Exemplary reporter genes include enzymes, such as luciferase, phosphatase, or β-galactosidase which can produce a spectrometrically active label, e.g., changes in color, fluorescence or luminescence, or a gene product which alters a cellular phenotype, e.g., cell growth, drug resistance or auxotrophy. In preferred embodiments: the reporter gene encodes a gene product selected from the group consisting of chloramphenicol acetyl transferase, beta-galactosidase and secreted alkaline phosphatase. In still other embodiments, the reporter gene encodes a gene product which confers a growth signal. In yet other embodiments, the reporter gene encodes a gene product for growth in media containing aminotriazole or canavanine or cycloheximide.

BRIEF DESCRIPTION OF THE FIGURES

The FIGURE is a sequence alignment of N-terminal regions of Gα subunits and N-terminal sequences of GPA41-Gα hybrid proteins.

DETAILED DESCRIPTION OF THE INVENTION

Proliferation, differentiation and death of eukaryotic cells are controlled by a variety of extracellular signals, such as hormones, neurotransmitters, and polypeptide factors. These diffusible ligands allow cells to influence and be influenced by environmental cues. The study of receptor-ligand interaction has revealed a great deal of information about how cells respond to external stimuli, and this knowledge has led to the development of therapeutically important compounds.

The present invention makes available a rapid, effective assay for screening and identifying pharmaceutically effective compounds that specifically interact with and modulate the activity of a cellular receptor or ion channel. The subject assay enables rapid screening of large numbers of compounds (including, for example, polypeptides in an expression library) to identifying compounds which induce or antagonize receptor bioactivity.

In general, the assay is characterized by the use of a mixture of cells to sample a battery of compounds for receptor/channel agonists or antagonists. As described with greater detail below, the reagent cells express a target receptor protein or ion channel capable of transducing a detectable signal in the reagent cell. The receptor/channel protein can be either endogenous or heterologous. In combination with the disclosed detection means, a culture of the instant reagent cells will provide means for detecting agonists or antagonists of receptor function.

In certain embodiments, a test compound is exogenously added, and its ability to modulate the activity of the target receptor or ion channel is scored in the assay. In other embodiments, the cells are engineered to additionally express a test polypeptide which can be assayed for its ability to interact with the receptor or ion channel. In those embodiments, the assay provides a population of cells which express a library peptides which include potential receptor/channel effectors, and those peptides of the library which either agonize or antagonize the receptor or channel function can be selected and identified by sequence.

The assay of the present invention provides a convenient format for discovering drugs which can be useful to modulate cellular function, as well as to understand the pharmacology of compounds that specifically interact with cellular receptors or ion channels. Moreover, the subject assay is particularly amenable to identifying ligands, natural or artificial, for receptors and ion channels.

I. Definitions

Before further description of the invention, certain terms employed in the specification, examples and appended claims are, for convenience, collected here.

As used herein, "heterologous DNA" or "heterologous nucleic acid" includes DNA that does not occur naturally as part of the genome in which it is present or which is found in a location or locations in the genome that differs from that in which it occurs in nature. Heterologous DNA is not naturally occurring in that position or is not endogenous to the cell into which it is introduced, but has been obtained from another cell. Generally, although not necessarily, such DNA encodes proteins that are not normally produced by the cell in which it is expressed. Heterologous DNA can be from the same species, although in preferred embodiments, it is from a different species. In particularly preferred embodiments, it is mammalian, e.g., human. Heterologous DNA may also be referred to as foreign DNA. Any DNA that one of skill in the art would recognize or consider as heterologous or foreign to the cell in which is expressed is herein encompassed by the term heterologous DNA. Examples of heterologous DNA include, but are not limited to, DNA that encodes test polypeptides, receptors, reporter genes, transcriptional and translational regulatory sequences, or selectable or traceable marker proteins, such as a protein that confers drug resistance.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express the reporter gene construct, heterologous receptor or test polypeptide.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes. A "heterologous receptor" is a specific embodiment of a "heterologous protein", wherein the heterologous receptor is encoded by heterologous DNA and, upon expression of this heterologous DNA in a recombinant cell, the heterologous receptor is expressed in the recombinant cell.

As used herein, the term "extracellular signal" is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation. A "signaling pathway" refers to the components involved in "signal transduction" of a particular signal into a cell. The term "endogenous signaling pathway" indicates that some or all of the components of the signaling pathway are naturally-occurring components of the cell. An example of such a pathway is the endogenous pheromone system pathway of yeast.

The term "functionally integrated" (as in a receptor that is "functionally integrated into a signaling pathway in a cell" or "functionally integrated into an endogenous yeast signaling pathway") is intended to refer to the ability of the receptor to be expressed at the surface of the cell and the ability of the expressed receptor to bind to modulators (e.g., a ligand of the receptor) and transduce signals into the cell via components of a signaling pathway of the cell. For example, a G protein coupled receptor (GPCR) which is functionally integrated into an endogenous pheromone response pathway of a yeast cell is expressed on the surface of the yeast cell, couples to a G protein of the pheromone response pathway within the yeast cell and transduces a signal in that yeast cell upon binding of a modulator to the receptor.

The term "endogenous gene" is intended to refer to a gene in a cell that is naturally part of the genome of the cell and which, most preferably, is present in its natural location in the genome (as opposed to "heterologous" DNA which has been introduced into the cell). Likewise, the term "endogenous protein" is intended to include proteins of a cell that are encoded by endogenous genes of the cell.

An endogenous gene may comprise the natural regulatory elements of the gene (e.g.,. the native promoter/enhancer elements that naturally regulate expression of the gene) or the endogenous gene can be "operatively linked to" (i.e., functionally coupled to) a "heterologous promoter" (or other heterologous regulatory elements). A "heterologous promoter" refers to a promoter that does not naturally regulate the gene to which the heterologous promoter is operatively linked. For example, an endogenous yeast gene that is not normally pheromone-responsive can be operatively linked to a heterologous promoter that is responsive to signals produced by the yeast pheromone system to thereby confer pheromone responsiveness on the endogenous yeast gene (described in further detail below).

The term "detecting an alteration in a signal produced by an endogenous signaling pathway" (e.g., an endogenous yeast signaling pathway) is intended to encompass the detection of alterations in endogenous second messengers produced upon activation of components of the endogenous signaling pathway, alterations in endogenous gene transcription induced upon activation of components of the endogenous signaling pathway, and/or alterations in the activity of an endogenous protein(s) upon activation of components of the endogenous signaling pathway. The term "detecting an alteration in a signal produced by an endogenous signaling pathway is not, however, intended to encompass detecting alterations in the level of expression of an exogenous reporter gene that has been introduced into the cell or the activity of the reporter gene product. Moreover, the term "detecting an alteration in a signal produced by an endogenous signaling pathway" is not intended to encompass assaying general, global changes to the cell such as changes in cell growth or cell morphology. Rather, this term indicates that a specific signal associated with the endogenous signaling pathway is assayed.

The term "modulation", as in "modulation of a (heterologous) receptor" and "modulation of a signal transduction activity of a receptor protein" is intended to encompass, in its various grammatical forms, induction and/or potentiation, as well as inhibition and/or downregulation of receptor activity and/or one or more signal transduction pathways downstream of a receptor.

The term "compound" as used herein (e.g., as in "test compound") is meant to include both exogenously added test compounds and peptides endogenously expressed from a peptide library. For example, in certain embodiments, the reagent cell also produces the test compound which is being screened. For instance, the reagent cell can produce. e.g., a test polypeptide, a test nucleic acid and/or a test carbohydrate which is screened for its ability to modulate the receptor/channel activity. In such embodiments, a culture of such reagent cells will collectively provide a library of potential effector molecules and those members of the library which either agonize or antagonize the receptor or ion channel function can be selected and identified. Moreover, it will be apparent that the reagent cell can be used to detect agents which transduce a signal via the receptor or channel of interest.

In other embodiments, the test compound is exogenously added. In such embodiments the test compound is contacted with the reagent cell. Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino lo acids, modified peptide backbones and the like, as well as compounds that are composed, in whole or in part, of molecular structures unrelated to naturally-occurring L-amino acid residues linked by natural peptide bonds. "Non-peptidic compounds" also are intended to include natural products.

The term "chimeric nucleic acid construct" is intended to refer to a nucleic acid molecule, preferably DNA, composed of at least two discrete segments, a first segment derived from a first gene and a second segment derived from a second gene. The term "derived from" is intended to indicate that the first and second segments have the same or a substantially homologous nucleotide sequence as all or a part of the first and second genes, respectively. Each of the first and second segments encodes a functional polypeptide and are operatively linked such that upon expression of the construct, a fusion protein is produced, the fusion protein comprising a first polypeptide encoded by the first segment and a second polypeptide encoded by the second segment. In a preferred embodiment, the first segment of the chimeric construct encodes a yeast transcription factor that is responsive to signals transduced via the pheromone system pathway and the second segment encodes a DNA binding protein that binds to a DNA sequence in the regulatory region of an endogenous gene of interest.

A "chimeric substrate" (as in a "chimeric substrate of a BAR1 enzyme) is intended to refer to a substrate composed of two distinct polypeptides, linked to each other, wherein at least one of the polypeptides is cleavable by BAR1. Preferably the first polypeptide of the chimeric substrates exposes an N-terminal lysine residue upon cleavage by BAR1 and the second polypeptide is linked to the C-terminus of the first polypeptide. In a preferred embodiment, the first polypeptide is a yeast a-factor polypeptide.

The term "pheromone system protein surrogate" (abbreviated as "PSP surrogate") is intended to refer to a heterologous protein in a yeast cell which is functionally homologous to a yeast protein of the pheromone system pathway (i.e.,. the PSP surrogate is functionally integrated into the yeast pheromone system pathway). Examples of PSP surrogates, and methods of preparing yeast cells comprising such PSP surrogates are described in detail in PCT Publication WO 94/23025. Preferred PSP surrogates include G protein-coupled receptors, G proteins, proteases, kinases, farnesyltransferases, carboxymethyltransferases, ABC transporters and cyclins.

The term "receptor effector" is intended to include agonists and antagonists that modulate signal transduction via a receptor. Receptor effector molecules are capable of binding to the receptor, though not necessarily at the binding site of the natural ligand. Receptor effectors can modulate signal transduction when used alone, i.e. can be surrogate ligands, or can alter signal transduction in the presence of the natural ligand, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The terms "receptor activator" and "surrogate ligand" refer to an agonist which induces signal transduction from a receptor.

"Orphan receptors" is a designation given to a receptors for which no specific natural ligand has been described and/or for which no function has been determined.

The term "indicator gene" generically refers to an expressible (e.g., able to transcribed and (optionally) translated) DNA sequence which is expressed in response to a signal transduction pathway modulated by a target receptor or ion channel. Exemplary indicator genes include unmodified endogenous genes of the host cell, modified endogenous genes, or a reporter gene of a heterologous construct, e.g., as part of a reporter gene construct.

As used herein, a "reporter gene construct" is a nucleic acid that includes a "reporter gene" operatively linked to at least one transcriptional regulatory sequence.

Transcription of the reporter gene is controlled by these sequences to which they are linked. The activity of at least one or more of these control sequences is directly or indirectly regulated by the target receptor protein. Exemplary transcriptional control sequences are promoter sequences. A reporter gene is meant to include a promoter-reporter gene construct which is heterologously expressed in a cell.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

The term "autocrine cell", as used herein, refers to a cell which produces a substance which can stimulate a receptor located on or within the same cell as that which produces the substance. For example, wild-type yeast MATa and MATα cells are not autocrine. However, a yeast cell which produces both a-factor and a-factor receptor, or both α-factor and α-factor receptor, in functional form, is autocrine. By extension, cells which produce a peptide which is being screened for the ability to activate a receptor (e.g., by activating a G protein-coupled receptor) and also express the receptor are called "autocrine cells". In some instances, such cells can also be referred to as "putative autocrine cells" since some of the cells will express peptides from the library which will not activate the receptor which is expressed. In a library of such cells, in which a multitude of different peptides are produced, it is likely that one or more of the cells will be "autocrine" in the stricter sense of the term.

II. General Overview of Assay

As set out above, the present invention relates to methods for identifying effectors of a receptor protein or complex thereof. In general, the assay is characterized by the use of a test cell which includes a target receptor or ion channel protein whose signal transduction activity can be modulated by interaction with an extracellular signal, the transduction activity being able to generate a detectable signal. In preferred embodiments, the cell also includes a detection means, such as a reporter gene or an indicator gene, for detecting signals produced by the receptor. In the most preferred embodiments of the invention, an alteration in a signal produced by an endogenous signaling pathway of the cell is detected.

The ability of particular compounds to modulate a signal transduction activity of target receptor or channel can be scored for by detecting up or down-regulation of an endogenous detection signal. For example, second messenger generation (e.g. GTPase activity, phospholipid hydrolysis, or protein phosphorylation patterns as examples) can be measured directly. In other embodiments, transcription of an endogenous gene or activity of an endogenous protein is used as a detectabel readout.

Alternatively, the use of an indicator gene can provide a convenient readout. In other embodiments a detection means consists of a reporter gene. In any event, a statistically significant change in the detection signal can be used to facilitate identification of compounds which modulate receptor or ion channel activities.

By this method, compounds which induce a signal pathway from a particular receptor or channel can be identified. If a test compound does not appear to induce the activity of the receptor/channel protein, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

In developing the subject assays, it was recognized that a frequent result of receptor-mediated responses to extracellular signals was the transcriptional activation or inactivation of specific genes after exposure of the cognate receptor to an extracellular signal that induces such activity. Thus, transcription of genes controlled by receptor-responsive transcriptional elements often reflects the activity of the surface protein by virtue of transduction of an intracellular signal. To illustrate, the intracellular signal that is transduced can be initiated by the specific interaction of an extracellular signal, particularly a ligand, with a cell surface receptor on the cell. This interaction sets in motion a cascade of intracellular events, the ultimate consequence of which is a rapid and detectable change in the transcription or translation of a gene. By selecting transcriptional regulatory sequences that are responsive to the transduced intracellular signals and operatively linking the selected promoters to indicator genes, whose transcription or translation is readily detectable and measurable, a transcription based assay provides a rapid indication of whether a specific receptor or ion channel interacts with a test compound in any way that modulates intracellular transduction. Expression of the indicator gene, thus, provides a valuable screening tool for the development of compounds that act as agonists or antagonists of a cell receptor or ion channel.

Indicator or reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on receptor signaling. Typically, the reporter gene construct will include a reporter gene in operative linkage with one or more transcriptional regulatory elements responsive to the signal transduction activity of the target receptor, with the level of expression of the reporter gene providing the receptor-dependent detection signal. As described below, certain endogenous genes can provide a detectable signal in response to a signal transduction from a receptor or ion channel, i.e., act as indicator genes. In either embodiment, the amount of transcription from the indicator gene may be measured using any method known to those of skill in the art to be suitable. For example, specific mRNA expression may be detected using Northern blots or specific protein product may be identified by a characteristic stain or an intrinsic activity.

In preferred embodiments, the gene product of the indicator or reporter gene is detected by an intrinsic activity associated with that product. For instance, the indicator gene may encode a gene product that, e.g., by enzymatic activity, gives rise to a detection signal based on, for example, color, fluorescence, or luminescence.

The amount of expression from the indicator gene is then compared to the amount of expression in either the same cell in the absence of the test compound or it may be compared with the amount of transcription in a substantially identical cell that lacks the specific receptors. A control cell may be derived from the same cells from which the test cell was prepared but which had not been treated with the compound. Alternatively, it may be a cell in which the receptor of interest are removed. Any statistically or otherwise significant difference in the amount of transcription indicates that the test compound has in some manner altered the activity of the specific receptor or ion channel.

In other preferred embodiments, the indicator gene provides a selection method such that cells in which activation (or inactivation) of one or more signal pathways of a receptor or ion channel provides a growth advantage to the treated cell. For example, expression of the indicator gene could enhance cell viability, relieve a cell nutritional requirement, and/or provide resistance to a drug.

In other embodiments, changes in intracellular second messenger pathways can be detected biochemically rather than biologically. For example, changes in intracellular $Ca^{+2}$, phophorylation states of proteins, activities of intracellular enzymes, and the like can be detected. Still other detection techniques include micorphysiometric devices which permit detection of small changes in, e.g., ions or intracellular pH.

With respect to the receptor or ion channel, it may be endogenously expressed by the host cell, or it may be expressed from a heterologous gene that has been introduced into the cell. Methods for introducing heterologous DNA into eukaryotic cells are well known in the art and any such method may be used. In addition, DNA encoding various receptor proteins is known to those of skill in the art or it may be cloned by any method known to those of skill in the art. In certain embodiments, such as when an exogenous receptor is expressed, it may be desirable to inactivate, such as by deletion, a homologous receptor present in the cell.

The subject assay is useful for identifying compounds that interact with any receptor protein whose activity ultimately induces a signal transduction cascade in the host cell which can be exploited to produce a detectable signal. In particular, the assays can be used to test functional ligand-receptor or ligand-ion channel interactions for cell surface-localized receptors and channels, and also for cytoplasmic and nuclear receptors. As described in more detail below, the subject assay can be used to identify effectors of, for example, G protein-coupled receptors, receptor tyrosine kinases, cytokine receptors, and ion channels, as well as steroid hormone, or other nuclear receptors. In certain embodiments the method described herein is used for identifying ligands for "orphan receptors" for which no ligand is known.

In embodiments utilizing an "autocrine cell" of the present invention, and in which cell surface receptors are the assay targets, it will be desirable for each of the peptides of the peptide library to include a signal sequence for secretion. In certain embodiments the expression of such a signal sequence may ensure appropriate transport of the peptide to the endoplasmic reticulum, the golgi, and ultimately to the cell surface. When a yeast cell is the host cell, in certain embodiments, the signal sequence will transport peptides to the periplasmic space, however, such transport may not be necessary to achieve autocrine stimulation.

Any transfectable cell that can express the desired cell surface protein in a manner such the protein functions to intracellularly transduce an extracellular signal may be used. Similarly, any cell surface protein that is known to those of skill in the art or that may be identified by those of skill in the art may used in the assay. The cell surface protein may endogenously expressed on the selected cell or it may be expressed from cloned DNA.

III. Host Cells

Suitable host cells for generating the subject assay include prokaryotes, yeast, or higher eukaryotic cells, including plant and animal cells, especially mammalian cells. Prokaryotes include gram negative or gram positive organisms. Examples of suitable mammalian host cell lines include the COS-7 line of monkey kidney cells (ATCC CRL 1651) (Gluzman (1981) Cell 23:175) CV-1 cells (ATCC CCL 70), L cells, C127, 3T3, Chinese hamster ovary (CHO), HeLa, HEK-293, SWISS 3T3, and BHK cell lines.

If yeast cells are used, the yeast may be of any species which are cultivable and in which an exogenous receptor can be made to engage the appropriate signal transduction machinery of the host cell. Suitable species include *Kluyverei lactis, Schizosaccharomyces pombe,* and *Ustilaqo maydis; Saccharomyces cerevisiae* is preferred. Other yeast which can be used in practicing the present invention are *Neurospora crassa, Aspergillus niger, Aspergillus nidulans, Pichia pastoris, Candida tropicalis,* and *Hansenula polymorpha.* The term "yeast", as used herein, includes not only yeast in a strictly taxonomic sense, i.e., unicellular organisms, but also yeast-like multicellular fungi or filamentous fungi.

The choice of appropriate host cell will also be influenced by the choice of detection signal. For instance, reporter constructs, as described below, can provide a selectable or screenable trait upon transcriptional activation (or inactivation) in response to a signal transduction pathway coupled to the target receptor. The reporter gene may be an unmodified gene already in the host cell pathway, such as the genes responsible for growth arrest in yeast. It may be a host cell gene that has been operably linked to a "receptor-responsive" promoter. Alternatively, it may be a heterologous gene (e.g., a "reporter gene construct") that has been so linked. Suitable genes and promoters are discussed below. In other embodiments, second messenger generation can be measured directly in the detection step, such as mobilization of intracellular calcium or phospholipid metabolism are quantitated. In yet other embodiments indicator genes can be used to detect receptor-mediated signaling.

Accordingly, it will be understood that to achieve selection or screening, the host cell must have an appropriate phenotype. For example, generating a pheromone-responsive chimeric HIS3 gene in a yeast that has a wild-type HIS3 gene would frustrate genetic selection. Thus, to achieve nutritional selection, an auxotrophic strain is preferred.

A variety of complementations for use in the subject assay can be constructed. Indeed, many yeast genetic complementation with mammalian signal transduction proteins have been described in the art. For example, Mosteller et al. (1994) Mol Cell Biol 14:1104–12 demonstrates that human Ras proteins can complement loss of ras mutations in *S. cerevisiae.* Moreover, Toda et al. (1986) Princess Takamatsu Symp 17:253–60 have shown that human ras proteins can complement the loss of RAS1 and RAS2 proteins in yeast, and hence are functionally homologous. Both human and yeast RAS proteins can stimulate the magnesium and guanine nucleotide-dependent adenylate cyclase activity present in yeast membranes. Ballester et al. (1989) Cell 59:681–6 describe a vector to express the mammalian GAP protein in the yeast *S. cerevisiae.* When expressed in yeast, GAP inhibits the function of the human ras protein, and complements the loss of IRA1. IRA1 is a yeast gene that encodes a protein with homology to GAP and acts upstream of RAS. Mammalian GAP can therefore function in yeast and interact with yeast RAS. Wei et al. (1994) Gene 151:279–84 describes that a human Ras-specific guanine nucleotide-exchange factor, Cdc25GEF, can complement the loss of CDC25 function in *S. cerevisiae.* Martegani et al. (1992) EMBO J 11:2151–7 describe the cloning by functional complementation of a mouse cDNA encoding a homolog of CDC25, a *Saccharomyces cerevisiae* RAS activator. Vojtek et al. (1993) J Cell Sci 105:777–85 and Matviw et al. (1992) Mol Cell Biol 12:5033–40 describe how a mouse CAP protein, e.g., an adenylyl cyclase associated protein associated with ras-mediated signal transduction, can complements defects in *S. cerevisiae.* Papasavvas et al. (1992) Biochem Biophys Res Commun 184:1378–85 also suggest that inactivated yeast adenyl cyclase can be complemented by a mammalian adenyl cyclase gene. Hughes et al. (1993) Nature 364:349–52 describe the complementation of byr1 in fission yeast by mammalian MAP kinase kinase (MEK). Parissenti et al. (1993) Mol Cell Endocrinol 98:9–16 describes the reconstitution of bovine protein kinase C (PKC) in yeast. The Ca(2+)- and phospholipid-dependent Ser/Thr kinase PKC plays important roles in the transduction of cellular signals in mammalian cells. Marcus et al. (1995) PNAS 92:6180–4 suggests the complementation of shk1 null mutations in *S. pombe* by the either the structurally related *S. cerevisiae* Ste20 or mammalian p65PAK protein kinases.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of inactivated gene of the host cell is supplied by an exogenous nucleic acid. For instance, yeast cells can be "mammalianized", and even "humanized", by complementation of receptor and signal transduction proteins with mammalian homologs. To illustrate, inactivation of a yeast Byr2/Ste11 gene can be complemented by expression of a human MEKK gene.

IV. Expression Systems

Ligating a polynucleotide coding sequence into a gene construct, such as an expression vector, and transforming or transfecting into hosts, either eukaryotic (yeast, avian, insect or mammalian) or prokaryotic (bacterial cells), are standard procedures used in producing other well-known proteins, including sequences encoding exogenous receptor and peptide libraries. Similar procedures, or modifications thereof, can be employed to prepare recombinant reagent cells of the present invention by tissue-culture technology in accord with the subject invention.

In general, it will be desirable that the vector be capable of replication in the host cell. It may be a DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, New York, 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

Preferred mammalian expression vectors contain both prokaryotic sequences, to facilitate the propagation of the vector in bacteria, and one or more eukaryotic transcription units that are expressed in eukaryotic cells. The pcDNAI/ amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells.

Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

Transcriptional and translational control sequences in expression vectors to be used in transforming mammalian cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al.(1978) *Nature* 273:111) Smaller or larger SV40 fragments may also be used, provided the approximately 250 bp sequence extending from the Hind III site toward the Bgl I site located in the viral origin of replication is included. Exemplary vectors can be constructed as disclosed by Okayama and Berg (1983, *Mol. Cell Biol.* 3:280). A useful system for stable high level expression of mammalian receptor cDNAs in C127 murine mammary epithelial cells can be constructed substantially as described by Cosman et al (1986, *Mol. Immunol.* 23:935). Other expression vectors for use in mammalian host cells are derived from retroviruses.

In other embodiments, the use of viral transfection can provide stably integrated copies of the expression construct. In particular, the use of retroviral, adenoviral or adeno-associated viral vectors is contemplated as a means for providing a stably transfected cell line which expresses an exogenous receptor, and/or a polypeptide library.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. Moreover, if yeast are used as a host cell, it will be understood that the expression of a gene in a yeast cell requires a promoter which is functional in yeast. Suitable promoters include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R.

Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

In some instances, it may be desirable to use insect cells ase the host cells. In such embodiments, recombinant polypeptides can be expressed by the use of a baculovirus expression system. Examples of such baculovirus expression systems include pVL-derived vectors (such as pVL1392, pVL 1393 and pVL941), pAcUW-derived vectors (such as pAcUW1), and pBlueBac-derived vectors (such as the β-gal containing pBlueBac III).

In constructing suitable expression plasmids, the termination sequences associated with these genes, or with other genes which are efficiently expressed in yeast, may also be ligated into the expression vector 3' of the heterologous coding sequences to provide polyadenylation and termination of the mRNA.

V. Periplasmic Secretion

In embodiments in which yeast cells are used as the host cell and the compounds tested are endogenously expressed from a library, it will be noted that the yeast cell is bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diff-use through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion, or, if such secretion is provided, any particular secretion signal or transport pathway.

VI. Receptors

Cytokine Receptors

In one embodiment the target receptor is a cytokine receptor. Cytokines are a family of soluble mediators of cell-to-cell communication that includes interleukins, interferons, and colony-stimulating factors. The characteristic features of cytokines lie in their functional redundancy and pleiotropy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily acitvate the Jak protein tyrosine kinase family, with resultant phosphorylation of the STAT transcriptional activator factors. IL-2, IL-7, IL-2 and Interferon γ have all been shown to activate Jak kinases (Frank et al (1995) *Proc Natl Acad Sci USA* 92:7779–7783); Scharfe et al. (1995) *Blood* 86:2077–2085); (Bacon et al. (1995) *Proc Natl Acad Sci USA* 92:7307–7311); and (Sakatsume et al (1995) *J. Biol Chem* 270:17528–17534). Events downstream of Jak phosphorylation have also been elucidated. For example, exposure of T lymphocytes to IL-2 has been shown to lead to the phosphorylation of signal transducers and activators of transcription (STAT) proteins STAT1α, STAT2β, and STAT3, as well as of two STAT-related proteins, p94 and p95. The STAT proteins were found to translocate to the nucleus and to bind to a specific DNA sequence, thus suggesting a mechanism by which IL-2 may activate specific genes involved in immune cell function (Frank et al. supra). Jak3 is associated with the gamma chain of the IL-2, IL-4, and IL-7 cytokine receptors (Fujii et al. (1995) *Proc Natl Acad Sci* 92:5482–5486) and (Musso et al (1995) J Exp Med. 181:1425–1431). The Jak kinases have also been shown to be activated by numerous ligands that signal via cytokine receptors such as, growth hormone and erythropoietin and IL-6 (Kishimoto (1994) Stem cells Suppl 12:37–44).

Signal transduction which may be detected in the instant assays, in addition to direct detection of second messengers, (e.g., by measuring changes in phosphorylation) includes reporter constructs or indicator genes which include transcriptional regulatory elements responsive to the STAT proteins. Described infra.

Multisubunit Immune Recognition Receptor (MIRR)

In another embodiment the receptor is a multisubunit receptor. Receptors can be comprised of multiple proteins referred to as subunits, one category of which is referred to as a multisubunit receptor is a multisubunit immune recognition receptor (MIRR). MIRRs include receptors having multiple noncovalently associated subunits and are capable of interacting with src-family tyrosine kinases. MIRRs can include, but are not limited to, B cell antigen receptors, T cell antigen receptors, Fc receptors and CD22. One example of an MIRR is an antigen receptor on the surface of a B cell. To further illustrate, the MIRR on the surface of a B cell comprises membrane-bound immunoglobulin (mIg) associated with the subunits Ig-α and Ig-β or Ig-γ, which forms a complex capable of regulating B cell function when bound by antigen. An antigen receptor can be functionally linked to an amplifier molecule in a manner such that the amplifier molecule is capable of regulating gene transcription.

Src-family tyrosine kinases are enzymes capable of phosphorylating tyrosine residues of a target molecule. Typically, a src-family tyrosine kinase contains one or more binding domains and a kinase domain. A binding domain of a src-family tyrosine kinase is capable of binding to a target molecule and a kinase domain is capable of phosphorylating a target molecule bound to the kinase. Members of the src family of tyrosine kinases are characterized by an N-terminal unique region followed by three regions that contain different degrees of homology among all the members of the family. These three regions are referred to as src homology region 1 (SH1), src homology region 2 (SH2) and src homology region 3 (SH3). Both the SH2 and SH3 domains are believed to have protein association functions important for the formation of signal transduction complexes. The amino acid sequence of an N-terminal unique region, varies between each src-family tyrosine kinase. An N-terminal unique region can be at least about the first 40 amino acid residues of the N-terminal of a src-family tyrosine kinase.

Syk-family kinases are enzymes capable of phosphorylating tyrosine residues of a target molecule. Typically, a syk-family kinase contains one or more binding domains and a kinase domain. A binding domain of a syk-family tyrosine kinase is capable of binding to a target molecule and a kinase domain is capable of phosphorylating a target molecule bound to the kinase. Members of the syk- family of tyrosine kinases are characterized by two SH2 domains for protein association function and a tyrosine kinase domain.

A primary target molecule is capable of further extending a signal transduction pathway by modifying a second messenger molecule. Primary target molecules can include, but are not limited to, phosphatidylinositol 3-kinase (PI-3K), P21$^{ras}$GAPase-activating protein and associated P190 and P62 protein, phospholipases such as PLCγ1 and PLCγ2, MAP kinase, Shc and VAV. A primary target molecule is capable of producing second messenger molecule which is capable of further amplifying a transduced signal. Second messenger molecules include, but are not limited to diacylglycerol and inositol 1,4,5-triphosphate (IP3). Second messenger molecules are capable of initiating physiological events which can lead to alterations in gene transcription. For example, production of IP3 can result in release of intracellular calcium, which can then lead to activation of calmodulin kinase II, which can then lead to serine phosphorylation of a DNA binding protein referred to as ets-1 proto-onco-protein. Diacylglycerol is capable of activating the signal transduction protein, protein kinase C which affects the activity of the AP1 DNA binding protein complex. Signal transduction pathways can lead to transcriptional activation of genes such as c-fos, egr-1, and c-myc.

Shc can be thought of as an adapter molecule. An adapter molecule comprises a protein that enables two other proteins to form a complex (e.g., a three molecule complex). Shc protein enables a complex to form which includes Grb2 and SOS. Shc comprises an SH2 domain that is capable of associating with the SH2 domain of Grb2.

Molecules of a signal transduction pathway can associate with one another using recognition sequences. Recognition sequences enable specific binding between two molecules. Recognition sequences can vary depending upon the structure of the molecules that are associating with one another. A molecule can have one or more recognition sequences, and as such can associate with one or more different molecules. Signal transduction pathways for MIRR complexes are capable of regulating the biological functions of a cell. Such functions can include, but are not limited to the ability of a cell to grow, to differentiate and to secrete cellular products. MIRR-induced signal transduction pathways can regulate the biological functions of specific types of cells involved in particular responses by an animal, such as immune responses, inflammatory responses and allergic responses. Cells involved in an immune response can include, for example, B cells, T cells, macrophages, dendritic cells, natural killer cells and plasma cells. Cells involved in inflammatory responses can include, for example, basophils, mast cells, eosinophils, neutrophils and macrophages. Cells involved in allergic responses can include, for example mast cells, basophils, B cells, T cells and macrophages.

In exemplary embodiments of the subject assay, signal transduction is measured by detection of second messengers, such as a phosphorylated src-like protein, includes reporter constructs or indicator genes which include transcriptional regulatory elements such as serum response element (SRE), 12-O-tetradecanoyl-phorbol-13-acetate response element, cyclic AMP response element, c- fos promoter, or a CREB-responsive element.

Nuclear Receptors

In another embodiment, the target receptor is a nuclear receptor. The nuclear receptors may be viewed as ligand-dependent transcription factors. These receptors provide a direct link between extracellular signals, mainly hormones, and transcriptional responses. Their transcriptional activation function is regulated by endogenous small molecules, such as steroid hormones, vitamin D, ecdysone, retinoic acids and thyroid hormones, which pass readily through the plasma membrane and bind their receptors inside the cell (Laudet and Adelmant (1995) *Current Biology* 5:124). The majority of these receptors appear to contain three domains: a variable amino terminal domain; a highly conserved, DNA-binding domain and a moderately conserved, carboxyl-terminal ligand-binding domain (Power et al. (1993) *Curr. Opin. Cell Biol.* 5:499–504). Examples include the estrogen, progesterone, androgen, thyroid hormone and mineralocorticoid receptors. In addition to the known steroid receptors, at least 40 orphan members of this superfamily have been identified. (Laudet et al., (1992) *EMBO J.* 11:1003–1013). There are at least four groups of orphan nuclear receptors represented by NGF1, FTZ-F1, Rev-erbs, and RARs, which are by evolutionary standards, only distantly related to each other (Laudet et al. supra). While the steroid hormone receptors bind exclusively as homodimers to a palindrome of their hormone responsive element other nuclear receptors bind as heterodimers. Interestingly, some orphan receptors bind as monomers to similar response elements and require for their function a specific motif that is rich in basic amino-acid residues and is located corboxy-terminal to the DNA-binding domain (Laudet and Adelmant supra.)

In preferred embodiments, the subject assay utilizes a hormone-dependent reporter construct for selection. For instance, glucocorticoid response elements (GREs) and thyroid receptor enhancer-like DNA sequences (TREs) can be used to drive expression of reporter construct in response to hormone binding to hormone receptors. GRE's are enhancer-like DNA sequences that confer glucocorticoid responsiveness via interaction with the glucocorticoid receptor. See Payvar, et al. (1983) *Cell* 35:381 and Schiedereit et al. (1983) *Nature* 304:749. TRE's are similar to GRE's except that they confer thyroid hormone responsiveness via interaction with thyroid hormone receptor. It is known that a steroid or thyroid hormone enters cells by facilitated diffusion and binds to its specific receptor protein, initiating an allosteric alteration of the protein. As a result of this alteration, the hormone/receptor complex is capable of binding to certain specific sites on transcriptional regulatory sequence with high affinity.

Many of the primary effects of steroid and thyroid hormones involve increased transcription of a subset of genes in specific cell types. Moreover, there is evidence that activation of transcription (and, consequently, increased expression) of genes which are responsive to steroid and thyroid hormones (through interaction of chromatin with hormone receptor/hormone complex) is effected through binding of the complex to enhancers associated with the genes.

A number of steroid hormone and thyroid hormone responsive transcriptional control units, some of which have been shown to include enhancers, have been identified. These include the mouse mammary tumor virus 5'-long terminal repeat (MMTV LTR), responsive to glucocorticoid, aldosterone and androgen hormones; the transcriptional control units for mammalian growth hormone genes, responsive to glucocorticoids, estrogens, and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic alpha 2u -globulin gene transcriptional control units, responsive to androgens, estrogens, thyroid hormones and glucocorticoids. Such steroid hormone and thyroid hormone responsive transcriptional control units can be used to generate reporter constructs or indicator genes which are sensitive to agonists and antagonists of the steroid hormone and/or thyroid hormone receptors. See, for example, U.S. Pat. Nos. 5,298,429 and 5,071,773, both to Evans, et. al. Moreover, the art describes the functional expression of such receptors in yeast. See also for example, Caplan et al. (1995) *J Biol Chem* 270:5251–7; and Baniahmad et al. (1995) Mol Endocrinol 9:34–43.

Receptor tyrosine kinases

In still another embodiment, the target receptor is a receptor tyrosine kinase. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the eph/eck family contain cysteine-rich sequences (Hirai et al., (1987) *Science* 238:1717–1720 and Lindberg and Hunter, (1990) *Mol. Cell. Biol.* 10:6316–6324). The functional domains of the kinase region of these three classes of receptor tyrosine kinases are encoded as a contiguous sequence (Hanks et al. (1988) *Science* 241:42–52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with by far the largest number of known members is the EPH family. Since the description of the prototype, the EPH receptor (Hirai et al. (1987) *Science* 238:1717–1720), sequences have been reported for at least ten members of this family, not counting apparently orthologous receptors found in more than one species. Additional partial sequences, and the rate at which new members are still being reported, suggest the family is even larger (Maisonpierre et al. (1993) *Oncogene* 8:3277–3288; Andres et al. (1994) Oncogene 9:1461–1467; Henkemeyer et al. (1994) *Oncogene* 9:1001–1014; Ruiz et al. (1994) *Mech Dev* 46:87–100; Xu et al. (1994) *Development* 120:287–299; Zhou et al. (1994) *J Neurosci Res* 37:129–143; and references in Tuzi and Gullick (1994) *Br J Cancer* 69:417–421). Remarkably, despite the large number of members in the EPH family, all of these molecules were identified as orphan receptors without known ligands.

The expression patterns determined for some of the EPH family receptors have implied important roles for these molecules in early vertebrate development. In particular, the timing and pattern of expression of sek, mek4 and some of the other receptors during the phase of gastrulation and early organogenesis has suggested functions for these receptors in the important cellular interactions involved in patterning the embryo at this stage (Gilardi-Hebenstreit et al. (1992) *Oncogene* 7:2499–2506; Nieto et al. (1992) *Development* 116:1137–1150; Henkemeyer et al., supra; Ruiz et al., supra; and Xu et al., supra). Sek, for example, shows a notable early expression in the two areas of the mouse embryo that show obvious segmentation, namely the somites in the mesoderm and the rhombomeres of the hindbrain; hence the name sek, for segmentally expressed kinase (Gilardi-Hebenstreit et al., supra; Nieto et al., supra). As in Drosophila, these segmental structures of the mammalian embryo are implicated as important elements in establishing the body plan. The observation that Sek expression precedes the appearance of morphological segmentation suggests a role for sek in forming these segmental structures, or in determining segment-specific cell properties such as lineage compartmentation (Nieto et al., supra). Moreover, EPH receptors have been implicated, by their pattern of expression, in the development and maintenance of nearly every tissue in the embryonic and adult body. For instance, EPH receptors have been detected throughout the nervous system, the testes, the cartilaginous model of the skeleton, tooth primordia, the infundibular component of the pituitary, various epithelia tissues, lung, pancreas, liver and kidney tissues. Observations such as this have been indicative of important and unique roles for EPH family kinases in development and physiology, but further progress in understanding their action has been severely limited by the lack of information on their ligands.

As used herein, the terms "EPH receptor" or "EPH-type receptor" refer to a class of receptor tyrosine kinases, comprising at least eleven paralogous genes, though many more orthologs exist within this class, e.g. homologs from different species. EPH receptors, in general, are a discrete group of receptors related by homology and easily recognizable, e.g., they are typically characterized by an extracellular domain containing a characteristic spacing of cysteine residues near the N-terminus and two fibronectin type III repeats (Hirai et al. (1987) *Science* 238:1717–1720; Lindberg et al. (1990) *Mol Cell Biol* 10:6316–6324; Chan et al. (1991) *Oncogene* 6:1057–1061; Maisonpierre et al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) Mech Dev 46:87–100; Xu et al. (1994) *Development* 120:287–299; Zhou et al. (1994) *J Neurosci Res* 37:129–143; and references in Tuzi and Gullick (1994) *Br J Cancer* 69:417–421). Exemplary EPH receptors include the eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors. The term "EPH receptor" refers to the membrane form of the receptor protein, as well as soluble extracellular fragments which retain the ability to bind the ligand of the present invention.

In exemplary embodiments, the detection signal is provided by detecting phosphorylation of intracellular proteins, e.g., MEKKs, MEKs, or Map kinases, or by the use of reporter constructs or indicator genes which include transcriptional regulatory elements responsive to c-fos and/or c-jun. Described infra.

G Protein-Coupled Receptors

One family of signal transduction cascades found in eukaryotic cells utilizes heterotrimeric "G proteins." Many different G proteins are known to interact with receptors. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha ($\alpha$), beta ($\beta$) and gamma ($\gamma$) subunits, are complexed with the nucleotide guanosine diphosphate (GDP) and are in contact with receptors. When a hormone or other first messenger binds to receptor, the receptor changes conformation and this alters its interaction with the G protein. This spurs the $\alpha$ subunit to release GDP, and the more abundant nucleotide guanosine triphosphate (GTP), replaces it, activating the G protein. The G protein then dissociates to separate the $\alpha$ subunit from the still complexed beta and gamma subunits. Either the G$\alpha$ subunit, or the G$\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the G$\alpha$ converts the GTP to GDP, thereby inactivating itself. The inactivated G$\alpha$ may then reassociate with the G$\beta\gamma$ complex.

Hundreds, if not thousands, of receptors convey messages through heterotrimeric G proteins, of which at least 17 distinct forms have been isolated. Although the greatest variability has been seen in the a subunit, several different $\beta$ and $\gamma$ structures have been reported. There are, additionally, several different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) Cell 72, 415; Kouba et al. *FEBS Lett.* (1993) 321, 173; Birkenbach et al.(1993) *J. Virol.* 67, 2209.

The "exogenous receptors" of the present invention may be any G protein-coupled receptor, preferably exogenous to the cell, which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, adrenaline, adrenaline., histamine, noradrenaline, noradrenaline, noradrenaline., tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone(ghrh), insect diuretic hormone, interleukin-8, leutropin (lh/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Examples of G-protein coupled receptors include, but are not limited to, dopaminergic, muscarinic cholinergic, a-adrenergic, b-adrenergic, opioid (including delta and mu), cannabinoid, serotoninergic, and GABAergic receptors. Preferred receptors include the 5HT family of receptors, dopamine receptors,C5a receptor and FPRL-1 receptor, cyclo-histidyl-proline-diketoplperazine receptors, melanocyte stimulating hormone release inhibiting factor receptor, and receptors for neurotensin, thyrotropin releasing hormone, calcitonin, cholecytokinin-A, neurokinin-2, histamine-3, cannabinoid, melanocortin, or adrenomodulin, neuropeptide-Y1 or galanin. Other G protein coupled receptors (GPCRs) are listed in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include Ste2, Ste3 and gal10. Suitable signal sequences include those of Ste2, Ste3 and of other genes which encode proteins secreted by yeast cells. Preferably, when a yeast cell is used, the codons of the gene would be optimized for expression in yeast. See Hoekema et al.,(1987) *Mol. Cell. Biol.*, 7:2914–24; Sharp, et al., (1986)14:5125–43.

The homology of STRs is discussed in Dohlman et al., *Ann. Rev. Biochem.*, (1991) 60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

In certain embodiments, if the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible. For example, the V-VI loop of a heterologous G protein coupled receptor could be replaced with that of the yeast STE2 or STE3 receptor),.

In yet another embodiment, a compatible G protein can be provided. A compatable G proein for use in the instant assays can include a heterologous or chimeric G protein subunit (or subunits) such as those described in the art (see e.g., PCT PCT/US94/03143) and as discussed in more detail below.

Preferably, the yeast genome is modified so that it is unable to produce the yeast receptors which are homologous to the exogenous receptors in functional form.

A. Chemoattractant receptors

An exemplary GPCR is the N-formyl peptide receptor, a classic example of a calcium mobilizing GPCR expressed by neutrophils and other phagocytic cells of the mammalian immune system (Snyderman et al. (1988) *In Inflammation: Basic Principles and Clinical Correlates*, pp. 309–323). N-formyl peptides of bacterial origin bind to the receptor and engage a complex activation program that results in directed cell movement, release of inflammatory granule contents, and activation of a latent NADPH oxidase which is important for the production of metabolites of molecular oxygen. This pathway initiated by receptor-ligand interaction is critical in host protection from pyogenic infections. Similar signal transduction occurs in response to the inflammatory peptides C5a and IL-8.

Two other formyl peptide receptor like (FPRL) genes have been cloned based on their ability to hybridize to a fragment of the NFPR cDNA coding sequence. These have been named FPRL1 (Murphy et al. (1992) *J. Biol Chem.* 267:7637–7643) and FPRL2 (Ye et al. (1992) *Biochem Biophys Res. Comm.* 184:582–589). FPRL2 was found to mediate calcium mobilization in mouse fibroblasts transfected with the gene and exposed to formyl peptide. In contrast, although FPRL 1 was found to be 69% identical in amino acid sequence to NFPR, it did not bind prototype N-formyl peptides ligands when expressed in heterologous cell types. This lead to the hypothesis of the existence of an as yet unidentified ligand for the FPRL1 orphan receptor (Murphy et al. supra).

B. G proteins

In the case of an exogenous G-protein coupled receptor, the yeast cell must be able to produce a G protein which is activated by the exogenous receptor, and which can in turn activate the yeast effector(s). The art suggests that the endogenous yeast Gα subunit (e.g., GPA) will be often be sufficiently homologous to the "cognate" Gα subunit which is natively associated with the exogenous receptor for coupling to occur. More likely, it will be necessary to genetically engineer the yeast cell to produce a foreign Gα subunit which can properly interact with the exogenous receptor. For example, the Gα subunit of the yeast G protein may be replaced by the Gα subunit natively associated with the exogenous receptor.

Dietzel and Kurjan, (1987) Cell, 50:1001) demonstrated that rat Gas functionally coupled to the yeast Gβγ complex. However, rat Gαi2 complemented only when substantially overexpressed, while Gα0 did not complement at all. Kang, et al., *Mol. Cell. Biol.*, (1990)10:2582). Consequently, with some foreign Gα subunits, it is not feasible to simply replace the yeast Gα.

If the exogenous G protein coupled receptor is not adequately coupled to yeast Gβγ by the Gα subunit natively associated with the receptor, the Gα subunit may be modified to improve coupling. These modifications often will take the form of mutations which increase the resemblance of the Gα subunit to the yeast Gα while decreasing its resemblance to the receptor-associated Gα. For example, a residue may be changed so as to become identical to the corresponding yeast Gα residue, or to at least belong to the same exchange group of that residue. After modification, the modified Gα subunit might or might not be "substantially homologous" to the foreign and/or the yeast Gα subunit.

The modifications are preferably concentrated in regions of the Gα which are likely to be involved in Gβγ binding. In some embodiments, the modifications will take the form of replacing one or more segments of the receptor-associated Gα with the corresponding yeast Gα segment(s), thereby forming a chimeric Gα subunit. In other embodiments, point mutations may be sufficient.

This chimeric Gα subunit will interact with the exogenous receptor and the yeast Gβγ complex, thereby permitting signal transduction. While use of the endogenous yeast Gβγ is preferred, if a foreign or chimeric Gβγ is capable of transducing the signal to the yeast effector, it may be used instead.

C. Gα Structure

Some aspects of Gα structure are relevant to the design of modified Gα subunits. The amino terminal 66 residues of GPA1 are aligned with the cognate domains of human Gαs, Gαi2, Gαi3, Gα16 and transducin. In the GPA41Gα hybrids, the amino terminal 41 residues (derived from GPA1) are identical, end with the sequence-LEKQRDKNE- and are underlined for emphasis. All residues following the glutamate (E) residue at position 41 are contributed by the human Gα subunits, including the consensus nucleotide binding motif -GxGxxG-. Periods in the sequences indicate gaps that have been introduced to maximize alignments in this region. Codon bias is mammalian. For alignments of the entire coding regions of GPA 1 with Gαs, Gαi, and GαO, Gαq and Gαz, see Dietzel and Kurjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc Natl. Acad Sci USA* 84:5115–5119).

The gene encoding a G protein homolog of *S. cerevisiae* was cloned independently by Dietzel and Kurjan (supra) (SCG1) and by Nakafuku, et al. (1987 *Proc Natl Acad Sci* 84:2140–2144) (GPA1). Sequence analysis revealed a high degree of homology between the protein encoded by this gene and mammalian Gα. GPA1 encodes a protein of 472 amino acids, as compared with approximately 340–350 a.a. for most mammalian Gα subunits in four described families, Gαs, Gαi, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to GQS (33% identity, or 51% with conservative substitutions) (Nakafuku, et al., supra).

The regions of high sequence homology among Gα subunits are dispersed throughout their primary sequences, with the regions sharing the highest degree of homology mapping to sequence that comprises the guanine nucleotide binding/GTPase domain. This domain is structurally similar to the αβ fold of ras proteins and the protein synthesis elongation factor EF-Tu. This highly conserved guanine nucleotide-binding domain consists of a six-stranded β sheet surrounded by a set of five α-helices. It is within these α sheets and a helices that the highest degree of conservation is observed among all Gα proteins, including GPA1. The least sequence and structural homology is found in the intervening loops between the β sheets and a helices that define the core GTPase domain. There are a total of four "intervening loops" or "inserts" present in all Gα subunits. In the crystal structures reported to date for the GDP- and GTPγS-liganded forms of bovine rod transducin (Noel, et al. (1993) *Nature* 366:654–663); (Lambright, et al. (1994) *Nature* 369:621–628), the loop residues are found to be outside the core GTPase structure. Functional roles for these loop structures have been established in only a few instances. A direct role in coupling to phosphodiesterase-γ has been demonstrated for residues within inserts 3 and 4 of Gαt (Rarick, et al. (1992) *Science* 256:1031–1033); (Artemyev, et al. (1992) *J. Biol. Chem.* 267:25067–25072), while a "GAP-like" activity has been ascribed to the largely a-helical insert 1 domain of GαS (Markby, et al. (1993) *Science* 262:1805–1901).

While the amino- and carboxy-termini of Gα subunits do not share striking homology either at the primary, secondary, or tertiary levels, there are several generalizations that can be made about them. First, the amino termini of Gα subunits have been implicated in the association of Gα with Gβγ complexes and in membrane association via N-terminal myristoylation. In addition, the carboxy-termini have been implicated in the association of Gαβγ heterotrimeric complexes with G protein-coupled receptors (Sullivan, et al. (1987) *Nature* 330:758–760); West, et al. (1985) *J. Biol. Chem.* 260:14428–14430); (Conklin, et al. (1993)*Nature* 363:274–276); (Kallal and Kurjan. 1997. *Mol. Cell. Biol.* 17:2897). Data in support of these generalizations about the function of the N-terminus derive from several sources, including both biochemical and genetic studies.

The FIGURE shows the amino terminal 66 residues of GPA1 aligned with the cognate domains of human Gαs, Gαi2, Gαi3, Gα16 and transducin. In the GPA41Gα hybrids, the amino terminal 41 residues (derived from GPA1) are identical, end with the sequence-LEKQRDKNE- (SEQ ID NO: 47). All residues following the glutamate (E) residue at position 41 are contributed by the human Gα subunits, including the consensus nucleotide binding motif shown in the amino acid sequence -GxGxxG-. Periods in the sequences indicate gaps that have been introduced to maximize alignments in this region. Codon bias is mammalian. For alignments of the entire coding regions of GPA1 with Gαs, Gαi, and GαO, Gαq and Gαz, see Dietzel and Kurjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc Natl. Acad Sci USA* 84:5115–5119).

In other biochemical studies aimed at examining the role of the amino-terminus of Gα in driving the association between Gα and Gβγ subunits, proteolytically or genetically truncated versions of Gα subunits were assayed for their ability to associate with Gβγ complexes, bind guanine nucleotides and/or to activate effector molecules. In all cases, Gα subunits with truncated amino termini were deficient in all three functions (Graf, et al. (1992) *J. Biol. Chem.* 267:24307–24314); (Journot, et al. (1990) *J Biol Chem.* 265:9009–9015); and (Neer, et al. (1988) *J. Biol. Chem* 263:8996–9000). Slepak, et al. (1993, *J. Biol. Chem.* 268:1414–1423) reported a mutational analysis of the N-terminal 56 a.a. of mammalian Gα expressed in *Escherichia coli*. Molecules with an apparent reduced ability to interact with exogenously added mammalian Gβγ were identified in the mutant library. As the authors pointed out, however, the assay used to screen the mutants the extent of ADP-ribosylation of the mutant Gα by pertussis toxin was not a completely satisfactory probe of interactions between Gα and Gβγ. Mutations identified as inhibiting the interaction of the subunits, using this assay, may still permit the complexing of Gα and Gβγ while sterically hindering the ribosylation of Gα by toxin. Genetic studies examined the role of amino-terminal determinants of Gα in heterotrimer subunit association have been carried out in both yeast systems using GPA1-mammalian Gα hybrids (Kang, et al. (1990) *Mol. Cell. Biol.* 10:2582–2590) and in mammalian systems using Gαi/Gαs hybrids (Russell and Johnson (1993) *Mol. Pharmacol.* 44:255–263). In the former studies, gene fusions, composed of yeast GPA1 and mammalian Gα sequences were constructed by Kang, et al. (supra) and assayed for their ability to complement a gpa1 null phenotype (i.e., constitutive activation of the pheromone response pathway) in *S. cerevisiae*. Kang, et al. demonstrated that wild type mammalian Gαs, Gαi but not Gα proteins are competent to associate with yeast Gα and suppress the gpa1 null phenotype, but only when overexpressed. Fusion proteins containing the amino-terminal 330 residues of GPA1 sequence linked to 160, 143, or 142 residues of the mammalian Gαs, Gαi and Gαo carboxyl-terminal regions, respectively, also coupled to the yeast mating response pathway when overexpressed on high copy plasmids with strong inducible (CUP) or constitutive (PGK) promoters. All three of these hybrid molecules were able to complement the gpa1 null mutation in a growth arrest assay, and were additionally able to inhibit αfactor responsiveness and mating in tester strains. These last two observations argue that hybrid yeast-mammalian Gα subunits are capable of interacting directly with yeast Gβγ, thereby disrupting the normal function of the yeast heterotrimer. Fusions containing the amino terminal domain of Gαs, Gαi or Gαo, however, did not complement the gpa1 null phenotype, indicating a requirement for determinants in the amino terminal 330 amino acid residues of GPA1 for association and sequestration of yeast Gβγ complexes. Taken together, these data suggest that determinants in the amino terminal region of Gα subunits determine not only the ability to associate with Gβγ subunits in general, but also with specific Gβγ0 subunits in a species-restricted manner.

Hybrid Gαi/Gαs subunits have been assayed in mammalian expression systems (Russell and Johnson (supra). In these studies, a large number of chimeric Gα subunits were assayed for an ability to activate adenylyl cyclase, and therefore, indirectly, for an ability to interact with Gβγ(i.e., coupling of Gα to Gβγ=inactive cyclase; uncoupling of Gα from Gβγ=active cyclase). From these studies a complex picture emerged in which determinants in the region between residues 25 and 96 of the hybrids were found to determine the state of activation of these alleles as reflected in their rates of guanine nucleotide exchange and GTP hydrolysis and the extent to which they activated adenylyl cyclase in vivo. These data could be interpreted to support the hypothesis that structural elements in the region between the amino terminal methionine and the ~1 sheet identified in the crystal structure of Gαt (see Noel, et al. supra and Lambright, et al. supra) are involved in determining the state of activity of the heterotrimer by (1) driving association/dissociation between Gα and Gβγ subunits; (2) driving GDP/GTP exchange. While there is no direct evidence provided by these studies to support the idea that residues in this region of Gα and residues in Gβγ subunits contact one another, the data nonetheless provide a positive indication for the construction of hybrid Gα subunits that retain function. There is, however, a negative indicator that derives from this work in that some hybrid constructs resulted in constitutive activation of the chimeric proteins (i.e., a loss of receptor-dependent stimulation of Gβγ dissociation and effector activation).

D. Construction of chimeric Gα subunits

In designing Gα subunits capable of transmitting, in yeast, signals originating at mammalian G protein-coupled receptors, two general desiderata were recognized. First, the subunits should retain as much of the sequence of the native mammalian proteins as possible. Second, the level of expression for the heterologous components should approach, as closely as possible, the level of their endogenous counterparts. The results described by King, et al. (1990, Science 250:121–123) for expression of the human p2-adrenergic receptor and Gαs in yeast, taken together with negative results obtained by Kang, et al. (supra) with full-length mammalian Gα subunits other than Gαs, led us to the following preferences for the development of yeast strains in which mammalian G protein-coupled receptors could be linked to the pheromone response pathway.

1. Mammalian Gα subunits will be expressed using the native sequence of each subunit or, alternatively, as minimal gene fusions with sequences from the amino-terminus of GPA1 replacing the homologous residues from the mammalian Gα subunits.
2. Mammalian Gα subunits will be expressed from the GPA1 promoter either on low copy plasmids or after integration into the yeast genome as a single copy gene.
3. Endogenous Gβγ subunits will be provided by the yeast STE4 and STE18 loci.

E. Site-Directed Mutagenesis versus Random Mutagenesis

There are two general approaches to solving structure-function problems of the sort presented by attempts to define the determinants involved in mediating the association of the subunits that comprise the G protein heterotrimer. The first approach, discussed above with respect to hybrid constructs, is a rational one in which specific mutations or alterations are introduced into a molecule based upon the available experimental evidence. In a second approach, random mutagenesis techniques, coupled with selection or screening systems, are used to introduce large numbers of mutations into a molecule, and that collection of randomly mutated molecules is then subjected to a selection for the desired phenotype or a screen in which the desired phenotype can be observed against a background of undesirable phenotypes. With random mutagenesis one can mutagenize an entire molecule or one can proceed by cassette mutagenesis. In the former instance, the entire coding region of a molecule is mutagenized by one of several methods (chemical, PCR, doped oligonucleotide synthesis) and that collection of randomly mutated molecules is subjected to selection or screening procedures. Random mutagenesis can be applied in this way in cases where the molecule being studied is relatively small and there are powerful and stringent selections or screens available to discriminate between the different classes of mutant phenotypes that will inevitably arise. In the second approach, discrete regions of a protein, corresponding either to defined structural (i.e. α-helices, β-sheets, turns, surface loops) or functional determinants (e.g., catalytic clefts, binding determinants, transmembrane segments) are subjected to saturating or semi-random mutagenesis and these mutagenized cassettes are re-introduced into the context of the otherwise wild type allele. Cassette mutagenesis is most useful when there is experimental evidence available to suggest a particular function for a region of a molecule and there is a powerful selection and/or screening approach available to discriminate between interesting and uninteresting mutants. Cassette mutagenesis is also useful when the parent molecule is comparatively large and the desire is to map the functional domains of a molecule by mutagenizing the molecule in a step-wise fashion, i.e. mutating one linear cassette of residues at a time and then assaying for function.

The present invention contemplates applying random mutagenesis in order to further delineate the determinants involved in Gα-Gβγ association. Random mutagenesis may be accomplished by many means, including:

1. PCR mutagenesis, in which the error prone Taq polymerase is exploited to generate mutant alleles of Gα subunits, which are assayed directly in yeast for an ability to couple to yeast Gβγ.
2. Chemical mutagenesis, in which expression cassettes encoding Gα subunits are exposed to mutagens and the protein products of the mutant sequences are assayed directly in yeast for an ability to couple to yeast Gβγ.
3. Doped synthesis of oligonucleotides encoding portions of the Gα gene.
4. In vivo mutagenesis, in which random mutations are introduced into the coding region of Gα subunits by passage through a mutator strain of E. coli, XL1-Red (mutD5 mutS mutT) (Stratagene, Menasa, Wis.).

The random mutagenesis may be focused on regions suspected to be involved in Gα-Gβγ association as discussed in the next section. Random mutagenesis approaches are feasible for two reasons. First, in yeast one has the ability to construct stringent screens and facile selections (growth vs. death, transcription vs. lack of transcription) that are not readily available in mammalian systems. Second, when using yeast it is possible to screen efficiently through thousands of transformants rapidly. Cassette mutagenesis is immediately suggested by the observation (see infra) that the $GPA_{41}$ hybrids couple to the pheromone response pathway. This relatively small region of Gα subunits represents a reasonable target for this type of mutagenesis. Another region that may be amenable to cassette mutagenesis is that defining the surface of the switch region of Gα subunits that is solvent-exposed in the crystal structures of Gαi and transducin. From the data described below, this surface may contain residues that are in direct contact with yeast Gβγ subunits, and may therefore be a reasonable target for mutagenesis.

F Rational Design of Chimeric Gα Subunits

Several classes of rationally designed GPA1-mammalian Gα hybrid subunits have been tested for the ability to couple to yeast βγ. The first, and largest, class of hybrids are those that encode different lengths of the GPA1 amino terminal domain in place of the homologous regions of the mammalian Gα subunits. This class of hybrid molecules includes $GPA_{BAMH1}$, $GPA_{41}$, $GPA_{ID}$, and $GPA_{LW}$ hybrids, described below. The rationale for constructing these hybrid Gα proteins is based on results, described above, that bear on the importance of the amino terminal residues of Gα in mediating interaction with Gβγ.

Preferably, the yeast Gα subunit is replaced by a chimeric Gα subunit in which a portion, e.g., at least about 20, more preferably at least about 40, amino acids, which is substantially homologous with the corresponding residues of the amino terminus of the yeast Gα, is fused to a sequence substantially homologous with the main body of a mammalian (or other exogenous) Gα. While 40 amino acids is the suggested starting point, shorter or longer portions may be tested to determine the minimum length required for coupling to yeast Gβγ and the maximum length compatible with retention of coupling to the exogenous receptor. It is presently believed that only the final 10 or 20 amino acids at the carboxy terminus of the Gα subunit are required for interaction with the receptor.

$GPA_{BAMH1}$ hybrids. Kang et al. supra. described hybrid G α subunits encoding the amino terminal 310 residues of GPA1 fused to the carboxyl terminal 160, 143 and 142 residues, respectively, of GαS, Gαi2, and Gαo. In all cases examined by Kang et al., the hybrid proteins were able to complement the growth arrest phenotype of gpa1 strains. These findings have been confirmedand, in addition, have constructed and tested hybrids between GPA1 and Gαi3, Gαq and Gα16. All hybrids of this type that have been tested functionally complement the growth arrest phenotype of gpal strains.

GPA41 hybrids. The rationale for constructing a minimal hybrid encoding only 41 amino acids of GPA1 relies upon the biochemical evidence for the role of the amino-terminus of Gα subunits discussed above, together with the following observation. G β and Gγ subunits are known to interact via α- helical domains at their respective amino-termini (Pronin, et al. (1992) *Proc. Natl. Acad. Sci. USA* 89:6220–6224); Garritsen, et al. 1993). The suggestion that the amino termini of Gα subunits may form an helical coil and that this helical coil may be involved in association of Gα with Gβγ (Masters et al (1986) *Protein Engineering* 1:47–54); Lupas et al.(1992) *FEBS Lett.* 314:105–108) leads to the hypothesis that the three subunits of the G-protein heterotrimer interact with one another reversibly through the winding and unwinding of their amino-terminal helical regions. A mechanism of this type has been suggested, as well, from an analysis of leucine zipper mutants of the GCN4 transcription factor (Harbury, et al. (1993) *Science* 262:1401–1407). The rationale for constructing hybrids like those described by Kang, et al. supra., that contain a majority of yeast sequence and only minimal mammalian sequence, derives from their ability to function in assays of coupling between Gα and Gβγ subunits. However, these chimeras had never been assayed for an ability to couple to both mammalian G protein-coupled receptors and yeast Gβγ subunits, and hence to reconstitute a hybrid signaling pathway in yeast.

$GPA_{41}$ hybrids that have been constructed and tested include Gαs, Gαi2, Gαi3, Gαq, Gαo$_a$, Gαo$_b$ and Gα16. Hybrids of Gαs, Gαi2, Gαi3, and Gα16 functionally complement the growth arrest phenotype of gpal strains, while $GPA_{41}$ hybrids of Gαo$_a$ and Gαo$_b$ do not. In addition to being tested in a growth arrest assay, these constructs have been assayed in the more sensitive transcriptional assay for activation of a fus1p-HIS3 gene. In both of these assays, the $GPA_{41}$-Gαs hybrid couples less well than the GPα$_{41}$-i2, -i3, and -16 hybrids, while the GPα$_{41}$ -o$_a$, and -o$_b$ hyrids do not function in either assay.

Several predictive algorithms indicate that the amino terminal domain up to the highly conserved sequence motif-LLLLGAGESG- (SEQ ID NO:46) (the first L in this motif is residue 43 in GPA 1) forms a helical structure with amphipathic character. Assuming that a heptahelical repeat unit, the following hybrids between GPA1 and GαS can be used to define the number of helical repeats in this motif necessary for hybrid function:

GPA1-7/Gαs8-394
GPA1-14/Gαs15-394
GPA1-21/Gαs22-394
GPA1-28/Gαs29-394
GPA1-35/Gαs36-394
GPA1-42/Gαs43-394

In these hybrids, the prediction is that the structural repeat unit in the amino terminal domain up to the tetra-leucine motif is 7, and that swapping sequences in units of 7 will in effect amount to a swap of unit turns of turns of the helical structure that comprises this domain.

A second group of "double crossover'" hybrids of this class are those that are aligned on the first putative heptad repeat beginning with residue G11 in GPA1. In these hybrids, helical repeats are swapped from GPA1 into a GaS backbone one heptad repeat unit at a time.

GαS1-10/GPA11-17/Gαs18-394
GαS1-17/GPA18-24/GαS25-394
GαS1-17/GPA25-31/GαS32-394
GαS?-17/GPA32-38/GαS39-394

The gap that is introduced between residues 9 and 10 in the GaS sequence is to preserve the alignment of the -LLLLGAGE- (amino acids 1–8 of SEQ ID NO: 46) sequence motif This class of hybrids can be complemented by cassette mutagenesis of each heptad repeat followed by screening of these collections of "heptad" libraries in standard coupling assays.

A third class of hybrids based on the prediction that the amino terminus forms a helical domain with a heptahelical repeat unit are those that effect the overall hydrophobic or hydrophilic character of the opposing sides of the predicted helical structure (See Lupas et al. supra). In this model, the α and d positions of the heptad repeat abcdefg are found to be conserved hydrophobic residues that define one face of the helix, while the e and g positions define the charged face of the helix. In this class of hybrids, the sequence of the GaS parent is maintained except for specific substitutions at one or more of the following critical residues to render the different helical faces of GaS more "GPA1-like"

K8Q
+I-10
E1OG
Q12E
R13S
N14D
E15P
E15F
K17L
E21R
K28Q
K32L
V36R

This collection of single mutations could be screened for coupling efficiency to yeast Gβγ and then constructed in combinations (double and greater if necessary).

A fourth class of hybrid molecules that span this region of GPA1-Gα hybrids are those that have junctions between GPA1 and Gα subunits introduced by three primer PCR. In this approach, the two outside primers are encoded by sequences at the initiator methionine of GPA1 on the 5' side and at the tetraleucine motif of GαS (for example) on the 3' side. A series ofjunctional primers spanning different junctional points can be mixed with the outside primers to make a series of molecules each with different amounts of GPA1 and GαS sequences, respectively.

$GPA_{ID}$ and $GPA_{LW}$ hybrids. The regions of high homology among Gβγ subunits that have been identified by sequence alignment are interspersed throughout the molecule. The GI region containing the highly conserved -GSGESGDST- motif is followed immediately by a region of very low sequence consevation, the "il" or insert 1 region. Both sequence and length vary considerably among the il regions of the Gα subunits. By aligning the sequences of Gα subunits, the conserved regions bounding the il region were identified and two additional classes of GPA1-Gα hybrids were constructed. The $GPA_{ID}$ hybrids encode the amino terminal 102 residues of GPA1 (up to the sequence -QARKLGIQ-) fused in frame to mammalian Gα subunits, while the GPALW hybrids encode the amino terminal 244 residues of GPA1 (up to the sequence -LIHEDIAKA- in GPA1). The reason for constructing the $GPA_{ID}$ and $GPA_{LW}$ hybrids was to test the hypothesis that the il region of GPA1 is required for mediating the interaction of GPA1 with yeast Gβγ subunits, for the stable expression of the hybrid molecules, or for function of the hybrid molecules. The $GPA_{ID}$ hybrids contain the amino terminal domain of GPA1 fused to the il domain of mammalian subunits, and therefore do not contain the GPA1 il region, while the $GPA_{LW}$ hybrids contain the amino terminal 244 residues of GPA1 including the entire il region (as defined by sequence alignments). Hybrids of both $GPA_{ID}$ and $GPA_{LW}$ classes were constructed for GαS, C-αi2, Gαi3, $G\alpha o_a$, and Gα16; none of these hybrids complemented the gpal growth arrest phenotype.

Subsequent to the construction and testing of the $GPA_{ID}$ and GPALW classes of hybrids, the crystal structures of $G_{transducin}$ in both the GDP and GTPγS-liganded form, and the crystal structure of several Gail variants in the GTPγS-liganded and GDP-$AIF_4$ forms were reported Noel et al. supra; Lambright et al. supra; and Coleman et al.(1994) *Science* 265:1405–1412). The crystal structures reveal that the ilregion defined by sequence alignment has a conserved structure that is comprised of six alpha helices in a rigid array, and that the junctions chosen for the construction of the $GPA_{ID}$ and $GPA_{LW}$ hybrids were not compatible with conservation of the structural features of the il region observed in the crystals. The junction chosen for the $GPA_{ID}$ hybrids falls in the center of the long αA helix; chimerization of this helix in all likelihood destabilizes it and the protein structure in general. The same is true of the junction chosen for the $GPA_{LW}$ hybrids in which the crossover point between GPA1 and the mammalian Gα 10 subunit falls at the end of the short αC helix and therefore may distort it and destabilize the protein.

The failure of the $GPA_{ID}$ and $GPA_{LW}$ hybrids is predicted to be due to disruption of critical structural elements in the il region as discussed above. Based upon new alignments and the data presented in Noel et al (supra), Lambright et al (supra), and Coleman et al (supra), this problem can be averted with the ras-like core domain and the il helical domain are introduced outside of known structural elements like alpha-helices.

Hybrid A GαS1-67/GPA66-299/GαS203-394

This hybrid contains the entire il insert of GPA1 interposed into the GαS sequence.

Hybrid B GPA1-41/GαS4443-67/GPA66-299/GαS203-394

This hybrid contains the amino terminal 41 residues of GPA1 in place of the 42 amino terminal residues of GαS found in Hybrid A.

Gαs Hybrids. There is evidence that the "switch region" encoded by residues 171–237 of Gα transducin (using the numbering of (Noel et al (supra) also plays a role in Gβγ coupling. First, the G226A mutation in GαS prevents the GTP-induced conformational change that occurs with exchange of GDP for GTP upon receptor activation by ligand. This residue maps to the highly conserved sequence -DVGGQ-, present in all Gα subunits and is involved in GTP hydrolysis. In both the Gαt and Gα il crystal structures, this sequence motif resides in the loop that connects the β3 sheet and the α2 helix in the guanine nucleotide binding core. In addition to blocking the conformational change that occurs upon GTP binding, this mutation also prevents dissociation of GTP-liganded Gαs from Gβγ. Second, crosslinking data reveals that a highly conserved cysteine residue in the α2 helix (C215 in Gαo, C2 10 in Gαt) can be crosslinked to the carboxy terminal region of Gβ subunits. Finally, genetic evidence (Whiteway et al. (1993) Mol Cell Biol. 14:3233–3239) identifies an important single residue in GPA1 (E307) in the β2 sheet of the core structure that may be in direct contact with βγ. A mutation in the GPA1 protein at this position suppresses the constitutive signalling phenotype of a variety of STE4 (Gβ) dominant negative mutations that are also known to be defective in Gα-Gβγ association (as assessed in two-hybrid assay in yeast as well as by more conventional genetic tests).

The hypothesis that there are switch region determinants involved in the association of Gα with Gβγ has been tested by constructing a series of hybrid Gα proteins encoding portions of GPA1 and GαS in different combinations.

Two conclusions may be drawn. First, in the context of the amino terminus of GαS, the GPA1 switch region suppresses coupling to yeast Gβγ (SGS), while in the context of the GPA1 amino terminus the GPA1 switch region stabilizes coupling with Gβγ (GPβγ-SGS). This suggests that these two regions of GPA1 collaborate to allow is interactions between Gα subunits and Gβγ subunits. This conclusion is somewhat mitigated by the observation that the GPA$_{41}$-Gαs hybrid that does not contain the GPA1 switch region is able to complement the growth arrest phenotype of gpal strains. A quantitative difference between the behavior of the GPA$_{41}$-Gαs allele and the GPA~I-SGS allele has not been noted, but if this interaction is somewhat degenerate, then it may be difficult to quantitate this accurately. The second conclusion that can be drawn from these results is that there are other determinants involved in stabilizing the interaction of Gα with Gβγ beyond these two regions as none of the GPA1/Gαs hybrid proteins couple as efficiently to yeast Gβγ as does native GPA1.

The role of the surface-exposed residues of this region may be crucial for effective coupling to yeast Gβγ, and can be incorporated into hybrid molecules as follows below.

GαS-GPA-Switch GαS 1-202/GPA298-350/GαS 253-394

This hybrid encodes the entire switch region of GPA 1 in the context of GaS.

GαS-GPA-α2 GQS 1-226/GPA322-332/GQS 238-394

This hybrid encodes the a$^2$ helix of GPA1 in the context of GαS.

GPA41-GαS-GPA-α2GPA1-41 /GQS43-226/GPA322-332/GQS238-394

This hybrid encodes the 41 residue amino terminal domain of GPA1 and the α2 helix of GPA1 in the context of GαS.

Finally, the last class of hybrids that will be discussed here are those that alter the surface exposed residues of the β2 and β3 sheets of αS so that they resemble those of the GPA1 QS helix. These altered α2 helical domains have the following structure. (The positions of the altered residues correspond to GαS.)

L203K
K211E
D215G
K216S
D229S

These single mutations can be engineered into a GαS backbone singly and in pairwise combinations. In addition, they can be introduced in the context of both the full length GαS and the GPA$_{41}$-GαS hybrid described previously. All are predicted to improve the coupling of Gα subunits to yeast Gβγ subunits by virtue of improved electrostatic and hydrophobic contacts between this region and the regions of Gβ defined by Whiteway and coworkers (Whiteway et al (supra) that define site(s) that interact with GPA1).

In summary, the identification of hybrid Gα subunits that couple to the yeast pheromone pathway has led to the following general observations. First, all GPA$_{BAMH1}$ hybrids associate with yeast Gβγ, therefore at a minimum these hybrids contain the determinants in GPA1 necessary for coupling to the pheromone response pathway. Second, the amino terminal 41 residues of GPA1 contain sufficient determinants to facilitate coupling of Gα hybrids to yeast Gβγ in some, but not all, instances, and that some Gα subunits contain regions outside of the first 41 residues that are sufficiently similar to those in GPA1 to facilitate interaction with GPA1 even in the absence of the amino terminal 41 residues of GPA1. Third, there are other determinants in the first 310 residues of GPA1 that are involved in coupling Gα subunits to yeast Gβγ subunits.

The various classes of hybrids noted above are not mutually exclusive. For example, a GPA1 containing GPA1-$_{41}$ could also feature the L203K mutation.

While, for the sake of simplicity, hybrids of yeast GPA1 and a mammalian Gαs have been described, it will be appreciated that hybrids may be made of other yeast Gα subunits and/or other mammalian Gα subunits, notably mammalian Gαi subunits. Moreover, while the described hybrids are constructed from two parental proteins, hybrids of three or more parental proteins are also possible.

As shown in the Examples, chimeric Gα subunits have been especially useful in coupling receptors to Gαi species.

G. Expression of Gα

Kang et al. supra reported that several classes of native mammalian G~subunits were able to interact functionally with yeast a subunits when expression of Gα was driven from a constitutively active, strong promoter (PGK) or from a strong inducible promoter (CUP). These authors reported that rat GαS, Gαi2 or Gαo expressed at high level coupled to yeast βγ. High level expression of mammalian Gα (i.e. non-stoichiometric with respect to yeast βγ) is not desirable for uses like those described in this application. Reconstruction of G protein- coupled receptor signal transduction in yeast requires the signalling component of the heterotrimeric complex (Gβγ) to be present stoichiometrically with Gα subunits. An excess of Gα subunits (as was required for coupling of mammalian Gαi2 and Gαo to yeast Gβγ in Kang et al.) would dampen the signal in systems where Gβγ subunits transduce the signal. An excess of Gα subunits raises the background level of signaling in the system to unacceptably high levels. Preferably, levels of Gα and Gβγ subunits are balanced. For example, heterologous Gα subunits may be expressed from a low copy (CEN ARS) vector containing the endogenous yeast GPA1 promoter and the GPA1 3' untranslated region. The minimum criterion, applied to a heterologous Gα subunit with respect to its ability to couple functionally to the yeast pheromone pathway, is that it complement a gpal genotype when expressed from the GPA1 promoter on low copy plasmids or from an integrated, single copy gene. In the work described in this application, all heterologous Gα subunits have been assayed in two biological systems. In the first assay heterologous Gα subunits are tested for an ability to functionally complement the growth arrest phenotype of gpal strains. In the second assay the transcription of a fus1-HIS3 reporter gene is used to measure the extent to which the pheromone response pathway is activated, and hence the extent to which the heterologous Gα subunit sequesters the endogenous yeast Gβγ complex. Mammalian Gαs, Gαi2, Gαi3, Gαq, Gα11, Gα16, Gαo$_a$, Gαo$_b$, and Gαz from rat, murine or human origins were expressed from a low copy, CEN ARS vector containing the GPA1 promoter. Functional complementation of gpal strains was not observed in either assay system with any of these full-length Gα constructs with the exception of rat and human GαS.

H. Chimeric Yeast βγ subunits

An alternative to the modification of a mammalian Gα subunit for improved signal transduction is the modification of the pertinent sites in the yeast Gβ or Gγ subunits. The principles discussed already with respect to Gα subunits apply, mutatis mutandis, to yeast Gβ or Gγ.

For example, in certain embodiments the yeast Ste4p Gβsubunit can be targetedwith cassette mutagenesis. Specifically, the region of Ste4p that encodes several of the dominant negative, signaling-defective mutations would be an excellent target for cassette mutagenesis when looking for coupling of yeast Gβγ to specific mammalian Gα subunits.

V. Test Compounds

Exogenously added compounds

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. J. Am. Chem. Soc. 114:10987; DeWitt et al. 1993. Proc. Natl. Acad. Sci. USA 90:6909) peptoids (Zuckermann. 1994. J. Med. Chem. 37:2678) oligocarbamates (Cho et al. 1993. Science. 261:1303), and hydantoins (DeWitt et al. supra). Rebek et al. have described an approach for the synthesis of molecular libraries of small organic molecules with a diversity of 104–105 (Carell et al. 1994. Angew. Chem. Int. Ed. Engl. 33:2059; Carell et al. Angew. Chem. Int. Ed. Engl. 1994. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. Anticancer Drug Des. 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. Proc. Natl. Acad. Sci. USA 91:11422; Horwell et al. 1996 Immunopharmacology 33:68; and in Gallop et al. 1994. J. Med. Chem. 37:1233. In addition, libraries such as those described in the commonly owned applications U.S. Ser. No. 08/864,241, U.S. Ser. No. 08/864,240 and U.S. Ser. No. 08/835,623 can be used to provide compounds for testing in the present invention. The contents of each of these applications is expressly incorporated herein by this reference.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223, 409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990)Science 249:404–406); (Cwirla et al. (1990) Proc. Natl. Acad. Sci. 87:6378–6382); (Felici (1991) J. Mol. Biol. 222:301–310); (Ladner supra.).

In certain embodiments, the test compounds are exogenously added to the yeast cells expressing a recombinant receptor and compounds that modulate signal transduction via the receptor are selected. In other embodiments, the yeast cells express the compounds to be tested. For example, a culture of the subject yeast cells can be further modified to collectively express a peptide library as described in more detail in PCT Publication WO 94/23025 the contents of which is expressly incorporated herein by this reference.

Other types of peptide libraries may also be expressed, see, for example, U.S. Pat. Nos. 5,270,181 and 5,292,646; and PCT publication WO94/ 02502). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

Peptide Libraries

In certain embodiments, yeast cells can be engineered to produce the compounds to be tested. This assay system has the advantage of increasing the effective concentration of the compound to be tested. In one embodiment, a method such as that described in WO 94/23025 can be utilized.

Other methods can also be used. For example, peptide libraries are systems which simultaneously display, in a form which permits interaction with a target, a highly diverse and numerous collection of peptides. These peptides may be presented in solution (Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990)Science 249:404–406); (Cwirla et al. (1990) Proc. Natl. Acad. Sci. 87:6378– 6382); (Felici (1991) J. Mol. Biol. 222:301–310); (Ladner supra.). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

The Ladner et al. patent, U.S. Ser. No. 5,096,815, describes a method of identifying novel proteins or polypeptides with a desired DNA binding activity. Semi-random ("variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene is under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., J Biol. Chem.(1989) 264, 20206 and Kaiser et al. (1987) Science 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library.

While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins (see, for example, U.S. Pat. Nos. 5,270,181 and 5,292,646; and PCT publication WO94/ 02502). The combinatorial peptide can be attached one the terminus of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does 10 not reflect any extraneous sequences which may be present in order to facilitate expression, e.g., such as signal sequences or invariant portions of a fusion protein.

In another embodiment, the peptide library is derived to express a combinatorial library of polypeptides which are based at least in part on a known polypeptide sequence or a portion thereof (not a cDNA library). That is, the sequences of the library is semi-random, being derived by combinatorial mutagenesis of a known sequence. See, for example, Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461. Accordingly, polypeptide(s) which are known ligands for a target receptor can be mutagenized by standard techniques to derive a variegated library of polypeptide sequences which can further be screened for agonists and/or antagonists. For example, the surrogate ligand identified for FPRL-1, e.g., the Ser-Leu-Leu-Trp-Leu-Thr-Cys-Arg-Pro-Trp-Glu-Ala-Met peptide, can be mutagenized to generate a library of peptides with some relationship to the original tridecapeptide. This library can be expressed in a reagent cell of the present invention, and other receptor activators can be isolated from the library. This may permit the identification of even more potent FPRL-1 surrogate ligands.

Alternatively, the library can be expressed under conditions wherein the cells are in contact with the original tridecapeptide, e.g., the FPRL-1 receptor is being induced by that surrogate ligand. Peptides from an expressed library can be isolated based on their ability to potentiate the induction, or to inhibit the induction, caused by the surrogate ligand. The latter of course will identify potential antagonists of chemoattractant receptors. In still other embodiments, the surrogate ligand can be used to screen exogenous compound libraries (peptide and non-peptide) which, by modulating the activity of the identified surrogate, will presumably also similarly effect the native ligand's effect on the target receptor. In such embodiments, the surrogate ligand can be applied to the cells, though is preferably produced by the reagent cell, thereby providing an autocrine cell.

In still another embodiment, the combinatorial polypeptides are produced from a cDNA library.

In a preferred embodiment of the present invention, the yeast cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

In embodiments in which the test compounds it may be desirable to express such peptides in the context of a leader sequence. Yeast cells are bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the a-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention. The present invention does not require periplasmic secretion, or, if such secretion is provided, any particular secretion signal or transport pathway.

VI. Screening and Selection

The ability of particular test compounds to modulate a signal transduction activity of the receptor of interest can be scored for by detecting up or down-regulation of a detection signal. For example, alterations in the endogenous yeast second messenger generation (e.g. GTPase activity, phospholipid hydrolysis, or protein phosphorylation patterns or enzyme activity) can be measured directly. Alternatively, the use of an indicator gene or a heterologous reporter gene can provide a convenient readout. In any event, a change in the detection signal can be used to facilitate identification of compounds which modulate signaling via the receptor.

Second Messenger Production

In certain embodiments, changes in intracellular second messenger pathways can be detected biochemically, i.e., by measuring changes in second messengers produced by the modulation of an endogenous yeast signaling pathway. For example, changes in intracellular $Ca^{+2}$, phophorylation states of proteins, activities of intracellular enzymes, and the like can be detected. Still other detection techniques include micorphysiometric devices which permit detection of small changes in, e.g., ions or intracellular pH. In other exemplary embodiments, modulation of, e.g., adenylyl cyclase, cyclic GMP, phosphodiesterases, phosphoinositidases, phosphoinositol kinases, and phospholipases, as well as a variety of ions can be assayed.

In one embodiment, the GTPase enzymatic activity by G proteins can be measured in plasma membrane preparations by determining the breakdown of $\gamma^{32}P$ GTP using techniques that are known in the art (For example, see *Signal Transduction: A Practical Approach*. G. Milligan, Ed. Oxford University Press, Oxford England). When receptors that modulate cAMP are tested, it will be possible to use standard techniques for cAMP detection, such as competitive assays which quantitate [$^3$H]cAMP in the presence of unlabelled cAMP.

Certain receptors and ion channels stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In other embodiments, e.g., in the case of certain receptors and ion channels, it may be desirable to screen for changes in cellular phosphorylation. Such assay formats may be useful when the receptor of interest is a receptor kinase or phosphatase. For example, immunoblotting (Lyons and Nelson (1984) *Proc. Natl. Acad Sci. USA* 81:7426–7430) using anti-phosphotyrosine, anti-phosphoserine or anti-phosphothreonine antibodies. In addition, tests for phosphorylation could be also useful when the receptor itself may not be a kinase, but activates protein kinases or phosphatase that function downstream in the signal transduction pathway.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the *S. cerevisiae* pheromone signaling pathway is comprised of a protein kinase cascade composed of the products of the STE11, STE7, and FUS3/KSS1 senes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

In still other embodiments, the detectable signal can be produced by use of enzymes or chromogenic/fluorescent probes whose activities are dependent on the concentration of a second messenger, e.g., such as calcium, hydrolysis products of inositol phosphate, cAMP, etc. For example, the mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) Environ Health Perspect 84:45–56). As an exemplary method of Ca++ detection, cells could be loaded with the Ca++sensitive fluorescent dye fura-2 or indo-1, using standard methods, and any change in Ca++ measured using a fluorometer.

Detection of Transcription or Transcription Products

In addition to directly measuring second messenger production, the signal transduction activity of a receptor can be measured by detection of a transcription product, e.g., by detecting receptor/channel-mediated transcriptional activation (or repression) of an endogenous gene(s). Detection of the transcription product includes detecting the gene transcript, detecting the product directly (e.g., by immunoassay) or detecting an activity of the protein (e.g., such as an enzymatic activity or chromogenic/fluorogenic activity); each of which is generally referred to herein as a means for detecting expression of the indicator gene. The indicator gene may be an unmodified endogenous gene of the yeast cell or a modified endogenous gene.

In one embodiment, the indicator gene is an unmodified endogenous gene. For example, the instant method can rely on detecting the transcriptional level of such pheromone system pathway responsive endogenous genes as the Bar1 or Fus1, Fus 2, mating factor, Ste3 Ste13, Kex1, Ste2, Ste6, Ste7, sSst2, or Chs1. (Appletauer and Zchstetter. 1989. Eur. J. Biochem. 181:243)

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements. The previous discussion of mutations with regard to G proteins and G protein coupled receptors is reiterated here.

For example, in the case of the Bar1 gene, the promoter of the gene can be modified to enhance the transcription of Bar1 upon activation of the yeast pheromone system pathway. Bar1 gene transcription is iactivated upon exposure of yeast cells to mating factor. The sequence of the Bar1 gene is known in the art (see e.g., U.S. Pat. No. 4,613,572). Moreover, the sequences required for a-factor-enhanced expression of the Bar1, and other pheromone responsive genes have been identified. (Appletauer and Achstetter 1989. Eur. J. Biochem. 181:243; Hagen et al. 1991. Mol. Cell. Biol. 11:2952). In an exemplary embodiment, the yeast Bar1 promoter can be engineered by mutagenesis to be more responsive, e.g., to more strongly promoter gene transcription, upon stimulation of the yeast pheromone pathway. Standard techniques for mutagenizing the promoter can be used. In such embodiments, it is desirable that the conserved oligonucleotide motif described by Appeltaure et al. be conserved.

In another embodiment, the endogenous Bar1 promoter of a yeast cell can be replaced, e.g., by homologous recombination, with a Bar1 promoter engineered to cause higher levels of expression of Bar1 upon pheromone stimulation.

In another exemplary embodiment, the promoter (or other transcriptional regulatory sequences) of the endogenous gene can be "switched out" with a heterologous promoter sequence, e.g., to form a chimeric gene at the indicator endogenous gene locus. Again, using such techniques as homologous recombination, the regulatory sequence can be so altered at the genomic locus of the indicator gene. For example, the Bar1 promoter can be replaced, at the Bar1 locus, with the promoter for the fus1 (or fus2) gene. The fus1 promoter has a higher responsiveness to stimulation by pheromone induction than the Bar1 promoter and, accordingly can increase the signal-to-noise and dynamic range of the indicator gene. For example, the fus1 and fus2 have been substituted for promoters at other loci, such as for the can1 promotor. These strains become canavanine sensitive upon expression of the can1 gene. A similar approach was used to introduce the fus1 and fus2 promoter upstream of the ura3 gene in place of the ura3 promoter, thus conferring uracil prototrophy in a manner dependent on activation of the yeast pheromone signal pathway. Likewise, the fus1 and fus2 promoter regions can be introduced upstream of other genes in order to control their expresion: gal1 (confering deoxygalactose sensitivity or galactose sensitivity due to the concomitant loss of the gal10 gene); β-D-glucanase (exg1: an easily assayed extracellular enzyme); chitinase (cts1); asparaginase (ast3: hydrolyzes asparagine to ammonia and aspartate); and invertase (suc2); secreted acid phosphatase (pho3 or pho5).

In certain embodiments, it may be desirable to increase the level of transcriptional activation of the endogenous indicator gene by the signal pathway in order to, for example, improve the signal-to-noise of the test system, or to adjust the level of response to a level suitable for a particular detection technique. In one embodiment, the transcriptional activation ability of the signal pathway can be amplified by the overexpression of one or more of the proteins involved in the intracellular signal cascade, particularly enzymes involved in the pathway. For example, increased expression of Jun kinases (JNKs) can potentiate the level of transcriptional activation by a signal in an MEKK/JNKK pathway. Likewise, overexpression of one or more signal transduction proteins in the yeast pheromone pathway can increase the level of Fus1, Fus 2 and/or Bar1 expression. This approach can also be used to potentiate the level of transcription of a heterologous reporter gene (described below) as well.

Enzyme Activation

In yet other embodiments, rather than measuring second messenger production or alterations in transcription, the activity of endogenous yeast proteins can be assayed. For example, in one embodiment, the signal transduction pathway of the receptor upregulates expression or otherwise activates an enzyme which is capable of modifying a substrate which can be added to the cell. The signal can be detected by using a detectable substrate, in which case loss of the substrate signal is monitored, or alternatively, by using a substrate which produces a detectable product. In certain embodiments, the substrate is naturally occurring. Alternatively, the substrate can be non-naturally occurring.

In a preferred embodiment, the enzyme which cleaves the substrate peptide is the product of the BAR1 gene, the expression of which is upregulated by stimulation of the yeast pheromone pathway. Thus, yeast cells which have been generated to exploit the pheromone signal pathway for detection can be contacted with a suitable detection means, i.e., a substrate peptide which can be cleaved by BAR1 to release a detectable fragment, e.g. a detectably labeled fragment, and the level of BAR1 activity thus determined.

Alterations in enzyme activity mediated by the interaction of a test compound and a receptor can be detected by a number of means. In preferred embodiments, the conversion of the substrate is measured using a semi-quantitative plate assay to measure BAR1p activity as described in Example 2. As an illustrative embodiment, cells which lack endogenous BAR1 (referred to as a "test yeast strain") can be grown in an appropriate medium. The overnight cultures can then be poured onto medium containing α-factor, allowed to stand a few minutes and poured off. This results in the formation of a confluent and even lawn of test cells. Since the plated lawn of cells lacks the BAR1 gene, it is super-sensitive to α-factor causing its growth to be arrested on the a factor plate. Medium from Bar1-induclibe yeast cells, which have been exposed to test compounds, can be tested for its ability to allow growth of the Bar1 deficient test yeast cells in the lawn. Growth of the lawn of cells indicates that BAR1 is present in the medium and, therefore, that the pheromone system of the Bar1-inducible yeast cell has been modulated by contact with the test compound. Using this assay 2-fold differences in BAR1 activity over a 100-fold concentration range can be distinguished.

In more preferred embodiments, the conversion of the substrate to product by the enzyme produces a detectable change in optical characteristics of the test cell, e.g., the substrate and/or product is chromogenically or fluorogenically active. In an illustrative embodiment the signal transduction pathway causes a change in the activity of a proteolytic enzyme, altering the rate at which it cleaves a substrate peptide (or simply activates the enzyme towards the substrate). The substrate peptide can include a fluorogenic donor radical, e.g., a fluorescence emitting radical, and an acceptor radical, e.g., an aromatic radical which absorbs the fluorescence energy of the fluorogenic donor radical when the acceptor radical and the fluorogenic donor radical are covalently held in close proximity. See, for example, U.S. Ser. Nos. 5,527,681, 5,506,115, 5,429,766, 5,424,186, and 5,316,691; and Capobianco et al. (1992) Anal Biochem 204:96–102. For example, the substrate peptide has a fluorescence donor group such as 1-aminobenzoic acid (anthranilic acid or ABZ) or aminomethylcoumarin (AMC) located at one position on the peptide and a fluorescence quencher group, such as lucifer yellow, methyl red or nitrobenzo-2-oxo-1,3-diazole (NBD), at a different position near the distal end of the peptide. A cleavage site for the activated enzyme will be disposed between each of the sites for the donor and acceptor groups. The intramolecular resonance energy transfer from the fluorescence donor molecule to the quencher will quench the fluorescence of the donor molecule when the two are sufficiently proximate in space, e.g., when the peptide is intact. Upon cleavage of the peptide, however, the quencher is separated from the donor group, leaving behind a fluorescent fragment. Thus, activation of the enzyme results in cleavage of the detection peptide, and dequenching of the fluorescent group. In a preferred embodiment the substrate used to assay for BAR1 activity is conjugated to a fluorescent donor, such as, 5-[(2-aminoethyl)amino]naphthalene-1-sulfonic acid (EDANS), and a quenching acceptor, such as 4-(4-dimethylaminophenylazo)benzoic acid (DABCYL). In a preferred embodiment, the substrate consists of a peptide containing the BAR1p recognition sequence with a (EDANS), and (DABCYL), attached at the COOH— and NH$_2$-termini, respectively. In another embodiment the substrate further comprises a GABA group between the EDANS group and the first amino acid at the COOH terminus (e.g., the Trp residue). The intrinsic fluorescence of EDANS is expected to be dramatically reduced in this substrate because of intramolecular fluorescence resonance energy transfer (FRET) to the DABCYL group. Since FRET becomes insignificant beyond distances of 100 A, the fluorescence of EDANS is restored after cleavage of the substrate (Matayoshi et al, *Science,* 1990 247:954). Thus, proteolytic activity can be continuously monitored by recording the increase in fluorescence intensity with time.

Alternatively, a benzamidine, benzyloxycarbonyl (Cbz) group can be attached at the N-terminus of the substrate and a Rhodamine group at the C terminus of the substrate. Free Rhodamine or mono-substituted Rhodamine exists primarily as a highly fluorescent quinone. However, bis-substituted Rhodamine exists as a virtually non-fluorescent lactone (McGrath et al, *Virology,* 1996 217:131). Thus, the bis-substituted BAR1p substrate has very little fluorescence. The peptides on the substrate are protected from cleavage by aminopeptidases. Cleavage of the peptide with BAR1p, renders the residual Rhodamine-attached peptide susceptible to aminopeptidase cleavage. Aminopeptidase removal of the peptide from Rhodamine will result in production of highly fluorescent mono-substituted and free Rhodamine molecules.

In one embodiment, the substrate to be assayed is naturally occurring yeast (α-factor. In a preferred embodiment a substrate comprises the compound:

DABCYL-Trp-Leu-Gln-Leu-Lys-Pro-Gly-Gln-Pro-Met-Tyr- EDANS (SEQ ID NO:4)

In yet another embodiment a preferred substrate comprises the compound:

Cbz-Trp-Leu-Gln-Leu-Lys-Pro-Gly-Gln-Pro-Met-Tyr-NH$_2$-Rhodamine (SEQ ID NO:5).

Zymogen activation

In an additional embodiment, Bar1 activity can be measured by detecting the activation of an enzyme precursor to an active enzyme. Zymogens are enzyme precursors which become active upon specific, limited proteolytic treatment. In making a zymogen substrate for use in the instant assays, a Bar1 sensitive site (e.g. the sequence of approx. 9–10 amino acids from yeast alpha factor including the Leu-Lys sequence) is introduced between the precursor pro-region of a zymogen and the mature (active) protein sequence by standard genetic engineering techniques. Treatment of the zymogen with Bar1p then releases active enzyme from the zymogen. Using this method of detection, yeast cells, or supernatants from yeast cells, which have been stimulated by a compound to produce Bar1 can be tested by measuring the conversion of zymogen to active enzyme, e.g., by detecting cleavage of a substrate which is sensitive to cleavage by the active enzyme. Examples of zymogens which may be useful in such assays include trypsinogen, plasminogen, prothrombin, pepsinogen, fibrinogen and yeast carboxypeptidase Y and methods of assaying for the activity of the active enzymes derived from these zymogens are well known in the art.

The above system can also be adapted for intracellular zymogen processing. In an exemplary embodiment, the Bar1 protease may be expressed cytoplasmically by excision of the sequences necessary for secretion from the gene resulting in intracellular expression of the mature Bar1 protein. Cells expressing this intracellular Bar1p are then engineered to coexpress an intracellular zymogen with a Bar1p sensitive cleavage and activation site as described above.

To detect Bar1p activity, i.e., conversion of the zymogen to active enzyme, several assays can be used. For example, the bacterial Lac alpha fragment can be fused with a large peptide or a protein. Such a fusion renders Lac alpha incapable of complementation with the Lac omega fragment. (This complementation is the basis of the blue-white discrimination of in frame insertion clones in Lac alpha vectors). However, if such a Bar1 sensitive site is included proximal to the Lac alpha-peptide fusion junction, treatment with Bar1p will release the functional Lac alpha peptide which is now capable of Lac alpha-omega complementation. Thus, Bar1 activity can be read out as a color change in the cell. Beta galactosidase enzyme activity can be detected and measured by any of a wealth of commonly used methods, the most preferred being a chromogenic assay based on indigo dye formation on treatment of the X-gal substrate. In another embodiment, this system may be incorporated into the zymogen embodiment above, allowing both beta-galactosidase and zymogen readouts.

Substrate Stability

In yet another embodiment of an assay which is based on the detection of modulation of enzyme activity, an enzyme substrate may be modified such that cleavage by the enzyme results in destabilization of the substrate (an example of which is described further in Example 5). For example, proteins with Lys at their N-terminus are unstable in yeast (Bachmair and Varshavsky. 1989. Cell. 56:1019). Accordingly, an enzyme substrate which will be cleaved to expose an N-terminal Lys can be fused to an easily assayed detection protein. For instance, the BAR1 substrate, α-factor, can be fused to a detectable gene, e.g. a lacZ gene. In preferred embodiments, it may be desirable to modify the endogenous BAR1 gene, to remove signals for secretion (present at the N and C-terminus of BAR1), thereby enhancing interaction of BAR1 with cytoplasmic substrates. In certain embodiments, the detection protein is an essential protein, thus providing negative selection for BAR1 expression or activity. In other embodiments, a repressor protein can be used as the detection protein, thereby providing a positive readout.

The Use of Chimeric Constructs to Make Endogenous Genes Pheromone Responsive

In yet another embodiment chimeric constructs can be used confer pheromone-responsiveness on endogenous yeast genes that are not normally pheromone-responsive as described in Example 6. Such constructs comprise a segment of a gene encoding a pheromone inducible transcription factor, such as the Ste12p transcription factor. For example, in the presence of pheromone signaling, Ste12p becomes a potent transcriptional activator of genes whose promoters contain a well-defined DNA binding site (the pheromone response element, or PRE). The chimericconstructs further comprise a second segment, encoding a DNA binding domain that binds a DNA sequence in the promoter of the endogenous gene on which pheromone responsiveness is to be conferred. The gene from which the second segment is derived will be selected based on the desired readout. For example, if the assay is to be constructed using gene A as the readout (because of the ease of assaying for the product of gene A), then the second segment of the chimeric construct encodes a DNA binding domain which binds to the gene A promoter and induces expression of gene A which is to be assayed. For example, in a preferred embodiment, the second segment of the construct encodes the DNA binding domain of Pho4p. Wild-type Pho4p binds and activates the promoter of the PHO5, a secreted alkaline phosphatase gene. Upon expression of the chimeric construct, signaling through the pheromone response pathway will activate the Pho4-Ste12 fusion protein encoded by the chimeric construct, and then this Pho4-Ste12 fusion protein will bind to the Pho4 binding site in the Pho5 promoter and induce expression of the PHO5 gene.

In assays employing chimeric constructs, the modulation of a receptor by a test compound will result in a change in the transcription of a gene, which is not normally pheromone responsive. In preferred embodiments, the gene is easily detectable. For example, in a preferred embodiment, the subject assay can be used to measure Pho5, a secreted acid phosphatase. Acid phosphatase activity can be measured using standard techniques. For example, the overlay assay of Toh-e et al (*J. Bacteriol*, 1973) can be used. For example, cells are patched onto the appropriate medium and allowed to grow overnight. For each plate, a mixture of 2 ml of molten 1% agarose in 50 mM NaAc pH 4.0, 700 $\mu$l H$_2$O, and 300 $\mu$l α-napthyl acid phosphate (50 mg/ml) is prepared and applied to the plate. Then 1 ml of D-dianisidine fast blue salt B (50mg/ml in 50 mM NaAc pH 4.0) is poured onto the plate. The degree of color development is a measure of the level of acid phosphatase produced by the patch of cells. Such color development is indicative of the modulation of a receptor by a test compound.

In certain embodiments, such chimeric constructs will further comprise a nuclear localization sequence.

As indicated above, in preferred embodiments the DNA binding domain of the construct (i.e., encoded by the second segment of the construct) from the PHO4 DNA binding domain. The sequence of the PHO4 DNA binding domain is known in the art. The construct can comprise a segment of the naturally occurring PHO4 gene, or can comprise a segment which is derived from the naturally occurring PHO4 gene, but which has been altered, e.g., by mutation. In preferred embodiments, the second gene segment encodes amino acids 227–312 of the PHO4 DNA binding domain.

In other preferred embodiments the pheromone-inducible transcription factor (i.e., encoded by the first gene segment of the construct) is derived from the Ste12 gene. Any of a number of Ste12 fragments can be used in the subject constructs. The sequence of Ste12 is known in the art. There are several sources of information regarding the sequence of Ste12 that the skilled artisan can refer to when selecting the segment of Ste12 to incorporate into the chimeric construct. For example, fusions have been made between the Gal4 DNA binding domain and different regions of Ste12 (Song et al Genes & Development, 1991). Additionally, deletion and insertion mutants of Ste 12 have been constructed and tested for their ability to restore mating and transcriptional activity to a ste12Δ strain (Kirkman-Correia et al Mol Cell Biol, 1993). Such experiments provide guidance as to portions of Ste 12 which can be incorporated into the constructs and which portions are likely to be amenable to mutation.

The chimeric constructs of the instant invention can comprise a segment derived from a naturally DNA sequence, or the subject constructs can comprise a segment which is homologous to a naturally occurring gene, but which has been altered, e.g., by mutation. Any of the standard methods of making mutations which are known in the art or discussed herein can be used for this purpose.

For example, in preferred embodiments, the first gene segment which is incorporated into the construct comprises a nucleotide sequence which encodes amino acids 1–473 of the naturally occurring Ste12. In another embodiment, the construct comprises a nucleotide sequence which encodes amino acids 214–473 of naturally occurring Ste12. In another embodiment, the construct comprises a nucleotide sequence encoding amino acids 214–688 of naturally occurring Ste 12. In yet another embodiment, the construct comprises a nucleotide sequence encoding amino acids 1–688 of naturally occurring Ste12.

In yet other embodiments, the segment of the construct derived from the Ste 12 gene can comprise a mutation. For example, in one embodiment, such a mutation can result in the insertion of one or more amino acids, e.g., the insertion of Lys-Leu between amino acids 85 and 86 of Ste12. In another embodiment, such a mutation can result in an insertion of Ser-Leu between amino acids 103 and 104. In yet another embodiment one or more amino acids can be deleted, for example, amino acids 253–305, 572–669, or 588–669.

In preferred embodiments, the endogenous yeast gene which corresponds to a gene present in the construct is disrupted. For example, in preferred embodiments, yeast cells bearing a Ste12-PHO4 construct can be engineered such that the PHO4 gene of the host yeast cell can be disrupted. In other preferred embodiments, the PHO3 gene, which also encodes a secreted acid phosphatase, but which is induced under high-phosphate conditions and is further increased by thiamine starvation, can be disrupted.

Heterologous Readouts: Reporter Gene Constructs

In yet other embodiments, a heterologous gene construct can be used to detect the modulation of a receptor. By selecting transcriptional regulatory sequences that are responsive to the transduced intracellular signals and operatively linking the selected promoters to reporter genes, whose transcription or translation is readily detectable and measurable, a transcription based assay provides a rapid indication of whether a specific receptor interacts with a test compound in any way that modulates intracellular transduction. Expression of the reporter gene, thus, provides a valuable screening tool for the development of compounds that act as agonists or antagonists of such a receptor.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on receptor signaling. Typically, the reporter gene construct will include a reporter gene in operative linkage with one or more transcriptional regulatory elements responsive to the signal transduction activity of the target receptor, with the level of expression of the reporter gene providing the receptor-dependent detection signal. In either embodiment, the amount of transcription from the indicator gene may be measured using any method known to those of skill in the art to be suitable.

In preferred embodiments, the product of the reporter gene is detected by an intrinsic activity associated with that product. For instance, the indicator gene may encode a gene product that, by enzymatic activity, gives rise to a detection signal based on, for example, color, fluorescence, or luminescence.

The amount of expression from the reporter gene is then compared to the amount of expression in either the same cell in the absence of the test compound or it may be compared with the amount of transcription in a substantially identical cell that lacks the specific receptors. A control cell may be derived from the same cells from which the test cell was prepared but which had not been treated with the compound. Alternatively, it may be a cell in which the receptor of interest is not present. Any change in the amount of transcription (e.g., a statistically significant change) indicates that the test compound has in some manner altered the activity of the specific receptor or ion channel.

In other preferred embodiments, the reporter gene provides a selection method such that cells in which activation (or inactivation) of one or more signal pathways of a receptor or ion channel provides a growth advantage to the treated cell. For example, expression of the indicator gene could enhance cell viability, relieve a cell nutritional requirement, and/or provide resistance to a drug.

Many exemplary reporter genes and transcriptional regulatory elements are known to those of skill in the art and others may be identified or synthesized by methods known to those of skill in the art. Such examples of reporter genes include, but are not limited to CAT (chloramphenicol acetyl transferase) (Alton and Vapnek (1979), Nature 282:864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1:4154–4158; Baldwin et al. (1984), Biochemistry 23:3663–3667); alkaline phosphatase (Toh et al. (1989) Eur. J. Biochem. 182:231–238, Hall et al. (1983) J. Mol. Appl. Gen. 2:101), human placental secreted alkaline phosphatase (Cullen and Malim (1992) Methods in Enzymol. 216:362–368); β-lactamase or GST.

Transcriptional control elements for use in the reporter gene constructs, or for modifying the genomic locus of an indicator gene include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4:477–485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In the case of receptors which modulate cyclic AMP, a transcriptional based readout can be constructed using the cyclic AMP response element binding protein, CREB, which is a transcription factor whose activity is regulated by phosphorylation at a particular serine (S133). When this serine residue is phosphorylated, CREB binds to a recognition sequence known as a CRE (cAMP Responsive Element) found to the 5' of promotors known to be responsive to elevated cAMP levels. Upon binding of phosphorylated CREB to a CRE, transcription from this promoter is increased.

Phosphorylation of CREB is seen in response to both increased cAMP levels and increased intracellular Ca levels. Increased cAMP levels result in activation of PKA, which in turn phosphorylates CREB and leads to binding to CRE and transcriptional activation. Increased intracellular calcium levels results in activation of calcium/calmodulin responsive kinase II (CaM kinase II). Phosphorylation of CREB by CaM kinase II is effectively the same as phosphorylation of CREB by PKA, and results 20 in transcriptional activation of CRE containing promoters.

A transcriptionally-based readout can be constructed in cells containing a reporter gene whose expression is driven by a basal promoter containing one or more CRE. Changes in the intracellular concentration of $Ca^{++}$ (a result of alterations in the activity of the receptor upon engagement with a ligand) will result in changes in the level of expression of the reporter gene if: a) CREB is also co-expressed in the cell, and b) either an endogenous or heterologous CaM kinase phosphorylates CREB in response to increases in calcium or if an exogenously expressed CaM kinase II is present in the same cell. In other words, stimulation of PLC activity may result in phosphorylation of CREB and increased transcription from the CRE-construct, while inhibition of PLC activity may result in decreased transcription from the CRE-responsive construct.

As described in Bonni et al. (1993) Science 262:1575–1579, the observation that CNTF treatment of SK-N-MC cells leads to the enhanced interaction of STAT/p91 and STAT related proteins with specific DNA sequences suggested that these proteins might be key regulators of changes in gene expression that are triggered by CNTF. Consistent with this possibility is the finding that DNA sequence elements similar to the consensus DNA sequence required for STAT/p91 binding are present upstream of a number of genes previously found to be induced by CNTF (e.g., Human c-fos, Mouse c-fos, Mouse tis 11, Rat junB, Rat SOD-1, and CNTF). Those authors demonstrated the ability of STAT/p91 binding sites to confer CNTF responsiveness to a non-responsive reporter gene. Accordingly, a reporter construct for use in the present invention for detecting signal transduction through STAT proteins, such as from cytokine receptors, can be generated by using −71 to +109 of the mouse c-fos gene fused to the bacterial chloramphenicol acetyltransferase gene (−71fosCAT) or other detectable reporter gene. Induction by a cytokine receptor induces the tyrosine phosphorylation of STAT and STAT-related proteins, with subsequent translocation and binding of these proteins to the STAT-RE. This then leads to activation of transcription of genes containing this DNA element within their promoters.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the reporter may be distinguished from those which do not. Selection is preferable to screening in that it can provide a means for amplifying from the cell culture those cells which express a test polypeptide which is a receptor effector.

The reporter gene is coupled to the receptor signaling pathway so that expression of the reporter gene is dependent on activation of the receptor. This coupling may be achieved by operably linking the reporter gene to a receptor-responsive promoter. The term "receptor-responsive promoter" indicates a promoter which is regulated by some product of the receptor's signal transduction pathway.

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor- induced promoter to a gene encoding mRNA which is antisense to at least a portion of the mRNA encoded by the reporter gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the reporter gene.

In the case of yeast, suitable positively selectable (beneficial) genes include the following: URA3, LYS2, HIS3, LEU2, TRP1; ADE1,2,3,4,5,7,8; ARG1, 3, 4, 5, 6, 8; HIS1, 4, 5; ILV1, 2, 5; THR1, 4; TRP2, 3, 4, 5; LEU1, 4; MET2,3,4,8,9,14,16,19; URA 1,2,4,5,10, HOM3,6; ASP3; CHO1; ARO 2,7; CYS3; OLE1; IN01,2,4; PR01,3 Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In a more complex version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on α-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanin), and other recessive drug-resistant markers.

In one example, the reporter gene effects yeast cell growth. The natural response to signal transduction via the yeast pheromone system response pathway is for cells to undergo growth arrest. This is the preferred way to select for antagonists to a ligand/receptor pair that induces the pathway. An autocrine peptide antagonist would inhibit the activation of the pathway; hence, the cell would be able to grow. Thus, the FAR1 gene may be considered an endogenous counterselectable marker. The FAR1 gene is preferably inactivated when screening for agonist activity.

The reporter gene may also be a screenable gene. The screened characteristic may be a change in cell morphology, metabolism or other screenable features. Suitable markers include beta-galactosidase (Xgal, $C_{12}$FDG, Salmon-gal, Magenta-Gal (latter two from Biosynth Ag)), alkaline phosphatase, horseradish peroxidase, exo-glucanase (product of yeast exb1 gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable reporter gene is beta-galactosidase; yeast cells expressing the enzyme convert the colorless substrate Xga1 into a blue pigment. Again, the promoter may be receptor-induced or receptor-inhibited.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, this normal response of growth arrest can be used to select cells in which the pheromone response pathway is inhibited. That is, cells exposed to a test compound will be growth arrested if the compound is an agonist, but will grow normally if the compound is neutral or an antagonist. Thus, the growth arrest response can be used to advantage to discover compounds that function as agonists or antagonists. Moreover, the effect of growth arrest can provide a selective advantage in the presence of an agent which is cytotoxic to mitotic cells. For example, during the growth arrest window, the cytotoxic agent is added to the culture. Cells which proceed through the cell-cycle, e.g., which are not growth arrested, will be killed. At some time after the addition of the cytotoxic agent, it can be washed from the culture, and surviving cells permitted to proceed with proliferation. Cells which were arrested by the test compound will be enriched in the surviving population.

However, in certain embodiments (particularly those in which an autocrine peptide library is employed), the growth arrest consequent to activation of the pheromone response pathway is an undesirable effect since cells that bind agonists stop growing while surrounding cells that fail to bind peptides will continue to grow. The cells of interest, then, will be overgrown or their detection obscured by the background cells, confounding identification of the compound of interest. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

It is desirable that the exogenous receptor be exposed on a continuing basis to the peptides. Unfortunately, this is likely to result in desensitization of the pheromone pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) Mol. Cell. Biol. 13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1,Bar1, ste2,ste3,pik1,msg5, sig1 , and aft1, have the similar effect of increasing the sensitivity of the bioassay. Thus desensitization may be avoided by mutating (which may include deleting) the SST2 gene so that it no longer produces a functional protein, or by mutating one of the other genes listed above.

If a test compound fails to stimulate the activity of a receptor, the assay may be repeated and modified by the introduction of a step in which the reagent cell is first contacted with a known activator of the target receptor/channel to induce signal transduction, and the test compound can be assayed for its ability to inhibit the activated receptor/channel, e.g., to identify antagonists. In yet other embodiments, batteries of compounds can be screened for agents which potentiate the response to a known activator of the receptor.

XII. Genetic Markers in Yeast Strains

Yeast strains that are auxotrophic for histidine (HIS3) are known, see Struhl and Hill, (1987) Mol. Cell. Biol., 7:104; Fasullo and Davis, *Mol. Cell. Biol.*, (1988) 8:4370. The HIS3 (imidazoleglycerol phosphate dehydratase) gene has been used as a selective marker in yeast. See Sikorski and Heiter, (1989) Genetics, 122:19; Struhl, et al., P.N.A.S. (1979) 76:1035; and, for FUS1-HIS3 fusions, see Stevenson, et al., (1992) Genes Dev., 6:1293.

XIII. Pharmaceutical Preparations of Identified Agents

After identifying certain test compounds in the subject assay ,e.g.,as potential surrogate ligands, or receptor antagonists, the practioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

Exemplification

The invention now being generally described will be more readily understood by reference to the following examples, which are included merely for purposes of illustration of certain aspects and embodiments of the present invention and are not intended to limit the invention. All patents, published patent applications and other references disclosed herein are hereby expressly incorporated by reference.

Example 1

Development of Assays for Bar1 Protease Activity

This example describes the development of assays to facilitate the use of the Bar1 protease as a readout for induction of the pheromone-response pathway in *S. cerevisiae*. The *S. cerevisiae* BAR1 gene encodes a protease that recognizes and cleaves the yeast α-factor peptide pheromone. Bar1p cleaves the mature 13 amino acid α-factor peptide between residues 6 and 7 (Leu-Lys), rendering the pheromone inactive. Bar1p has three features that make it potentially useful as a readout system: (1.) The BAR1gene is induced by signaling through the pheromone-response pathway, (2.) Bar1p is secreted, and (3.) Bar1p is a catalytic enzyme, allowing signal amplification (Reviewed by Sprague and Thorner in The Molecular and Cellular Biology of the Yeast Scaaharomyces. Vol. 2. 1992).

Strain Construction

To facilitate development of an assay for Bar1p activity, the BAR1 gene was cloned into two yeast expression plasmids. One, a low copy number vector in which the gene is under its own promoter and the other, a high copy number vector in which the gene is driven by the strong constitutive *S. cerevisiae* PGK promoter. Both plasmids contain the *S. cerevisiae* LEU2 gene to maintain selection in yeast. The primers:

1- 5' CTAATCTCGAGTTAAGAAGGCCGTT 3' (SEQ ID NO:1) and

2- 5' GTTAAGGATCCTGTACTCCAGATTT 3' (SEQ ID NO:2)

were used to amplify bases 31 480 to 1760 of the BAR1 gene from yeast genomic DNA. The amplified product bears an Xho1 site at its 5' end, a BamH1 site at its 3' end, and contains the complete Bar1 open reading frame as well as all of the promoter elements known to influence BAR1 expression (Kronstad et al. Cell. 1987). The product was digested with Xho1 and BamH1 and subcloned into a yeast expression vector (pRS415, referred to herein as Cadus 10 14; see e.g., Sikorski and Hieter. 1989. Genetics. 122:19) that had been digested with Xho1 and BamH1. The resulting plasmid was designated Cadus 3974.

To create the PGK-BAR1 expression plasmid, primer #2 and primer

3- 5' GATATCGTCTCACATGTCTGCAATTA 3'(SEQ ID NO:3)

were used to amplify sequences encoding just the BAR1 open reading frame from the PCR product described above. The product bears a BsmB1 site (digestion with BsmBI results in an NcoI compatable overhang) at its 5' and a BamH1 site at its 3' end. The product was digested with BsmB1 and BamH1 and subcloned into Cadus 1651 that had been digested with Nco1 and BamH1. The resulting plasmid was designated Cadus 3975.

Cadus 1014, 3974, 1651, and 3975 were introduced into Cadus 579 (MATa Bar1::hisG::URA3 trp1 leu2 ura3 his3 FUS1::HIS3 ste14::TRP1), a yeast strain that lacks its own copy of the BAR1 gene.

Bar1 Plate Assay

A semi-quantitative plate assay was used to measure Bar1p activity. Although Bar1p from any source can be used in this assay, in this example Bar1p produced by CY 11362 (Cadus 579 containing Cadus 397) was used. CY 11362 cells were grown to stauration overnight in SD LEU- medium. The cells were removed from the culture by filtration. The activity of Bar1p in the conditioned media was measured by spotting 2 μl onto a Bar1 assay plate (described below). To determine the sensitivity of the assay, eight two-fold serial dilutions of the conditioned medium were made and 5 μl of each dilution was applied to the assay plate.

Assay plates were prepared as follows. CY 579 cells were grown overnight in YEPD medium. The overnight cultures were diluted to $OD_{600}$ 0.1 and allowed to grow a few hours (to $OD_{600}$ 0.4). The cells were then diluted to $OD_{600}$ 0.1 in $H_2O$ and 5 ml were poured onto a YEPD+α-factor plate (1 μg α-factor spread evenly on the surface of a YEPD plate just prior to use), allowed to stand a few minutes and poured off. This results in the formation of a confluent and even lawn of cells on the YEPD+α-factor plate. The conditioned media was then applied to the assay plate and the plate was incubated at 30° C. for 1–2 days.

Since CY 579 lacks the BAR1 gene, it is super-sensitive to α-factor causing its growth to be arrested on the YEPD+ α-factor plate. If the conditioned media applied to the lawn contains Bar1p activity, the α-factor in that region is destroyed, allowing growth of the CY 579 cells.

Using this assay 2-fold differences in Bar1 activity over a 100-fold concentration range can be distinguished. Thus, this assay is useful for assessing activation of the pheromone response pathway in cells expressing only the endogenous BAR1 gene. The series of serial dilutions of CY 11362 conditioned media described in this example are used to generate a standard curve and thus to provide a semi-quantitative assay for Bar1p activity. For this purpose, a large pool of CY 11362 conditioned media was prepared and aliquots were frozen for use in subsequent experiments.

Fluorescent Bar1 Substrates

Two novel fluorescent substrates have been designed to monitor activity of the Bar1p protease in liquid assays that are amenable to high-throughput screening. Each of these substrates includes the Bar1p peptide-recognition sequence and has been designed such that cleavage by Bar1 results in a pronounced fluorescence signal. The first substrate, DABCYL-(GABA)-Trp-Leu-Gln-Leu-Lys-Pro-Gly-Gln-Pro-Met-Tyr-EDANS (SEQ ID NO: 4)

Is based on a substrate for the HIV-1 protease (Matayoshi et al, *Science,* 1990). The substrate consists of an peptide containing the Bar1p recognition sequence with a fluorescent donor, 5-[(2-aminoethyl)amino]naphthalene-1-sulfonic acid (EDANS), and a quenching acceptor, 4-(4-dimethylaminophenylazo)benzoic acid (DABCYL), attached at the COOH— and NH$_2$-termini, respectively. The intrinsic fluorescence of EDANS is expected to be dramatically reduced in this substrate because of intramolecular fluorescence resonance energy transfer (FRET) to the DABCYL group. Since FRET becomes insignificant beyond distances of 100 Å, the fluorescence of EDANS is restored after cleavage of the peptide (Matayoshi et al, *Science*, 1990).

The second substrate,

Cbz- Trp-Leu-Gln-Leu-Lys-Pro-Gly-Gln-Pro-Met-Tyr-NH)$_2$ -Rhodamine (SEQ ID NO:5)

is based on a substrate for the adenovirus proteinase (McGrath et al, *Virology*, 1996). Free Rhodamine or mono-substituted Rhodamine exists primarily as a highly fluorescent quinone. However, bis-substituted Rhodamine exists as a virtually non-fluorescent lactone (McGrath et al, *Virology*, 1996). Thus, the bis-substituted Bar1p substrate exhibits very little fluoresence. This substrate may be used in a coupled assay, which involves cleavage first by Bar1p and then by an added amino peptidase. The peptides on the substrate are protected from cleavage by aminopeptidases. Cleavage of the peptide with Bar1p, renders the residual Rhodamine-attached peptide susceptible to cleavage by added aminopeptidase. Aminopeptidase removal of the peptide from Rhodamine will result in production of highly fluorescent mono-substituted and free Rhodamine molecules.

Zymogen Activation Assays

In an additional embodiment, Bar1 activity can be measured by assaying the activation of an enzyme precurson to an active enzyme. Zymogens are enzyme precursors which become active upon specific, limited proteolytic treatment. A Bar1 sensitive site (e.g. the sequence of approx. 9–10 amino acids from yeast alpha factor including the Leu-Lys sequence) is introduced between the precursor pro-region of a zymogen and the mature (active) protein sequence by standard genetic engineering techniques. Treatment of the zymogen with Bar1p then releases active enzyme from the zymogen. Using this method of detection, yeast cells, or supernatants from yeast cells, which have been stimulated by a compound to produce Bar1 can be tested for thier ability to activate a zymogen. The zymogen activity is then measured by methods well known by those of skill in the art. Examples of zymogens which may be useful in such assays include trypsinogen, plasminogen, prothrombin, pepsinogen, fibrinogen and yeast carboxypeptidase Y.

The above system can also be adapted for intracellular zymogen processing. The Bar1 protease may be expressed cytoplasmically by excision of the sequences necessary for secretion from the gene resulting in intracellular expression of the mature Bar1 protein. Cells expressing this intracellular Bar1p are engineered to coexpress an intracellular zymogen with a Bar1p sensitive cleavage and activation site as described above.

Fusion of the bacterial Lac alpha fragment with a large peptide or a protein renders it incapable of complementation with the Lac omega fragment. (This is the basis of the blue-white discrimination of in frame insertion clones in Lac alpha vectors). However, if such a fusion of Lac alpha with another peptide or protein has a Bar1 sensitive site proximal to the fusion junction such that treatment with Bar1p releases a functional Lac alpha peptide which is now capable of Lac alpha-omega complementation. Beta galactosidase enzyme activity can be detected and measured by any of a wealth of commonly used methods, the most preferred being a chromogenic assay based on indigo dye-formation on treatment of the X-gal substrate. This system may be incorporated into the zymogen embodiment above, allowing both beta-galactosidase and zymogen readouts.

Example 2

Detection of Ste2p Activation using the Bar1 Plate Assay

This example demonstrates the utility of the Bar1 plate assay for assessing agonist-induced activation of the *S. cerevisiae* pheromone receptor, Ste2p.

Strain Construction

First, the gene encoding the *S. cerevisiae* Gα, GPA 1, was reintroduced into the genome of CY 8034 (MATa gpa1*1162 far1-1 ste2*1154 ste14::trp1::LYS2 fus1-HIS3 ura3 trp1 leu2 lys2 his3 ade2-1 met1) by transformation with an integrating plasmid encoding GPA1 (Cadus 3907), creating CY 11364. Next, the gene encoding the *S. cerevisiae* RGS protein, SST2, was disrupted in this strain to create CY 11645. Since Sst2p is involved in desensitization of the pheromone response pathway, its disruption results in increased signaling through the pathway (Reviewed by Sprague and Thorner in Molecular and Cellular Biology of the Yeast Saccharomyces. Vol. 2. 1992).

A high copy number Ste2 expression plasmid was constructed as follows. The 4.3 kb BamH1 fragment containing the entire STE2 gene was excised from the yeast expression plasmid Yep24-STE2 (obtained from J. Thorner, Univ. of California Berkeley) and cloned into the BamH1 site of pRS425 (Cadus 1018) (Sikorski and Heiter, Genetics. 1989). The resulting plasmid, Cadus 2456, and the vecotr control, Cadus 1018, were then introduced into CY 11645 to create CY 11728 and CY 11727, respectively.

Detection of Ste2p Activation Using the Bar1 Plate Assay

Overnight cultures of CY 11727 and CY 11728 were diluted in SD LEU-medium to an $OD_{600}$ of 0.2 and allowed to grow for a few hours at 30° C. (to $OD_{600}$ 0.4). The cells were collected by centrifugation, washed 1× with SD LEU-medium, and resuspended in 2 ml SD LEU- medium. The cultures were split in half and α-factor (10 µg) was added to one aliquot and vehicle (in this case, H$_2$O) was added to the other. After 2 hours of incubation at 30° C., the cells were removed either by four successive rounds of centrifugation or by filtration, and 5 µl of the conditioned media was applied to a Bar1 assay plate (described in Example 1). A standard curve was also done with each experiment (described in Example 1) to quantitate the results.

Little or no Bar1p activity was detected in conditioned media from cells lacking the Ste2p expression plasmid. In cells expressing Ste2p, exposure to agonist resulted in a greater than 8-fold increase in Bar1p activity. These data indicate that the Bar1 plate assay can be used to detect activation of the *S. cerevisiae* G-protein coupled receptor Ste2p. By analogy, this assay can be used to detect activation of any receptor (including non-homologous e.g. mammalian GPCRs) coupled to the *S. cerevisiae* pheromone response pathway.

Example 3

Detection of Melatonin 1b Receptor Activation in *S. cerevisiae* using the Bar1 Plate Assay This example demonstrates the utility of the Bar1 plate assay for assessing activation of mammalian G-protein coupled receptors that have been coupled to the *S. cerevisiae* pheromone response pathway. For this purpose yeast strains expressing the Melatonin 1b receptor were constructed.

Plasmid and Strain Construction

A plasmid, pcDNA3-hML1b, containing the complete open reading frame of the human Melatonin 1b receptor was used as a convenient source of the gene. The sequence of the Melatonin 1b receptor is known in the art (See e.g., Genbank accession number U25341). Primers 5° CCTCCGGTCTCCCATGTCAGAGAACG-GCTCCTT 3' (SEQ ID NO:6) and

5° CCTCCGGTCTGGGATCCGAGAGCATCT-GCCTGGTGC 3' (SEQ ID NO:7)

were used to amplify the receptor sequences from this plasmid. The amplified product bears BsaI sites on both the 5' and 3' ends. Digestion with BsaI resulted in a product with an NcoI compatable overhang at the 5' end and a BamHI compatable overhang at the 3' end. This product was gel purified and subcloned into Cadus 1651 that had been digested with NcoI and BamHI. The resulting plasmid was designated, Cadus 3693.

Cadus 1651 and 3693 were transformed into CY 11645 (described in Example 2) to create CY 11729 and CY 11730, respectively. To verify that Melatonin 1b receptors expressed in CY 11730 are capable of being activated by agonist and that this activation results in signalling through the pheromone response pathway, the expression of the integrated FUS1-HIS3 reporter was assessed. Lawns of CY 11729 and CY 11730 cells were prepared on SD LEU-HIS-pH 6.8 plates from SD LEU- pH 6.8 overnight cultures as described in Example 1. After preparation of the lawns, Melatonin (20 μg) was spotted onto the plates and the plates were incubated at 30° C. overnight. Only cells that contained the Melatonin 1b expression plasmid (CY 11730) grew and these cells only grew within the zone of diffusion of the applied Melatonin. These data demonstrate the functional expression of the human Melatonin 1b receptor in yeast and the coupling of this receptor to the pheromone response pathway.

Detection of Melatonin 1b Receptor Activation using the Bar1 Plate Assay

Overnight cultures of CY 11729 and CY 11730 were diluted in SD LEU- pH 6.8 medium to an $OD_{600}$ of 0.2, and allowed to grow for a few hours at 30° C. (to $OD_{600\ 0.4}$). The cells were collected by centrifugation, washed 1× with SD LEU- pH 6.8 medium, and resuspended in 2 ml SD LEU- pH 6.8 medium. Melatonin (10 μg) was added to one aliquot and vehicle (in this case, DMSO) was added to the other. After 4 hours of incubation at 30° C., the cells were removed either by four successive rounds of centrifugation or by filtration, and 2 μl of the conditioned media was applied to a Bar1 assay plate (described above). A standard curve was also determined with each experiment to quantitate the results. Little or no Bar1p activity was detected in conditioned media from cells lacking the melatonin 1b receptor expression plasmid.

In several experiments addition of 10 ug melatonin to cells expressing the receptor resulted in approx. 2–8 fold induction of Bar1p. Thus, the Bar1 plate assay can be used to detect activation of a mammalian G-protein coupled receptor in *S. cerevisiae*.

Example 4

Detection of C5a Receptor Activation in *S. cerevisiae* using the Bar1 Plate Assay In this example, C5a receptor activation is assessed using the Bar1 plate assay in a yeast strain expressing the chimeric Gα, $GPA1_{41}$-Gαi3.

Strain Construction

The chimeric Gα, $GPA1_{41}$-Gαi3, was integrated into the GPA1 locus of CY 8034 to create CY 11365. To verify the integration, the expression of the FUS1-HIS3 reporter in CY 8034 and CY 11365 was compared. Since CY 8034 does not express a G α protein, the pheromone response pathway is constitutively active in this strain. Thus, integration of $GPA1_{41}$-Gαi3 would be expected to decrease expression of the reporter. As expected, reporter gene expression was reduced in CY 11365, however, it was not completely eliminated. The residual activity is likely due to incomplete coupling of the $GPA1_{41}$-Gαi3 chimera to the yeast Gβγ.

Cadus 1303, a high copy number yeast expression vector containing the C5a receptor open reading frame fused to the yeast PGK promoter, and Cadus 1289, the vector control, were then transformed into CY 11365 to create CY 11458 and CY 11457, respectively. Expression of the FUS1-HIS3 reporter in these cells using the Merck C5a receptor agonist, CHA—CHA, was assessed as in Example 2. As expected, only cells expressing the C5a receptor (CY 11458) grew on SD LEU-HIS- pH 6.8 plates containing 1 mM aminotriazole and these cells only grew within the zone of diffusion of the applied CHA—CHA.

Detection of C5a Receptor Activation using the Bar1 Plate Assay

Overnight cultures of CY 11457 and CY 11458 were diluted in SD LEU- pH 6.8 medium to an $OD_{600}$ of 0.2, and allowed to grow for a few hours at 30° C. (to $OD_{600\ 0.4}$). The cells were collected by centrifugation, washed 1× with SD LEU- pH 6.8 medium, and resuspended in 2 ml SD LEU- pH 6.8 medium. CHA-CHA (10 μM) was added to one aliquot and vehicle (in this case, DMSO) was added to the other. After 4 hours of incubation at 30° C., the cells were removed either by four successive rounds of centrifugation or by filtration, and 5 μl of the conditioned media was applied to a Bar1 assay plate (described in Example 1). A standard curve was determined with each experiment to quantitate the results. Exposure of cells expressing C5a receptor to CHA—CHA resulted in increased Baar1p activity, although the induction was less than that seen with Ste2p or Melatonin 1b receptors.

Example 5

Detection of Bar1p-mediated protein degradation

This example illustrates an embodiment of the subject assays in which enzyme-mediated cleavage of α-factor by BAR1p can be used to control the stability of a substrate, which can be used as a selectable event. Cleavage of α-factor by BAR1p leaves an N-terminal lysine residue. Proteins with lysine at their N-terminus have been shown to be unstable in yeast (Bachmair and Varshavsky. 1989. Cell. 56:1019). Therefore, chimeric substrate proteins whose stability in yeast is controlled by the levels of BAR1p can be constructed. The α-factor peptide sequence is introduced into the open reading frame of an easily-assayed protein. BAR1p induction then causes cleavage of the α-factor sequence within the chimeric substrate and degradation of the substrate by the N-end rule pathway.

The α-factor peptide sequence is fused to the N-terminus of a model substrate, for example, lacZ using standard recmbinant DNA techniques. The construct is placed under the control of a constitutive, moderately expressed promoter in a yeast expression vector. This vector is introduced into yeast cells in which Bar1p activity can be induced upon stimulation with an appropriate test compound and LacZ (either enzyme activity or protein levels) is then assayed in cells which have been contacted with test compounds. Test compounds that induce Bar1p are selected based on decreased stability of the chimeric LacZ substrate.

In alternative embodiments, Lac Z can be replaced with, for example, an essential gene (to provide negative selection for Bar1p activity) or a repressor protein (to provide positive selection for Bar1p activity).

In certain embodiments of the assay, it may be desirable to remove the signals for secretion present at the N- and C-terminus of BAR1p to thereby inhibit targeting of Bar1p to the secretion machinery. This allows for greater access of Bar1p to the chimeric substrate present in the cytoplasm.

Example 6

Construction of PHO4/STE12 Chimerae

This example describes the construction of yeast expression plasmids encoding a series of PHO4/STE12 chimerae. These chimerae are used make an easily-assayed gene product, the secreted acid phosphatase PhO5p, pheromone inducible. Changes in gene expression as a consequence of pheromone induction are mediated by the Ste12p transcription factor. In the presence of pheromone signaling Ste12p becomes a potent transcriptional activator of genes whose promoters contain a well-defined DNA binding site (the pheromone response element, or PRE) (Reviewed by Sprague and Thorner in The Molecular and Cellular Biology of the Yeast Saccharomyces Vol. 2, 1992). The transcription factor Pho4p is activated when cells are starved for phosphate. Once activated, Pho4p binds to promoter elements in several genes, including Pho5, and induces their transcription (Reviewed by Johnston and Carlson in The Molecular and Cellular Biology of the Yeast Saccharomyces Vol. 2, 1992). Chimeric transcription factors that contain the transcription activation domains of Ste12p have been constructed by fusing regions of Ste12p with the DNA binding domain of Pho4p. Expression of these chimerae in yeast results in induction of Pho5 expression when the pheromone response pathway is activated. This induction is due to stimulation by the Ste12 transcription activation domain brought into proimity with the Pho5 promoter by the Pho4 DNA binding domain. Expression of Pho5 can be easily assessed by several well-defined methods for detecting acid phosphatase activity.

A yeast expression plasmid was constructed that contains the yeast ADH promoter fused to sequences encoding an 11 amino acid nuclear localization signal and the PHO4 DNA binding domain (amino acids 227–312). Sequences encoding the PHO4 DNA binding domain were amplified from yeast genomic DNA using the primers 5° CGACTAAGCTTATGGGTGCACCTC-CTAAAAAGAAGAGAAAGGTAGCCCCG-CACGGATC GAGCCAT 3' (SEQ ID NO:8)

and 5' CCGGAATTCCGTGCTCACGTTC-3'. (SEQ ID NO:9)

The PCR product encodes the Pho4 DNA binding domain flanked by a HindIII site and sequences encoding a nuclear localization signal on its 5' end and an EcoRI site on its 3' end. This product was digested with HindIII and EcoRI and gel purified. Plasmid pCD72 (Cadus 3973) was obtained from Dr. J. Broach. It is a high copy number yeast vector containing the ADH promoter and transcription termination sequences as well as sequences encoding the GAL4 DNA binding domain. Digestion of this plasmid with HindIII and EcoRI results in 3 fragments; one containing the vector backbone and the ADH promoter flanked by HindIII overhangs, a second containing the ADH transcription termination sequences with an EcoRI overhang at its 5' end and a HindIII overhang at its 3' end, and a third containing the GAL4 DNA binding domain with a HindIII overhang at its 5' end and an EcoRI overhang at its 3' end. The first two fragments were gel purified and used in a 3-piece ligation with the digested and gel purified PCR amplification product. The resulting plasmid is designated Cadus 4129.

Fragments of STE12 were subcloned in frame 3' to the Pho4 DNA binding domain and 5' of the ADH transcription termination sequences by using either the EcoRI site, the EcoRI and BamHI sites, or the EcoRI and PstI sites in Cadus 4129. The choice of Ste12 fragments was based on two studies, one in which fusions were made between the Gal4 DNA binding domain and different regions of Ste12 (Song et al *Genes & Development*, 1991) and one in which deletion and insertion mutants of Ste12 were constructed and tested for their ability to restore mating and transcriptional activity to a ste12Δ strain (Kirkman-Correia et al *Mol Cell Biol*, 1993). Plasmids encoding the different Ste12 fragments were obtained from Dr. S. Fields.

| Plasmid | Region of Ste12p (amino acids) |
| --- | --- |
| Cadus 4183 | 1–688 (entire protein) |
| Cadus 4184 | 214–688 |
| Cadus 4185 | 214–473 |
| Cadus 4186 | 1–473 |
| Cadus 4747 | insertion of Lys-Leu between aa 85 & 86 |
| Cadus 4553 | insertion of Ser-Leu between aa 103 & 104 |
| Cadus 4554 | Δ253–305 |
| Cadus 4555 | Δ572–669 |
| Cadus 4556 | Δ588–669 |

Cadus 4183 was constructed by digesting pOF22[GAL4-STE12 1-688] (Cadus 3918) with EcoRI. The 2.8 kb fragment containing the entire STE12 open reading frame was gel purified and subcloned into the EcoRI site of Cadus 4129. Cadus 4184 was constructed by digesting pYZ11 [GAL4-STE12 214-688] (Cadus 3916) with EcoRI. The 2.2 kb EcoRI fragment encoding amino acids 214-688 of Ste12p was gel purified and subcloned into the EcoRI site of Cadus 4129. Cadus 4185 was constructed by digesting pXB1 [GAL4-STE12 214-473] (Cadus 3972) with EcoRI and BamHI. The 780 bp fragment encoding amino acids 214-473 of Ste12p was gel purified and ligated to Cadus 4129 that had been digested with EcoRI and BamHI. Cadus 4186 was constructed by digesting pOG4[GAL4-STE12 1-473] (Cadus 3919) with EcoRI and BamHI. The 1.42 kb fragment encoding amino acids 1-473 of Ste12p was gel purified and ligated to Cadus 4129 that had been digested with EcoRI and BamHI. Primers 5° CCGGAATTCATGAAAGTCCAAATAACC 3' and (SEQ ID NO:10)

5' GCCTGCAGAATTATATTATATCAGGTTG 3' (SEQ ID NO:11)

were used to amplify the insertion and deletion mutants of Ste12p. The amplified products bear EcoRI sites on their 5' ends and PstI sites on their 3' ends. They were digested with EcoRI and PstI, gel purified, and ligated to Cadus 4129 that had been digested with EcoRI and PstI. Cadus 4747 contains the amplified product of plasmid lk85 (Cadus 3913), Cadus 4553 the product of plasmid 1k103 (Cadus 3910), Cadus 4554 the product of D11[D253-305] (Cadus 3911, Cadus 4555 the product of D7[D512-699] (Cadus 3912), and Cadus 4556 the product of D22[D588-66].

Example 7

Detection of Ste2p Activation using the PHO4/STE12 chimerae

This example demonstrates the use of the PHO4/STE12 chimerae (described in Example 5) to induce expression of the PHO5 gene when the pheromone response pathway is activated.

Strain Construction

The endogenous PHO4 gene was disrupted in CY 1638 (MATa far1*1442 tbt1-1 FUS1-HIS3 trp1ura3 leu2 his3 suc2) with the gene encoding Kanamycin resistance, KanMX2, (Yeast 10:1793–1808). Primers

5' GAGCAAAGGAGACAGAACAAGAGTAGCA-GAAAGTCCAGCTGAAGCTTCGTACGC

3' and (SEQ ID NO:12)

5'

CACGTGCTCACGTTCTGCTGTAGGT-GACGGATGTAGCATAGGCCACTAGTGGATCTG

3' (SEQ ID NO:13)

were used to amplify the KanMX2 gene. The amplification product was flanked by sequences corresponding to the 5' and 3' ends of the PHO4 gene. This DNA was transformed into CY 1638. Transformants were selected on YEPD+ geneticin (200 µg/ml) plates. The disruption of PHO4 in this strain, CY 9788, was verified by assessing acid phosphatase activity in cells grown on phosphate-depleted YEPD medium (100 ml YEPD, 1 ml NH$_4$OH, 1 ml MgSO$_4$ [1 M]; let stand 30 min; filter) (Biscon and Thorner, Genetics. 1982). Acid phosphatase activity was assessed using the overlay assay of Toh-e et al (*J. Bacteriol*, 1973). Cells were patched onto YEPD or phosphate-depleted YEPD plates and allowed to grow overnight. For each plate, a mixture of 2 ml of molten 1% agarose in 50 mM NaAc pH 4.0, 700 µl H$_2$O, and 300 µl α-napthyl acid phosphate (50 mg/ml) was prepared and applied to the plate. Then 1 ml of D-dianisidine fast blue salt B (50 mg/ml in 50 mM NaAc pH 4.0) was poured onto the plate. The degree of color development is a measure of acid phosphatase activity produced by the patch of cells. As expected CY 9788 had much lower acid phosphatase activity than CY 1638.

The small amount of acid phosphatase activity observed in CY 9788 is likely that of Pho3p. The PHO3 gene also encodes a secreted acid phosphatase, but its expression is not regulated by Pho4p. Instead, its expression is induced under high-phosphate conditions and is further increased by thiamine starvation (Reviewed by Vogel and Hinnen. 1990. Mol. Microbiol). Since this gene is not essential and its presence would require that all assays be done under conditions of phosphate starvation, it was disrupted. Primers 5' CATGAAGCTTCTCCTACTACCAAGACTG 3' and (SEQ ID NO:14)

5' GATCGAATTCGGTAATTTGGAATGGC 3' (SEQ ID NO:15)

were used to amplify sequences at the 5' end of the PHO3 gene. The amplification product which bears a HindIII site at its 5' end and an EcoRI site at its 3' end was digested with HindIII and EcoRI and gel purified. Primers 5' GATCGAATTCCTGTTCCACCGGCC 3' and (SEQ ID NO:16)

5' GATCTCTAGAGAGGCGATTGCTGTAATGC 3' (SEQ ID NO:17)

were used to amplify sequences in the 3' untranslated region of the PHO3 gene. The amplification product which bears an EcoRI site ate its 5' end and an XbaI site at its 3' end was digested with EcoRI and XbaI and gel purified. The URA3 marked integrating vector pRS406 (Cadus 1011) (Sikorski and Hieter. 1989. Genetics) was digested with HindIII and XbaI, gel purified and used in a three-piece ligation with the two PCR products. The resulting two-step disruption (Boeke et al. 1988) plasmid, Cadus 4602, was digested with Hpa1 and used to transform Cy 9788 to uracil prototrophy. Subsequent selection for Ura derivitaves of this transformant using S-FOA yielded CY 11643, bearing the deletion of the Pho3 gene. The disruption of PHO3 in CY 11643 was verified by measuring acid phosphatase activity on YEPD plates and on phosphate-depleted YEPD plates as described above. As expected CY 11643 had extremely low acid phosphatase activity on both plate. Activity of its parent, CY 9788, was very high on the YEPD plate (due to the presence of Pho3p) but very low on the phosphate-depleted SD plate (due to the lack of Pho4p). Finally, activity of the original strain, CY 1638, was very high on both plates indicating that both Pho4 and Pho3 had been disrupted.

The nine PHO4/STE12 chimerae plasmids (described in Example 5) and Cadus 4129, which encodes only the Pho4 DNA binding domain, were then transformed into CY 11643.

Detection of Ste2p Activation by Measuring Pho5p Activity in strains containing the PHO41STE12 Chimerae Cells were grown overnight in SD TRP- media. The overnight cultures were diluted to OD$_{600}$ 0.2 and allowed to grow a few hours (to OD$_{600}$ 0.4). The cultures were split in half (2.5 ml each) and α-factor (25 µg) was added to one aliquot. After 2.5 hours at 30° C., the cells were collected by centrifugation, washed 3 times with H$_2$O, once with 50 mM NaAc pH 4.0, and resuspended in 250 µl 50 mM NaAc pH 4.0. Acid phosphatase activity was assessed essentially as described by Torriani (*Biochim. Biophys.* ACTA, 1960). 100 µl cells were added to 400 µl p-nitrophenyl phosphate (1 mg/ml in 50 mM NaAc pH 4.0). After 15 min at room temperature, 720 µl saturated NaCO$_3$ was added to stop the reaction. The cells were removed by centrifugation and the optical density at 420 nm was determined. Activities were normalized to the optical density at 600 nm of 100 µl cells in 900 µl H$_2$O. The results of two independent experiments are summarized in the following Table:

| Plasmid | −α-factor | +α-factor |
|---|---|---|
| Cadus 4129 | +/− | +/− |
| Cadus 4183 | +/− | ++ |
| Cadus 4184 | +++ | ++++ |
| Cadus 4185 | +++ | ++++ |
| Cadus 4186 | + | ++ |
| Cadus 4747 | +/− | + |
| Cadus 4553 | + | +++ |
| Cadus 4554 | + | ++ |
| Cadus 4555 | + | +++ |
| Cadus 4556 | +/− | ++ |

Cells expressing only the Pho4p DNA binding domain (CY11643+Cadus 4129) (and no Ste12 component) had extremely low acid phosphatase activity that was not increased by exposure to α-factor. In contrast, pheromone-inducible acid phosphatase activity was observed in all of the strains expressing Pho4/Ste12 chimerae. Two of the chimerae, Pho4/Ste12(214-473) (Cadus 4184) and Pho4/Ste12(1-473) (Cadus 4185), also had high levels of constitutive Pho5p activity, but only a 2–4 fold induction ratio. Several chimerae had similar induction ratios. Others had very low constitutive activity and similar induction ratios of 5–10 fold. These data demonstrate that Pho4/Ste12 chimeric transcription factors can be used to render the PHO5 gene pheromone-inducible. By extension, this readout can be used to detect activation of any G-protein coupled receptor expressed in *S. cerevisiae*, as well as activation of any pheromone respoonse pathway component downstream of the receptor. Such activation may be due to modulation by a compound or by protein-protein interaction (e.g., by interaction with a cloned heterologous gene product).

Example 8

Functional Expression of a Mammalian G Protein-Coupled Receptor and Ligand in an Autocrine Yeast Strain.

In this example, the construction of a yeast cell expressing a G protein-coupled receptor which is suitable for use in the instant assays is described. This example details the following: (1) expression of human C5a receptor in yeast; (2) expression of the native ligand of this receptor, human C5a, in yeast; and (3) activation of the endogenous yeast pheromone pathway upon stimulation of the C5a receptor by C5a when both of these molecules are expressed within the same strain of autocrine yeast. Following the experimental data the utility of autocrine strains of yeast that functionally express the human C5a receptor is outlined.

Human C5a is a 74 amino acid polypeptide that derives from the fifth component of complement during activation of the complement cascade; it is the most potent of the complement-derived anaphylatoxins. C5a is a powerful activator of neutrophils and macrophage functions including production of cytotoxic super oxide radicals and induction of chemotaxis and adhesiveness. In addition C5a stimulates smooth muscle contraction, induces degranulation of mast cells, induces serotonin release from platelets and increases vascular permeability. The C5a anaphylatoxin can also amplify the inflammatory response by stimulating the production of cytokines. As C5a is a highly potent inflammatory agent, it is a primary target for the development of antagonists to be used for intervention in a variety of inflammatory processes.

The C5a receptor is present on neutrophils, mast cells, macrophages and smooth muscle cells and couples through G proteins to transmit signals initiated through the binding of C5a.

Expression of the C5a Receptor

The plasmid pCDM8-C5aRc, bearing cDNA sequence encoding the human C5a receptor, was obtained from N. Gerard and C. Gerard (Harvard Medical School, Boston, Mass.) (Gerard and Gerard 1991). Sequence encoding C5a was derived from this plasmid by PCR using VENT polymerase (New England Biolabs Inc., Beverly Mass.), and the following primers:

1-GGTGGGAGGGTGCTCTCTAGAAGGAAGTGT-TCACC (SEQ ID NO:18)
2-GCCCAGGAGACCAGACCATGGACTCCTTCAA-TTATACCACC (SEQ ID NO:19)

Primer #1 contains a single base-pair mismatch (underlined) to C5a receptor cDNA. It introduces an XbaI site (in bold) 201 bp downstream from the TAG termination codon of the C5a receptor coding sequence. Primer #2 contains two mismatched bases and serves to create an NcoI site (in bold) surrounding the ATG initiator codon (double underlined). The second amino acid is changed from an aspartic acid to an asparagine residue. This is the only change in primary amino acid sequence from the wild type human C5a receptor.

The PCR product was restricted with NcoI and XbaI (sites in bold) and cloned into CADUS 1002 (YEp51Nco), a Gal10 promoter expression vector. The sequence of the entire insert was determined by dideoxy sequencing using multiple primers. The sequence between the NcoI and XbaI sites was found to be identical to the human C5a receptor sequence that was deposited in GenBank (accession #JO5327) with the exception of those changes encoded by the PCR primers. The C5a receptor-encoding insert was transferred to CADUS 1289 (pLPXt), a PGK promoter expression vector, using the NcoI and XbaI sites, to generate the C5a receptor yeast expression clone, CADUS 1303.

A version of the C5a receptor which contains a yeast invertase signal sequence and a myc epitope tag at its amino terminus was expressed in Cadus 1270-transferred yeast under control of a GAL10 promoter. Plasmids encoding an untagged version of the C5a receptor and a myc-tagged derivative of FUS1 served as controls. The expression of the tagged receptor in yeast was confirmed by Western blot using the anti-myc monoclonal antibody 9E10. In the lane containing the extract from the Cadus 1270-transformant, the protein that is reactive with the anti-myc monoclonal antibody 9E 10 was approximately 40 kD in size, as expected. Note that this receptor construct is not identical to the one used in the autocrine activation experiments. That receptor is not tagged, does not contain a signal sequence and is driven by the PGK promoter.

Expression of the Ligand, C5a

A synthetic construct of the sequence encoding C5a was obtained from C. Gerard (Harvard Medical School, Boston, Mass.). This synthetic gene had been designed as a FLAG-tagged molecule for the secretion from *E. coli* (Gerard and Gerard (1990) *Biochemistry* 29:9274–9281). The C5a coding region, still containing *E. coli* codon bias, was amplified using VENT polymerase (New England Biolabs Inc., Beverly Mass.) through 30 cycles using the following primers:

C5a5'= CCCCTTAAGCGTGAGGCAGAAGC-TACTCTGCAAAAGAAGATC (SEQ ID NO:20)
C5a3'=GAAGATCTT<u>CAGCGGCCGAGTTGCATGTC</u> (SEQ ID NO:21)

A PCR product of 257 bp was gel isolated, restricted with AflII and BglII, and cloned into CADUS 1215 (an expression vector designed to express peptide sequences in the context of Mfα) to yield CADUS 1297. The regions of homology to the synthetic C5a gene are underlined. The 5' primer also contains pre-pro α-factor sequence. Upon translation and processing of the pre-pro α-factor sequence, authentic human C5a should be secreted by yeast containing CADUS 1297. The insert sequence in CADUS 1297 was sequenced in both orientations by the dideoxy method and found to be identical to that predicted by the PCR primers and the published sequence of the synthetic C5a gene (Franke et al. (1988) *Methods in Enzymology* 162:653–668).

Two sets of experiments, aside from the autocrine activation of yeast detailed below, demonstrated that CADUS 1297 can be used to express C5a in yeast. 1). C5a was immunologically detected in both culture supernatant and lysed cells using a commercially available enzyme-linked immunosorbent assay (ELISA)(Table 1). This assay indicated the concentration of C5a in the culture supernatant to be approximately 50 to 100 nM. In comparison, in data derived from mammalian cells, the binding constant of C5a to its receptor is 1 nM (Boulay et al.(1991) Biochemistry 30:2993–2999.

2). C5a expressed in yeast was shown to compete for binding with commercially obtained (Amersham Corporation, Arlington Heights, IL), radiolabeled C5a on induced HL60 cells.

Activation of the Pheromone Response Pathway in Autocrine Yeast Expressing the Human C5a Receptor and Human C5a Activation of the yeast pheromone response pathway through the interaction of C5a with the C5a receptor was demonstrated using a growth read-out. The strain used for this analysis, CY455 (MATα tbt1-1 ura3 leu2 trp1 his3 fus1-HIS3 can1 ste14::TRP1 ste3* 1156) contains the following significant modifications. A pheromone inducible HIS3 gene, fus1-HIS3, is integrated at the Fus1 locus. A hybrid gene containing sequence encoding the first 41 amino acids of GPA1 (the yeast Gα subunit) fused to sequence encoding human Gαi2a (minus codons for the N-terminal 33 amino acids) replaces GPA1 at its normal chromosomal location. The yeast STE14 gene is disrupted to lower the basal level of signaling through the pheromone response pathway. The yeast a-factor receptor gene, STE3, is deleted. The last two modifications are probably not essential, but appear to improve the signal-to-noise ratio.

CY455 (MATα tbt1-1 ura3 leu2 trp1 his3 fus1-HIS3 can1 ste14::TRP1 ste3 * 1156) was transformed with the following plasmids:

Cadus 1289+Cadus 1215=Receptor⁻Ligand⁻=(R−L−)
Cadus 1303+Cadus 1215=Receptor⁺Ligand⁻=R+L−
Cadus 1289+Cadus 1297=Receptor Ligand⁺=(R−L+)
Cadus 1303+Cadus 1297=Receptor⁺Ligand⁺=(R+L+)
Receptor refers to the human C5a receptor.
Ligand refers to human C5a.

Three colonies were picked from each transformation and grown overnight in media lacking leucine and uracil, at pH 6.8 with 25 mM PIPES (LEU URA pH6.8 with 25 mM PIPES). This media was made by adding 0.45 ml of sterile 1 M KOH and 2.5 ml of sterile 1M PIPES pH 6.8 to 100 ml of standard SD LEU- URA- media. After overnight growth the pH of this media is usually acidified to approximately pH 5.5. Overnight cultures were washed once with 25 mM PIPES pH 6.8 and resuspended in an equal volume of media lacking leucine, uracil and histidine (LEU URA HIS pH 6.8 with 25 mM PIPES). The optical density at 600 nm of a $\frac{1}{20}$ dilution of these cultures was determined and the cultures were diluted into 25 mM PIPES pH 6.8 to a final $OD_{600}$ of 0.2. A volume (5 ul) of this dilution equivalent to 10,000 cells was spotted onto selective (HIS+TRP-pH6.8) plates. Only those strains expressing both C5a and its receptor (R+L+) show growth on the selective plates which lack histidine. All test strains are capable of growth on plates containing histidine. The R+L+strain will grow on plates containing up to 5 mM aminotriazole, the highest concentration tested.

For verification of pheromone pathway activation and quantification of the stimulation, the activity of the fus1 promoter was determined colorometrically using a fus1-lacZ fusion in a similar set of strains. CY878 (MATα tbt1-1 fus1-HIS3 caN1 ste14::trp1::LYS2 ste3* 1156 gpal(41)-Gαi2) was used as the starting strain for these experiments. This strain is a trp1 derivative of CY455. The transformants for this experiment contained CADUS 1584 (pRS424-fus1-lacZ) in addition to the receptor and ligand plasmids. Four strains were grown overnight in SD LEU URA TRP pH6.8 with 50 mM PIPES to an $OD_{600}$ of less than 0.8. Assay of β-galactosidase activity can be done useing methods known in the art (Guarente 1983). These experiments show that the expression of the C5a receptor and ligand (R+L+) cells results in autocrine stimulation and β-galactosidase activity.

Projected Uses of the Autocrine C5a Strains:

A primary use of the autocrine C5a strains will be in the discovery of C5a antagonists. Inhibitors of the biological function of C5a would be expected to protect against tissue damage resulting from inflammation in a wide variety of inflammatory disease processes including but not limited to: respiratory distress syndrome (Duchateau et al. (1984) Am Rev Respir Dis 130:1058); (Hammerschmidt et al. (1980) Lancet 1:947), septic lung injury (Olson et al. 1985) Ann Surg 202:771), arthritis (Banerjee et al. (1989) J. Immuinol 142:2237), ischemic and post-ischemic myocardial injury (Weisman (1990) Science 146:249); (Crawford et al. (1988) Circulation 78:1449) and burn injury (Gelfand et al. (1982) J. Clin Invest 70:1170).

The autocrine C5a system as described can be used to isolate C5a antagonists as follows:

1. High throughput screens to identify antagonists of C5a.

A straightforward approach involves screening compounds to identify those which inhibit growth of the R+L+ strain described above in selective media but which do not inhibit the growth of the same strain or of a R+L− strain in non-selective media. The counterscreen is necessary to eliminate from consideration those compounds which are generally toxic to yeast. Initial experiments of this type have led to the identification of compounds with potential therapeutic utility.

2. Identification of antagonists using negative selection.

Replacement of the fus1-HIS3 read-out with one of several negative selection schemes (fus1-URA3/FOA, fus1-GAL1/galactose or deoxygalactose, Far1 sst2 or other mutations that render yeast supersensitive for growth arrest) would generate a test system in which the presence of an antagonist would result in the growth of the assay strain. Such an approach would be applicable to high-throughput screening of compounds as well as to the selection of antagonists from random peptide libraries expressed in autocrine yeast. Optimization of screens of this type would involve screening the R+L+ strain at a concentration of aminotriazole which ablates growth of the R+L− strain (for example, 0.6 to 0.8 mM) and counterscreening the R+L− strain at a concentration of aminotriazole which gives an identical growth rate (for example, 0.14 mM). In addition, the system could employ one of several colorometric, fluorescent or chemiluminescent readouts. Some of the genes which can be fused to the fus1 promoter for these alternate read-outs include lacZ (colorometric and fluorescent substrates), glucuronidase 20 (colorometric and fluorescent substrates), phosphatases (e.g. PHO3, PHO5, alkaline phosphatase; colorometric and chemiuminescent substrates), green protein (endogenous fluorescence), horse radish peroxidase (colorometric), luciferase (chemiluminescence).

The autocrine C5a strains have further utility as follows:

3. In the identification of novel C5a agonists from random peptide libraries expressed in autocrine yeast.

Novel peptide agonists would contribute to structure/function analyses used to guide the rational design of C5a antagonists.

4. In the identification of receptor mutants.

Constitutively active, that is, ligand independent, receptors may be selected from highly mutagenized populations by growth on selective media. These constitutively active receptors may have utility in permitting the mapping of the sites of interaction between the receptor and the G-protein. Identification of those sites may be important to the rational design of drugs to block that interaction. In addition, receptors could be selected for an ability to be stimulated by some agonists but not others or to be resistant to antagonist. These variant receptors would aid in mapping sites of interaction between receptor and agonist or antagonist and would therefore contribute to rational drug design efforts.

5. In the identification of molecules that interact with Gαi2.

Compounds or peptides which directly inhibit GDP exchange from Gαi2 would have the same effect as C5a antagonists in these assays. Additional information would distinguish inhibitors of GDP exchange from C5a antagonists. This information could be obtained through assays that determine the following:

1. inhibition by test compounds of Gαi2 activation from other receptors,
2. failure of test compounds to compete with radiolabeled C5a for binding to the C5a receptor,
3. failure of test compounds to inhibit the activation of other Gα subunits by C5a, and
4. inhibition by test compounds of signalling from constitutively active versions of C5a, or other, receptors.

Example 9

Construction of Hybrid Gα Genes Construction of two sets of chimeric yeast/mammalian Gα genes, GPA$_{41}$-Gα and GPA1$_{Bam}$-Gα.

The Gα subunit of heterotrimeric G proteins must interact with both the βγ complex and the receptor. Since the domains of Gα required for each of these interactions have not been completely defined and since our final goal requires Gα proteins that communicate with a mammalian receptor on one hand and the yeast βγ subunits on the other, human-yeast chimeric Gα proteins with an optimized ability to perform both functions were derived. From the studies reported here it was determined that inclusion of only a small portion of the amino terminus of yeast Gα is required to couple a mammalian Gα protein to the yeast βγ subunits. It was anticipated that a further benefit to using these limited chimeras was the preservation of the entire mammalian domain of the Gα protein believed to be involved in receptor contact and interaction. Thus the likelihood that these chimeras would retain their ability to interact functionally with a mammalian receptor expressed in the same yeast cell was expected to be quite high.

Plasmid constructions pRS416-GPA1 (Cadus 1069). An XbaI - SacI fragment encoding the entire GPA1 promotor region, coding region and approximately 250 nucleotides of 3' untranslated region was excised from 10 YCplac111-GPA1 (from S. Reed, Scripps Institute) and cloned into YEp vector pRS416 (Sikorski and Hieter, Genetics 122:19 (1989)) cut with XbaI and SacI.

Site-directed mutagenesis of GPA1 (Cadus 1075, 1121 and 1122). A 1.9 kb EcoRI fragment containing the entire GPA1 coding region and 200 nucleotides from the 5' untranslated region was cloned into EcoRI cut, phosphatase-treated pALTER-1 (Promega) and transformed by electroporation (Biorad Gene Pulser) into DH5αF' bacteria to yield Cadus 1075. Recombinant phagemids were rescued with M13KO7 helper phage and single stranded recombinant DNA was extracted and purified according to the manufacturer's specifications. A new NcoI site was introduced at the initiator methionine of GPA1 by oligonucleotide directed mutagenesis using the synthetic oligonucleotide:

5' GATATATTAAGGTAGGAAACCATGGGGT-GTACAGTGAG 3'. (SEQ ID NO:22)

Positive clones were selected in ampicillin and several independent clones were sequenced in both directions across the new NcoI site at +1. Two clones containing the correct sequences were retained as Cadus 1121 and 1122.

Construction of a GPA1-based expression vector (Cadus 1127). The vector used for expression of full length and hybrid mammalian Gα proteins in yeast, Cadus 1127, was constructed in the following manner. A 350 nucleotide fragment spanning the 3' untranslated region of GPA1 was amplified with Taq polymerase (AmpliTaq; Perkin Elmer) using the oligonucleotide primers A (5' CGAGGCTC-GAGGGAACGTATAATTAAAGTAGTG 3') (SEQ ID NO:23) and B (5' GCGCGGTACCAAGCTTCAATTC-GAGATAATACCC 3'). (SEQ ID NO:24) The 350 nucleotide product was purified by gel electrophoresis using GeneClean II (Bio101) and was cloned directly into the pCRII vector by single nucleotide overlap TA cloning (InVitrogen). Recombinant clones were characterized by restriction enzyme mapping and by dideoxynucleotide sequencing. Recombinant clones contained a novel XhoI site 5' to the authentic GPA1 sequence and a novel KpnI site 3' to the authentic GPA1 sequence donated respectively by primer A and primer B.

The NotI and SacI sites in the polylinker of Cadus 1013 (pRS414) were removed by restriction with these enzymes followed by filling in with the Klenow fragment of DNA polymerase I and blunt end ligation to yield Cadus 1092. The 1.4 kb PstI - EcoRI 5' fragment of GPA1 from YCplac111-GPA1 containing the GPA1 promoter and 5' untranslated region of GPA1 was purified by gel electrophoresis using GeneClean (Bio1O1) and cloned into PstI - EcoRI restricted Cadus 1013 to yield Cadus 1087. The PCR amplified XhoI - KpnI fragment encoding the 3' untranslated region of GPA1 was excised from Cadus 1089 and cloned into XhoI - KpnI restricted Cadus 1087 to yield Cadus 1092. The Not1 and Sac1 sites in the polylinker of Cadus 1092 were removed by restriction with these enzymes, filling in with the Klenow fragment of DNA polymerase I, and blunt end ligation to yield Cadus 1110. The region of Cadus 1122 encoding the region of GPA1 from the EcoRI site at −200 to +120 was amplified with Vent DNA polymerase (New England Biolabs, Beverly, Mass.) with the primers 5' CCCGAATCCACCAATTTCTTTACG 3' (SEQ ID NO:25)and

5' GCGGCGTCGACGCGGCCGCGTAACAGT 3' (SEQ ID NO:26).

The amplified product, bearing an EcoRI site at its 5' end and novel SacI, NotI and SalI sites at its 3' end was restricted with EcoRI and SalI, gel purified using GeneClean II (BiolO1), and cloned into EcoRI and SalI restricted Cadus 1110 to yield Cadus 1127. The DNA sequence of the vector between the EcoRI site at −200 and the KpnI site at the 3' end of the 3' untranslated region was verified by restriction enzyme mapping and dideoxynucleotide DNA sequence analysis.

PCR amplification of GPA$_{41}$-Gα proteins and cloning into Cadus 1127.

cDNA clones encoding the human G alpha subunits Gαs, Gαi2, Gαi3, and S. cerevisiae GPA1 were amplified with Vent thermostable polymerase (New England Bioloabs, Beverly, Mass.). The primer pairs used in the amplification are as follows:

GαS Primer 1: 5' CTGCTGGAGCTCCGCCTGCTGCT-GCTGGGTGCTGGAG3' (SacI 5') (SEQ ID NO:27)

Primer 2: 5' CTGCTGGTCGACGCGGCCGCGGGGGT-TCCTTCTTAGAAGCAGC3' (SalI 3') (SEQ ID NO:28)

Primer3: 5'GGGCTCGAGCCTTCTTAGAG-CAGCTCGTAC3' (XhoI 3') (SEQ ID NO:29)

Gαi2 Primer 1: 5'CTGCTGGAGCTCAAGTTGCTGCT-GTTGGGTGCTGGGG3' (SacI5') (SEQ ID NO:30)

Primer 2: 5'CTGCTGGTCGACGCGGCCGCGCCCCT-CAGAAGAGGCCGCGGT CC3' (SalI 3') (SEQIDNO:31)

Primer 3: 5'GGGCTCGAGCCTCAGAAGAGGCCG-CAGTC3' (XhoI 3') (SEQ ID NO:32)

Gαi3 Primer 1: 5' CTGCTGGAGCTCAAGCTGCTGC-TACTCGGTGCTGGAG3' (SacI5') (SEQ ID NO:33)

Primer 2: 5'CTGCTGGTCGACGCGGCCGCCACTAA-CATCCATGCTTCTCAAT AAAGTC3' (SalI 3') (SEQ ID NO:34)

Primer 3: 5'GGGCTCGAGCATGCTTCT-CAATAAAGTCCAC3' (XhoI 3') (SEQ ID NO:35)

After amplification, products were purified by gel electrophoresis using GeneClean II (Bio101) and were cleaved with the appropriate restriction enzymes for cloning into Cadus 1127.

The hybrid $GPA_{41}$-$G_\alpha$ subunits were cloned via a SacI site introduced at the desired position near the 5' end of the amplified genes and a SalI or XhoI site introduced in the 3' untranslated region. Ligation mixtures were electroporated into competent bacteria and plasmid DNA was prepared from 50 cultures of ampicillin resistant bacteria.

Construction of Integrating Vectors Encoding $GPA_{41}$-$G_\alpha$ Subunits. The coding region of each $GPA_{41}$-$G_\alpha$ hybrid was cloned into an integrating vector (pRS406=URA3 AmpR) using the BssHII sites flanking the polylinker cloning sites in this plasmid.

Cadus 1011 (pRS406) was restricted with BssHII, treated with shrimp alkaline phosphatase as per the manufacturer's specifications, and the linearized vector was purified by gel electrophoresis. Inserts from each of the $GPA_{41}$-$G_\alpha$ hybrids were excised with BssHII from the parental plasmid, and subcloned into gel purified Cadus 1011.

Construction of $GPA_{BAM}$-$G\alpha$ Constructs. A novel BamHI site was introduced in frame into the GPA1 coding region by PCR amplification using Cadus 1179 (encoding a wildtype GPA1 allele with a novel NcoI site at the initiator methionine) as the template, VENT polymerase, and the following primers: Primer A=5' GCATCCATCAATAATC-CAG 3' (SEQ ID NO:36) and Primer B=5' GAAA-CAATGGA - TCCACTTCTTAC 3'. (SEQ ID NO:37) The 1.1 kb PCR product was gel purified with GeneClean II (Bio101), restricted with NcoI and BamHI and cloned into NcoI-BamHI cut and phosphatased Cadus 1122 to yield Cadus 1605. The sequence of Cadus 1605 was verified by restriction analysis and dideoxy-sequencing of is double-stranded templates. Recombinant $GPA_{Bam}$-$G\alpha$ hybrids of Gαs, Gαi2, and Gα16 were generated. Construction of Cadus 1855 encoding recombinant $GPA_{Bam}$-$G\alpha$ 16 serves as a master example: construction of the other hybrids followed an analogous cloning strategy. The parental plasmid Cadus 1617, encoding native Gα16, was restricted with NcoI and BamHI, treated with shrimp alkaline phosphatase as per the manufacturer's specifications and the linearized vector was purified by gel electrophoresis. Cadus 1605 was restricted with NcoI and BamHI and the 1.1 kb fragment encoding the amino terminal 60% of GPA1 with a novel BamHI site at the 3' end was cloned into the NcoI- and BamHI-restricted Cadus 1617. The resulting plasmid encoding the $GPA_{Bam}$-Gα 16 hybrid was verified by restriction analysis and assayed in tester strains ror an ability to couple to yeast Gβγ and thereby suppress the gpal null phenotype. Two additional $GPA_{Bam}$-Gα hybrids, $GPA_{Bam}$-Gαs and $GPA_{Bam}$-Gαi2, described in this application were prepared in an analogous manner using Cadus1606 as the parental plasmid for the construction of the $GPA_{Bam}$-Gαi2 hybrid and Cadus 1181 as the parental plasmid for the construction of the $GPA_{Bam}$-Gαs hybrid.

Coupling by chimeric Gα proteins. The Gα chimeras described above were tested for the ability to couple a mammalian G protein-coupled receptor to the pheromone response pathway in yeast.

Example 10

Screening for Modulators of G-alpha activity

Screens for modulators of Gα activity may also be performed as shown in the following examples for illustration purposes, which are intended to be non-limiting. Strains CY4874 and CY4877 are isogenic but for the presence of Q205L mutation in the cloned $G\alpha_{i2}$ gene cloned into plasmid 1. Strains CY4901 and CY4904 each have a chromosomally integrated chimeric Gα fusion comprising 41 amino acids of gpal at the N terminus of the human $G\alpha_{i2}$ gene and are isogenic but for the presence of a constitutively activating mutation in the C5a receptor gene of CY4901. Strain CY5058 is a gpal mutant which carries only the yeast Gβγ subunits and no Gα subunit. This strain is a control strain to demonstrate specificity of action on the Gα subunit.

I. Suppression of Activation by Mutation of Gα

The Q205L mutation is a constitutively activated GTPase deficient mutant of the human $G\alpha_{i2}$ gene. Antagonist compounds, chemicals or other substances which act on G $\alpha_{i2}$ can be recognized by their action to reduce the level of activation and thus reduce the signal from the fus1-lacZ reporter gene on the second plasmid (Plasmid 2).

A. GTPase $G\alpha_{i2}$ Mutants test component=$gpa_{41}$-$G\alpha_{i2}$ ($Q_{205}$L)

control component=$gpa_{41}$-$G\alpha_{i2}$

As well as the CY4874 and CY4877 constructs detailed above, similar strains with fus1-His3 or fus2-CAN-1 growth readouts may also be used. The fus1-His3 strains are preferred for screening for agonists and the fus2-CAN1 strains are preferred for antagonist screens.

| Readout | test strain | effect of $G\alpha_{i2}$ antagonist | control strain |
|---|---|---|---|
| fus1-HIS3 | CY4868 | inhibit growth of –HIS +AT (Aminotriazole) | CY4871 |
| fus1-lacZ | CY4874 | reduce β-gal activity | CY4877 |
| fus2-CAN1 | CY4892 | induce growth on canavanine | CY4386 |

In each case an antagonist should cause the test strain to behave more like the control strain.

B. GTPase $G\alpha_S$ Mutants (Gα Specificity)

test component=$G\alpha_s(Q_{227}L)$ control component=$G\alpha_S$

| Readout | test strain | effect of $G\alpha_{i2}$ antagonist | control strain |
|---|---|---|---|
| fus1-HIS3 | CY4880 | none | CY4883 |
| fus1-lacZ | CY4886 | none | CY4889 |
| fus2-CAN1 | CY4895 | none | CY4898 |

In each case a non-specific antagonist would cause the test strain to behave more like the control strain.

Additional media requirements: -TRP for Gα plasmid maintenance in fus1-HIS3 and fus2-CAN1 screens and -TRP -URA for Gα and fus1-lacZ plasmid maintenance in fus1-lacZ screen.

II. Suppression of Activation by Receptors Constitutively Activated C5a Receptors test component=C5aR* ($P_{184}L$, activated C5a Receptor)

control component=C5aR

The C5AR* mutation has a Leucine residue in place of the Proline residue of the wild-type at position 184 of the amino acid sequence.

| Readout | test strain | effect of $G\alpha_{i2}$ antagonist | control strain |
|---|---|---|---|
| fus1-HIS3 | CY4029 | inhibit growth of –HIS +AT (Aminotriazole) | CY2246 |
| fus1-lacZ | CY4901 | reduce β-gal activity | CY4904 |
| fus2-CAN1 | CY4365 | induce growth on canavanine | CY4362 |

In each case an antagonist should cause the test strain to behave more like the control strain.

Additional media requirements: -LEU for receptor plasmid maintenance in fus1-HIS3 and fus2-CAN1 screens and -LEU-URA for receptor and fus1-lacZ plasmid maintenance in fus1-lacZ screen, non-buffered yeast media (pH 5.5).

Example 11

Identification of a surrogate ligand using expression of a random peptide library in yeast expressing an orphan mammalian receptor FPRL-1 (formyl peptide receptor-like 1) is a structural homolog of the formyl peptide receptor (FPR). FPR is a G protein-coupled receptor, expressed on neutrophils and phagocytic cells, that is stimulated by N-formyl peptides of bacterial origin. Specific binding of the natural ligand, f-Met-Leu-Phe, stimulates transduction of a signal to mobilize calcium, resulting in cellular changes including chemotaxis and the release of granule contents. Low stringency hybridization of HL60 cDNA libraries with an FPR cDNA probe permitted the identification of the related receptor, FPRL-1 (Murphy et al. supra; Ye et al. supra). The FPRL-1 cDNA encodes a 351 amino acid protein with 69% sequence homology to FPR (Murphy et al. supra) FPR and FPRL-1 were found to co-localize to human chromosome 19 and to have a tissue expression pattern identical to that of FPR, i.e., expression is restricted to cells of myeloid origin (Murphy et al. supra). Ye et al. (supra) demonstrated weak binding of f-Met-Leu-Phe (uM concentrations) to fibroblasts transfected with FPRL-1 cDNA. In contrast, Murphy et al. (supra) could not detect binding of N-formyl peptides to Xenopus oocytes transfected with FPRL-1 cDNA. FPRL-I appears to be an orphan receptor whose specific ligand differs from the formyl peptide ligands to which FPR responds.

In this example experiments detailing the following will be described: (1) establishment of a strain of yeast designed to express the human orphan G protein-coupled receptor FPRL-1; (2) expression of a random peptide library in the aforementioned strain of yeast; and (3) activation of the endogenous yeast pheromone pathway upon stimulation of the FPRL- 1 receptor by a peptide encoded by a random library expressed within the same strain of yeast.

Preparation of FPRL-1 Yeast Expression Vector

A plasmid, pFPRL1 -L3 1, containing a 2.6 kb EcoRI-Xho1 fragment encoding the FPRL-1 cDNA in the BluescriptIISK+vector was obtained from Philip Murphy (NIH). The sequence encoding FPRL1 was amplified by the polymerase chain reaction using VENT polymerase (New England Biolabs, Inc., Beverly, Mass.) through 20 cycles and the following oligonucleotide primers:

1 5'GGCGCCCGGTCTCCCATGGAAACCAACT-TCTCCACT (SEQ ID NO:38)

2 5'GGCGCCCGGTCTCCGATCCCATTGCCTG-TAACTCAGTCTC (SEQ ID NO:39)

The PCR product was purified, restricted with BsaI and cloned into Cadus 1651 (p1PBX-1), a PGK promoter-driven expression vector, using NcoI and BamHI sites, to yield CADUS 2311. The sequence of the entire insert was determined and found to be identical to the FPRL-1 sequence deposited in GenBank (accession number M84562).

Preparation of Random Oligonucleotides

Library-Recycling Protocol to Identify a Surrogate Ligand

The yeast strain CY1141 (MATalpha far1*1441 tbt1-1 fus1-HIS3 can 1 ste14::trp1:;LYS2 ste3*1156 gpa1(41)-Galphai2 lys2 ura3 leu2 trp1 his3) was used in the experiments that follow. CY1141 contains a pheromone inducible HIS3 gene, fus1-HIS3 integrated at the FUS1 locus and a hybrid gene encoding the first 41 amino acids of GPA1 (yeast G alpha) fused to sequence encoding human G alphai2 (lacking codons encoding the N-terminal 33 amino acids) replacing GPA1 at its chromosomal locus. The yeast STE14 gene is disrupted to lower the basal level of signaling through the pheromone response pathway. The yeast a-factor receptor gene, STE3, is deleted. CY1141 was transformed with Cadus 2311 to yield CY6571, a strain expressing the human orphan receptor, FPRL-1.

CY6571 exhibited LIRMA (ligand independent receptor mediated activation), that is, activation of the yeast pheromone pathway in the absence of ligand. It was determined that the yeast growth on selective media that resulted from LIRMA was eliminated by the additional of 2.5 millimolar concentrations of 3-aminotriazole (AT). AT is an inhibitor of the HIS3 gene product that serves to reduce background growth. Therefore, selection protocols aimed at the identification of surrogate ligands for the FPRL-1 receptor were carried out at this concentration of AT.

CY6571 was inoculated to 10 mls of standard synthetic media (SD) lacking leucine (-Leu) and incubated overnight at 30° C. The 10 ml overnight culture was used to inoculate 50 mls of YEPD; this culture was incubated at 30° C. for 4.5–5 hours at which time the cells were harvested and prepared for transformation with DNA encoding a random peptide library [alpha-NNK (6.24.94)] encoding tridecapeptides of 3o random sequence, by electroporation. Post electroporation (in 0.2 cm cuvettes, 0.25 μF, 200Ω, 1.5 kV) the cells were immediately diluted in 1 ml ice-cold 1M sorbitol and 100 μL aliquots were placed onto 10 synthetic media plates (pH6.8) lacking leucine and uracil (-Leu-Ura). The plates were incubated at 30° C for 2–4 days at which time two replicas of each original transformation plate were made to synthetic media (pH6.8) lacking leucine, uracil and histidine and supplemented with 2.5 mM AT(-Leu-Ura-His+2.5 mM AT). The replicas were incubated at 30° C. for 3–5 days. Post incubation the colonies present on the replica sets of two were scraped from the plates into a total of 10 mls of $H_2O$ (5 mls each plate). The $OD_{600}$ of each cell suspension was determined and crude plasmid isolations were done on 8–16 OD units of cells for each pool. A total of eight pools resulted, due to lower numbers of yeast colonies present in four sets of plates. The pellets obtained from these crude plasmid isolations (the so called "smash and grab" technique, Methods in Yeast Genetics - A Laboratory Manual, 1990, M. D. Rose, F. Winston and P. Heiler. Cold Spring Harbor Laboratory Press, Cold Spring Harbor, N.Y.), were resuspended in 40 μL of 10 mM Tris, 1 mM EDTA, pH8.0 and 1 μL was used to transform E. coli by electroporation (0.1 cm cuvettes, 0.25 μF, 200Ω, 1.8 kV).

Post electroporation the cells were immediately diluted into 1 ml 2XYT media and incubated, with shaking, at 37° C for 30 minutes after which time the cells were used to inoculate 50 mls of 2xYT supplemented with 100 ug/ml ampicillin. The 10 resulting cultures were incubated at 37° C overnight. Plasmid DNA was isolated from each of these bacteria cultures using Qiagen columns (Qiagen, Inc., Chatsworth, Calif.)). Each plasmid DNA pellet was resuspended in 50 μL Tris 10 mM, EDTA 1 mM, pH 8.0.

Strain CY6571 was transformed with 1 μL of each plasmid pool by 15 electroporation. Post electroporation the cells were diluted into 400 μL 1M sorbitol.

From each electroporated cell suspension, 1 μL and 400 μL of cells were plated on -Leu-Ura synthetic media, pH6.8 to yield "low density" and "high density" platings. The plates were incubated at 30° C. for 3 days, at which time replicas of both the low and high density plates were made to -Leu-Ura-His+2.5 mM AT. For those cases where enrichment for a plasmid capable of conferring a His+phenotype had occurred, this would be reflected by an amplified number of His+colonies on both the low and high density plates visible at days 2–3, although the amplification would be most obvious on the plates that had received a high density of cells. In the FPRL-1 experiment ⅛ pools showed amplification of His+colonies. The cells were scraped from this plate into 5 mls of $H_2O$, the $OD_{600}$ of the cell suspension was determined and a crude plasmid isolation was done on 15 OD units of yeast cells. The pellet obtained was resuspended in 40 μL 10 mM Tris, 1 mM EDTA, pH8.0 and 1 μL was used to transform E. coli. Plasmid DNA was isolated by miniprep from 3 ml 2XYT cultures of single bacterial colonies resulting from this transformation. 10 DNA pellets (A1 through A10) deriving from individual bacterial colonies were resuspended in 20 μL 10 mM Tris 1 mM EDTA, pH8.0 and used to transform CY6571 (containing the FPRL-1 expression vector) and CY6263 (CY1141 containing a control expression vector lacking any receptor sequence) by electroporation. Cadus 1625, a control vector lacking sequences encoding a peptide, was included and used to transform both the receptor+ and receptor– strains of yeast. Transformants were first selected on -Leu-Ura, pH6.8 then three yeast transformants of each type (from 11 CY6571 transformations and 11 CY6263 transformations) were patched to -Leu-Ura, pH6.8 to expand the colonies. Once expanded, streaks of the transformants were made on -Leu-Ura-His+2.5 mM AT to test for growth in the absence of histidine. All plasmids except the one denoted A2 conferred a growth advantage on media lacking histidine to yeast bearing the FPRL-1-encoding plasmid but not to yeast lacking the receptor plasmid. The peptide sequence found to be encoded by plasmids A1 and A3–A10 is: SerLeuLeuTrpLeuThrCysArgProTrpGluAlaMet, (SEQ ID NO:40) and is encoded by the nucleotide sequence 5'- TCT CTG CTT TGG CTG ACT TGT CGG CCT TGG GAG GCG ATG-3'. (SEQ ID NO:41)

Activation of the Pheromone Response Pathway in Yeast Expressing the FPRL-1 Receptor and Peptide Agonist.

For verificatiin of pheromone pathway activation and quantification of the stimulation, the activity of the fus1 promoter was determined colorimetrically using a fus1-lacZ fusion in a parallel set of test strains. CY1141, described above, was used as the recipient strain for these experiments. Transformants contained CADUS 1584 (pRS424-fus1-lacZ) in addition to receptor ($R^{+/-}$) and ligand ($L^{+/-}$) plasmids. Four strains (bearing the identical plasmids) were grown overnight in minimal media lacking leucine, uracil, and tryptophan, pH8.6. The overnight cultures were used to inoculate -Leu -Ura -Trp pH6.8 media and these new cultures were grown for approximately 4.5–5 hours to an $OD_{600}$ of less than 0.4. Assay of β-galactosidase activity (Guarente 1983) in cells from these cultures yielded the following results:

| | | |
|---|---|---|
| CY1141/CADUS 2311/peptide A1/CADUS 1584 | $R^+L^+$ | 28 units |
| CY1141/CADUS 2311/CADUS 1625/CADUS 1584 | $R^+L^-$ | 3 units |
| CY1141/CADUS 1289/peptide A1/CADUS 1584 | $R^-L^+$ | 3.5 units |
| CY1141/CADUS 1289/CADUS 1625/CADUS 1584 | $R^-L^-$ | 3.9 units |

The presence of receptor and peptide-encoding plasmids resulted in an average 8-fold stimulation over background levels of β-galactosidase.

Example 12

Identification of surrogate ligands using expression of a random peptide library in yeast expressing the orphan mammalian receptor, MDR-15.

In a similar manner a plasmid encoding the monocyte derived receptor monocyte-derived receptor 15 (MDR15; Barella et al. (1995) Biochem. J 309:773–9) was used to construct a yeast strain (CY6573) expressing this receptor. This receptor is an alternative spliced form of the Burkitt's lymphoma receptor 1 (BLR1) encoded by a human Burkitt's lymphoma cDNA (Dobner et al. (1992) Eur. J. Immunol. 22, 2795–2799). Strain CY6573 was transformed in a similar manner with the NNK13 library, and, following selection on ten -Leu-Ura ($4.4 \times 10^5$ colonies per plate), replica plated to -Leu-Ura-His+1 mM AT plates. Upon reisolation of plasmid pools and re-transformation into strain CY6573; eight of ten pools showed signicantly enriched colony formation on -Leu-Ura-His+1 mM AT plates. Eight unique plasmids derived from these pools when retransformed into CY6573 conferred growth on -Leu-Ura-His+1 mM AT plates. One of these plasmids failed to confer growth in a yeast strain lacking the MDR15 receptor.

Example 13

Identification of a ligand using expression of a random peptide library in yeast expressing the human thrombin receptor The receptor for thrombin, a G protein-coupled receptor, is present on numerous cell types including platelets, vascular smooth muscle, fibroblasts and on a subset of cells that function in immunity. Thrombin, a serine protease, binds to and cleaves the receptor molecule at residue 41, generating a new receptor N-terminus. The post-cleavage N-terminal residues then act as a "tethered ligand' to activate the receptor molecule (Vu et al. 1994). In platelets, signaling through the thrombin receptor has been shown to result in numerous effects including stimulation of phospholipase C, mobilization of intracellular $Ca^{2+}$ and inhibition of adenylyl cyclase.

In this example experiments that detail the following will be described (1) establishment of a strain of yeast designed to express the human G protein-coupled receptor for thrombin; (2) expression of a random peptide library in the afore-mentioned strain of yeast and (3) activation of the endogenous yeast pheromone pathway upon stimulation of the thrombin receptor by peptides encoded by a random library expressed within the same strain of yeast.

Preparation of a Yeast Expression Vector for a Mammalian Thrombin Receptor

The human thrombin receptor was amplified by PCR from pcDNA3 :Hu-Thr9b-5' (Bristol Myers Squibb) using the following oligonucleotides:

5' GGGCCATGGGGCCGCGGCGGTTG 3' (SEQ ID NO:42)

5° CCCGGATCCTAAGTTAACAGCTTTTTGTATAT 3' (SEQ ID NO:43)

The amplified product was purified by gel electrophoresis, restricted with NcoI and BamHI and ligated to NcoI and BamHI-cut CADUS 1871, a PGK promoter-driven expression vector, to yield CADUS 2260. Cloning into CADUS 1871 introduces a novel stop codon preceded by the triplet GlySerVal after the authentic carboxy terminal codon of the human thrombin receptor (threonine). In addition, an invertase signal sequence is fused to the authentic amino terminus of the receptor.

CY7467 exhibited LIRMA (ligand independent receptor mediated activation), that is, activation of the yeast pheromone pathway in the absence of ligand. It was determined that the yeast growth on selective media that resulted from LIRMA was eliminated by the addition of 2.5 millimolar concentrations of 3-aminotriazole (AT). AT is an inhibitor of the HIS3 gene product that serves to reduce background growth. Therefore, selection protocols aimed at the identification of novel peptide ligands for the human thrombin receptor were carried out at this concentration of AT.

Preparation of Random Oligonucleotide Library

As described above.

Recycling Protocol to Identify a Surrogate Ligand

The yeast strain CY1141 (MATalpha far1*1442 tbt1-1 fus1-HIS3 can1 ste14::trp1::LYS2 ste3* 1156 gpal(41)-Galphai2 lys2 ura3 leu2 trp1 his3) was transformed with CADUS 2260 to yield strain CY7467, expressing the human thrombin receptor. CY7467 was inoculated to 10 mls of standard synthetic media (SD) lacking leucine (-Leu) and incubated overnight at 30 C. The 10 ml overnight culture was used to inoculate 50 mls of YEPD media; this culture was incubated at 30 C for 4.5–5 hours at which time the cells were harvested and prepared for transformation with DNA encoding a random peptide library [alpha-NNK (6.24.94)] by electroporation. Post electroporation (in 0.2 cm cuvettes, 0.25 mF, 200 W, 1.5 kV) the cells were immediately diluted in I ml ice-cold 1 M sorbitol and 100 mL aliquots were plated onto 10 synthetic media plates (pH6.8) lacking leucine and uracil (-Leu-Ura). The plates were incubated at 30 C for 2–4 days at which time two replicas of each original transformation plate were made to synthetic media (pH6.8) lacking leucine, uracil and histidine and supplemented with 2.5 mM AT(-Leu-Ura-His+2.5 mM AT). The replicas were incubated at 30 C for 3–5 days. Post incubation the colonies present on the replica sets of two were scraped from the plates into a total of 10 mls of $H_2O$ (5 mls each plate). The $OD_{600}$ of each cell suspension was determined and crude plasmid isolations were done on 8–16 OD units of cells for each pool. A total of ten pools resulted. The pellets obtained from these crude plasmid isolations were resuspended in 40 mL of 10 mM Tris, 3 0 1 mM EDTA, pH8.0 and 1 ml was used to transform E. coli by electroporation (0.1 cm cuvettes, 0.25 mF, 200 W, 1.8 kV). Post electroporation the cells were immediately diluted into I ml 2XYT media and incubated, with shaking, at 37 C for 30 minutes after which time the cells were used to inoculate 50 mls of 2xYT supplemented with 100 ug/ml ampicillin. The 10 resulting cultures were incubated at 37 C overnight. Plasmid DNA was isolated from each of these bacterial cultures using Qiagen columns (Qiagen, Inc., Chatsworth, Calif.). Each plasmid DNA pellet was resuspended in 50 mL Tris 10 mM, EDTA 1 mM, pH 8.0.

Strain CY7467 was transformed with 1 mL of each plasmid pool by electroporation. Post electroporation the cells were diluted into 400 mL 1M sorbitol. From each electroporated cell suspension, 1 mL and 400 mL of cells were plated on -Leu-Ura synthetic media, pH6.8 to yield "low density" and "high density" platings. The plates were incubated at 30 C for 3 days, at which time replicas of both the low and high density plates were made to -Leu-Ura-His+2.5 mM AT. For those cases where enrichment for a plasmid capable of conferring a His+phenotype had occurred, this would be reflected by an amplified number of His+colonies on both the low and high density plates visible at days 2–3, although the amplification would be most obvious on the plates that had received a high density of cells. In this experiment 3/10 pools showed amplification of His+ colonies. The cells from each of these plates were scraped into 5 mls of $H_2O$, the $OD_{600}$ of the cell suspensions were determined and crude plasmid isolations were done on 8–16 OD units of yeast cells. The pellets obtained were resuspended in 40 mL 10 mM Tris, 1 mM EDTA, pH8.0 and 1 mL was used to transform E. coli. Plasmid DNA was isolated by miniprep from 3 ml 2XYT cultures of single bacterial colonies resulting from these transformations (three bacterial colonies for each DNA pool were processed in this way). DNAs deriving from three individual bacterial colonies per pool were resuspended in 20 mL 10 mM Tris 1 mM EDTA, pH8.0. The three DNAs derived per pool were sequenced and found to encode identical peptides. Thus three differing DNA sequences were derived, one representing each amplified pool. One plasmid representing each of the three original amplified pools was used to transform CY7467 (containing the thrombin receptor expression vector) and CY6263 (CY1141 containing a control expression vector lacking any receptor sequence) by electroporation. CADUS 1625, a control vector lacking sequences encoding a peptide was included and used to transform both the receptor+ and receptor– strains of yeast. CADUS 1651, a control vector lacking sequences encoding a receptor included and used to transform both the ligand+ and ligand– strains of yeast. Transformants were first selected on -Leu-Ura, pH6.8, then two yeast transformants of each type were patched to -Leu-Ura, pH6.8 to expand the colonies. Once expanded, streaks of the transformants were made on -Leu-Ura-His+ 2.5 mM AT to test for growth in the absence of histidine. One of the three plasmids tested conferred a growth advantage on media lacking histidine to yeast bearing the thrombin-encoding plasmid but not to yeast lacking the receptor plasmid. The peptide sequence encoded by this plasmid is: Val-Cys-Pro-Ala-Arg-Tyr-Val-Leu-Pro-Gly-Pro-Val-Leu (SEQ ID NO:45)and was encoded by the nucleotide sequence GTT TGT CCT GCG CGT TAT GTG CTG CCT GGG CCT GTT TTG. (SEQ ID NO:44)

What is claimed is:

1. An assay for identifying a compound that modulates a heterologous receptor expressed by a yeast cell comprising:
   i) providing a yeast cell which expresses a heterologous receptor which is functionally integrated into an endogenous yeast signaling pathway, wherein said yeast cell comprises an endogenous gene operatively linked to a heterologous promoter at the natural location of said endogenous gene in said yeast cell, said promoter being responsive to signals produced by said yeast signaling pathway;
   ii) contacting the yeast cell with a test compound; and
   iii) detecting an alteration in a signal produced by the endogenous yeast gene;

to thereby identify a compound that modulates the heterologous receptor.

2. The assay of claim 1, wherein said signaling pathway is a yeast pheromone response pathway.

3. The assay of claim 1, wherein said step of detecting comprises measuring transcription of said gene.

4. The assay of claim 1, wherein said step of detecting comprises measuring the amount or activity of an endogenous yeast protein encoded by said gene.

5. The assay of claim 1, wherein said test compound is derived from a library of non-peptidic compounds.

6. The assay of claim 1, wherein the detecting step comprises detecting a change in the activity of an endogenous enzyme expressed by said yeast cell in response to a signal produced by the endogenous yeast signaling pathway.

7. The assay of claim 6, wherein said signaling pathway is a yeast pheromone response pathway.

8. The assay of claim 6, wherein the step of detecting comprises measuring the enzymatic activity of the enzyme.

9. The assay of claim 6, wherein said step of detecting comprises measuring the effect of the enzyme on the growth of a test yeast strain which does not express a functional BAR1 enzyme.

10. The assay of claim 6, wherein said enzyme is BAR1 protease.

11. The assay of claim 10, wherein said step of detecting comprises determining the cleavage of a substrate having a BAR1 peptide recognition sequence.

12. The assay of claim 11, wherein said substrate is naturally occurring.

13. The assay of claim 11, wherein said BAR1 substrate comprises at least one detectable label.

14. The assay of claim 11, wherein said substrate is a chimeric substrate comprising:
  a first polypeptide which, upon cleavage by BAR1, exposes an amino terminal Lys; and
  a second polypeptide linked to the carboxy terminus of said first polypeptide; wherein said step of detecting comprises measuring the stability of the chimeric substrate.

15. The assay of claim 11, wherein said substrate is not naturally occurring.

16. The assay of claim 15, wherein said substrate comprises the compound of SEQ ID NO:4.

17. The assay of claim 15, wherein said substrate comprises the compound of SEQ ID NO:5.

18. An assay for identifying a compound that modulates a heterologous receptor expressed by a yeast cell comprising:
  i) providing a yeast cell which expresses a heterologous receptor which is functionally integrated into an endogenous yeast signaling pathway, wherein said yeast cell comprises a gene which encodes a detectable protein and a chimeric nucleic acid construct, said construct comprising:
    a first segment derived from a first gene, said first segment encoding a polypeptide that is activated by e yeast signaling pathway, and
    a second segment derived from a second gene, said second segment encoding of a polypeptide that binds a DNA sequence in the regulatory region of said gene which encodes a detectable protein;
  such that said gene is rendered responsive to activation of a yeast signaling pathway;
  ii) contacting the yeast cell with a test compound; and
  iii) detecting an alteration in a signal produced by said detectable protein to thereby identify a compound that modulates the beterologous receptor.

19. The assay of claim 18, wherein said step of detecting an alteration in a signal produced by said detectable protein comprises measuring transcription of said gene encoding said detectable protein.

20. The assay of claim 18, wherein said signaling pathway is a yeast pheromone response pathway.

21. The assay of claim 20, wherein said first segment is derived from a Ste 12 gene.

22. The assay of claim 21, wherein said first segment encodes a polypeptide comprising amino acids 1–688 of Ste12.

23. The assay of claim 20, wherein said second segment is derived from a Pho4 gene.

24. The assay of claim 23, wherein said second segment encodes a polypeptide comprising amino acids 227–312 of Pho4.

25. The assay of claim 23, wherein said yeast cell comprises a mutation in its endogenous Pho4 gene.

26. The assay of claim 20, wherein said gene which encodes a detectable protein is the endogenous yeast Pho5 gene.

27. The assay of claim 26, wherein said step of measuring comprises detecting the activity of PHO5 acid phosphatase.

28. An assay for identifying a compound that modulates a heterologous orphan G protein-coupled receptor expressed by a yeast cell comprising:
  i) providing a yeast cell which expresses a heterologous orphan G protein-coupled receptor which is functionally integrated into an endogenous yeast signaling pathway, wherein said yeast cell comprises an endogenous gene operatively linked to a heterologous promoter at the natural location of said endogenous gene in said yeast cell, said promoter being responsive to signals produced by said yeast signaling pathway;
  ii) contacting the yeast cell with a non-peptidic test compound; and
  iii) detecting an alteration in a signal produced by the endogenous yeast gene;
to thereby identify a non-peptidic compound that modulates the heterologous orphan G-protein coupled receptor.

29. The assay of claim 28, wherein said non-peptidic test compound is a small organic molecule.

30. The assay of claim 28, wherein said heterologous orphan G protein-coupled receptor is the human FPRL-1 receptor.

31. An assay for identifying a compound that modulates a heterologous receptor expressed by a yeast cell comprising:
  i) providing a yeast cell which expresses a heterologous receptor which is functionally integrated into an endogenous yeast pheromone response pathway, wherein said yeast cell comprises an endogenous gene operatively linked to a heterologous promoter at the natural location of said endogenous gene in said yeast cell, said endogenous gene encoding a protease, and said promoter being responsive to signals produced by said pheromone response pathway;
  ii) contacting the yeast cell wit a test compound; and
  iii) detecting an alteration in a signal produced by the protease; to thereby identify a compound that modulates the heterologous receptor.

32. The assay of claim 31, wherein said promoter is non-naturally occurring.

33. The assay of claim 31, wherein said endogenous yeast gene is the BAR1 gene.

34. The assay of claim 31, wherein said promoter is naturally occurring.

35. The assay of claim 34, wherein the promoter is selected from the group consisting of the Fus1 promoter and the Fus 2 promoter.

36. An assay for identifying a compound that modulates a human FPRL-1 receptor expressed by a yeast cell comprising:
  i) providing a yeast cell which expresses a human FPRL-1 receptor which is functionally integrated into an endogenous yeast signaling pathway;
  ii) contacting the yeast cell with a non-peptidic test compound; and
  iii) detecting an alteration in a signal produced by the endogenous yeast signaling pathway;

to thereby identify a non-peptidic compound that modulates the human FPRL-1 receptor.

* * * * *

UNITED STATES PATENT AND TRADEMARK OFFICE
CERTIFICATE OF CORRECTION

| | |
|---|---|
| PATENT NO. | : 6,159,705 |
| DATED | : December 12, 2000 |
| INVENTOR(S) | : Joshua Trueheart, Jeremy I. Paul, Hans A. Fuernkranz, Debra Nathan, and Scott Holmes |

Page 1 of 1

It is certified that error appears in the above-identified patent and that said Letters Patent is hereby corrected as shown below:

Title page,
Please delete "RECOMBIANT YEAST CELLS FOR IDENTIFYING RECEPTOR EFFECTORS" and insert -- METHODS AND COMPOSITIONS FOR IDENTIFYING RECEPTOR EFFECTORS --.

Signed and Sealed this

Twenty fifth Day of September, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.    : 6,159,705
DATED         : December 12, 2000
INVENTOR(S)   : Trueheart et al.

It is certified that error appears in the above-identified patent and that said Letters Patent is hereby corrected as shown below:

Column 101,
Line 53, replace "e" with the word -- the --.
Line 54, delete the word "of".

Column 102,
Line 55, replace "wit" with the word -- with --.

Column 104,
Line 5, replace "e" with the word -- the --.

Signed and Sealed this

Eleventh Day of February, 2003

JAMES E. ROGAN
*Director of the United States Patent and Trademark Office*

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

CTAATCTCGA GTTAAGAAGG CCGTT                                             25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GTTAAGGATC CTGTACTCCA GATTT                                             25

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GATATCGTCT CACATGTCTG CAATTA                                            26

(2) INFORMATION FOR SEQ ID NO:4:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (x) FEATURE:
        (A) NAME/KEY: Modified site
        (B) LOCATION: 1
        (D) OTHER INFORMATION: /note= Trp is DABYL(GABA)modified (ix) FEATURE:
        (A) NAME/KEY: Modified site
        (B) LOCATION: 11
        (D) OTHER INFORMATION: /note= Tyr is EDANS modified (xi) SEQUENCE DESCRIPTION: SEQ ID NO:4:

Trp Leu Gln Leu Lys Pro Gly Gln Pro Met Tyr
1               5                   10

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (x) FEATURE:
        (A) NAME/KEY: Modified site
        (B) LOCATION: 1
        (D) OTHER INFORMATION: /note= Trp is CBZ modified (ix) FEATURE:
        (A) NAME/KEY: Modified site
        (B) LOCATION: 11
        (D) OTHER INFORMATION: /note= Tyr is Rhodamine modified (xi) SEQUENCE DESCRIPTION: SEQ ID NO:5:

```
Trp Leu Gln Leu Lys Pro Gly Gln Pro Met Tyr
 1               5                  10
```

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CCTCCGGTCT CCCATGTCAG AGAACGGCTC CTT                          33
```

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
CCTCCGGTCT GGGATCCGAG AGCATCTGCC TGGTGC                       36
```

(2) INFORMATION FOR SEQ ID NO:8:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
CGACTAAGCT TATGGGTGCA CCTCCTAAAA AGAAGAGAAA GGTAGCCCCG CACGGATCGA    60
GCCAT                                                               65
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CCGGAATTCC GTGCTCACGT TC                                              22

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CCGGAATTCA TGAAAGTCCA AATAACC                                     27

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCCTGCAGAA TTATATTATA TCAGGTTG                                  28

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GAGCAAAGGA GACAGAACAA GAGTAGCAGA AAGTCCAGCT GAAGCTTCGT ACGC        54

(2) INFORMATION FOR SEQ ID NO:13:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CACGTGCTCA CGTTCTGCTG TAGGTGACGG ATGTAGCATA GGCCACTAGT GGATCTG     57

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CATGAAGCTT CTCCTACTAC CAAGACTG                                   28

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GATCGAATTC GGTAATTTGG AATGGC                                     26

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GATCGAATTC CTGTTCCACC GGCC                                       24

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GATCTCTAGA GAGGCGATTG CTGTAATGC                                  29

(2) INFORMATION FOR SEQ ID NO:18:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

GGTGGGAGGG TGCTCTCTAG AAGGAAGTGT TCACC                           35

(2) INFORMATION FOR SEQ ID NO:19:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

GCCCAGGAGA CCAGACCATG GACTCCTTCA ATTATACCAC C        41

(2) INFORMATION FOR SEQ ID NO:20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CCCCTTAAGC GTGAGGCAGA AGCTACTCTG CAAAAGAAGA TC       42

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:21:

GAAGATCTTC AGCGGCCGAG TTGCATGTC                      29

(2) INFORMATION FOR SEQ ID NO:22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

GATATATTAA GGTAGGAAAC CATGGGGTGT ACAGTGAG            38

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

CGAGGCTCGA GGGAACGTAT AATTAAAGTA GTG                 33

-continued (2) INFORMATION FOR SEQ ID NO:24:

(i) SEQUENCE CHARACTERISTICS:
  (A) LENGTH: 34 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION: SEQ ID NO:24:

GCGCGGTACC AAGCTTCAAT TCGAGATAAT ACCC   34

(2) INFORMATION FOR SEQ ID NO:25:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION: SEQ ID NO:25:

CCCGAATCCA CCAATTTCTT TACG   24

(2) INFORMATION FOR SEQ ID NO:26:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION: SEQ ID NO:26:

GCGGCGTCGA CGCGGCCGCG TAACAGT   27

(2) INFORMATION FOR SEQ ID NO:27:

(i) SEQUENCE CHARACTERISTICS:
  (A) LENGTH: 37 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION: SEQ ID NO:27:

CTGCTGGAGC TCCGCCTGCT GCTGCTGGGT GCTGGAG   37

(2) INFORMATION FOR SEQ ID NO:28:

(i) SEQUENCE CHARACTERISTICS:
  (A) LENGTH: 43 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION: SEQ ID NO:28:

CTGCTGGTCG ACGCGGCCGC GGGGGTTCCT TCTTAGAAGC AGC   43

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:29:

GGGCTCGAGC CTTCTTAGAG CAGCTCGTAC                                           30

(2) INFORMATION FOR SEQ ID NO:30:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:30:

CTGCTGGAGC TCAAGTTGCT GCTGTTGGGT GCTGGGG                                   37

(2) INFORMATION FOR SEQ ID NO:31:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:31:

CTGCTGGTCG ACGCGGCCGC GCCCCTCAGA AGAGGCCGCG GTCC                           44

(2) INFORMATION FOR SEQ ID NO:32:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:32:

GGGCTCGAGC CTCAGAAGAG GCCGCAGTC                                            29

(2) INFORMATION FOR SEQ ID NO:33:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

CTGCTGGAGC TCAAGCTGCT GCTACTCGGT GCTGGAG                                   37

(2) INFORMATION FOR SEQ ID NO:34:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:34:

CTGCTGGTCG ACGCGGCCGC CACTAACATC CATGCTTCTC AATAAAGTC          49

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:35:

GGGCTCGAGC ATGCTTCTCA ATAAAGTCCA C          31

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:36:

GCATCCATCA ATAATCCAG          19

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:37:

GAAACAATGG ATCCACTTCT TAC          23

(2) INFORMATION FOR SEQ ID NO:38:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:38:

GGCGCCCGGT CTCCCATGGA AACCAACTTC TCCACT          36

(2) INFORMATION FOR SEQ ID NO:39:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:39:

GGCGCCCGGT CTCCGATCCC ATTGCCTGTA ACTCAGTCTC    40

(2) INFORMATION FOR SEQ ID NO:40:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:40:

Ser Leu Leu Trp Leu Thr Cys Arg Pro Trp Glu Ala Met
 1           5               10

(2) INFORMATION FOR SEQ ID NO:41:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:41:

TCTCTGCTTT GGCTGACTTG TCGGCCTTGG GAGGCGATG    39

(2) INFORMATION FOR SEQ ID NO:42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:42:

GGGCCATGGG GCCGCGGCGG TTG    23

(2) INFORMATION FOR SEQ ID NO:43:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:43:

CCCGGATCCT AAGTTAACAG CTTTTTGTAT AT    32

```
(2) INFORMATION FOR SEQ ID NO:44:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (ix) FEATURE:
        (A) NAME/KEY: CDS
        (B) LOCATION: 1..39

(xi) SEQUENCE DESCRIPTION: SEQ ID NO:44:

GTT TGT CCT GCG CGT TAT GTG CTG CCT GGG CCT GTT TTG              39
Val Cys Pro Ala Arg Tyr Val Leu Pro Gly Pro Val Leu
  1               5                  10

(2) INFORMATION FOR SEQ ID NO:45:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:45:

Val Cys Pro Ala Arg Tyr Val Leu Pro Gly Pro Val Leu
  1               5                  10

(2) INFORMATION FOR SEQ ID NO:46:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:46:

Leu Leu Leu Leu Gly Ala Gly Glu Ser Gly
  1               5                  10

(2) INFORMATION FOR SEQ ID NO:47:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:47:

Leu Glu Lys Gln Arg Asp Lys Asn Glu
  1               5
```